US012708643B2

(12) United States Patent
Sahin et al.

(10) Patent No.: US 12,708,643 B2
(45) Date of Patent: Aug. 18, 2026

(54) TREATMENT USING CYTOKINE ENCODING RNA

(71) Applicants: BioNTech RNA Pharmaceuticals GmbH, Mainz (DE); TRON—Translationale Onkologie An Der Universitätsmedizin Der Johannes Gutenberg-Universität Mainz Gemeinnützige GMBH, Mainz (DE)

(72) Inventors: Ugur Sahin, Mainz (DE); Lena Kranz, Mainz (DE); Mathias Vormehr, Mainz (DE); Mustafa Diken, Mainz (DE); Sebastian Kreiter, Mainz (DE); Bodo Tillmann, Mainz (DE)

(73) Assignees: BioNTech SE, Mainz (DE); TRON—Translationale Onkologie an der Universitätsmedizin der Johannes Gutenberg-Universität Mainz gemeinnützige GmbH, Mainz (DE)

( * ) Notice: Subject to any disclaimer, the term of this patent is extended or adjusted under 35 U.S.C. 154(b) by 1332 days.

(21) Appl. No.: 16/966,422

(22) PCT Filed: Feb. 8, 2019

(86) PCT No.: PCT/EP2019/053134

§ 371 (c)(1),
(2) Date: Jul. 30, 2020

(87) PCT Pub. No.: WO2019/154985

PCT Pub. Date: Aug. 15, 2019

(65) Prior Publication Data

US 2021/0113606 A1 Apr. 22, 2021

(30) Foreign Application Priority Data

Feb. 12, 2018 (WO) ................ PCT/EP2018/053454

(51) Int. Cl.

| | |
|---|---|
| ***A61K 31/7105*** | (2006.01) |
| ***A61K 40/11*** | (2025.01) |
| ***A61K 40/22*** | (2025.01) |
| ***A61K 40/42*** | (2025.01) |
| ***A61K 40/46*** | (2025.01) |
| ***C07K 14/54*** | (2006.01) |
| ***C07K 14/55*** | (2006.01) |
| *A61K 39/00* | (2006.01) |
| *C07K 16/28* | (2006.01) |

(52) U.S. Cl.

CPC .......... *A61K 31/7105* (2013.01); *A61K 40/11* (2025.01); *A61K 40/22* (2025.01); *A61K 40/42* (2025.01); *A61K 40/46* (2025.01); *C07K 14/5418* (2013.01); *C07K 14/55* (2013.01); *A61K 2039/505* (2013.01); *A61K 2039/53* (2013.01); *C07K 16/2818* (2013.01); *C07K 16/2827* (2013.01); *C07K 2319/30* (2013.01); *C07K 2319/31* (2013.01)

(58) Field of Classification Search

CPC .... A61K 31/7105; A61K 40/11; A61K 40/22; A61K 40/42; A61K 2039/505; A61K 2039/53; A61K 39/12; C07K 14/5418; C07K 14/55; C07K 2319/30; C07K 2319/31; C07K 14/4702

See application file for complete search history.

(56) References Cited

U.S. PATENT DOCUMENTS

| | | | | |
|---|---|---|---|---|
| 5,766,883 A * | 6/1998 | Ballance | .............. | C07K 14/765 435/254.2 |
| 7,589,179 B2 * | 9/2009 | Gillies | .............. | C07K 14/5418 424/134.1 |
| 2015/0017120 A1 * | 1/2015 | Wittrup | .............. | A61K 38/2013 424/85.2 |
| 2016/0168227 A1 * | 6/2016 | Kallen | ............ | A61K 39/00117 536/23.5 |
| 2022/0125836 A1 | 4/2022 | Sahin et al. | | |

FOREIGN PATENT DOCUMENTS

| | | |
|---|---|---|
| JP | 2017524713 | 8/2017 |
| WO | 2016025642 A1 | 2/2016 |
| WO | 2016200219 A1 | 12/2016 |

(Continued)

OTHER PUBLICATIONS

Kleponis et al.(Fueling the engine and releasing the break: combinational therapy of cancer vaccines and immune checkpoint inhibitors. Cancer Biol Med. Sep. 2015; 12(3):201-208).*

(Continued)

*Primary Examiner* — Kimberly Chong

(74) *Attorney, Agent, or Firm* — Neal, Gerber & Eisenberg LLP

(57) ABSTRACT

The present disclosure relates to methods and compositions for inducing an immune response in a subject comprising co-administering to the subject RNA encoding peptides or proteins used for vaccination and RNA encoding IL-2 attached to a pharmacokinetic modifying group and/or RNA encoding IL-7 attached to a pharmacokinetic modifying group. The vaccine is particularly effective if an immune checkpoint inhibitor such as an anti-PD-L1 antibody is further administered. The present disclosure further relates to methods involving the target-specific delivery of a cytokine to a target organ or target tissue.

35 Claims, 38 Drawing Sheets
(4 of 38 Drawing Sheet(s) Filed in Color)
Specification includes a Sequence Listing.

(56) References Cited

FOREIGN PATENT DOCUMENTS

| | | | |
|---|---|---|---|
| WO | 2017070618 | A1 | 4/2017 |
| WO | WO 2019/154985 | A1 | 8/2019 |

OTHER PUBLICATIONS

Kreiter, Sebastian, et al. ("Intranodal vaccination with naked antigen-encoding RNA elicits potent prophylactic and therapeutic antitumoral immunity." Cancer research 70.22 (2010): 9031-9040 hereinafter Kreiter et al. 2010).*
Chaplin, David D. ("Overview of the immune response." Journal of allergy and clinical immunology 125.2 (2010)).*
Jiang et al. ("Role of IL-2 in cancer immunotherapy." Oncoimmunology 5.6 (2016)).*
Lin et al. Lin, ("The role of IL-7 in immunity and cancer." Anticancer research 37.3 (2017): 963-967).*
Zhu et al. Cancer cell 2015 p. 489-501.*
Song et al. ("In vivo antitumor activity of a recombinant IL7/IL15 hybrid cytokine in mice." Molecular Cancer Therapeutics 15.10 (2016): 2413-2421).*
Kang, Hee Kyoung, et al. "Antimicrobial and immunomodulatory properties and applications of marine-derived proteins and peptides." Marine Drugs 17.6 (2019): 350.*
Adabi et al., *Iranian Biomedical Journal*, 21(2): 77-83 (2017).
Kang et al., *Journal of Virology*, 90(5): 2273-2284 (2016).
Kreiter et al., *Cancer Research*, 70(22): 9031-9040 (2010).
Kreiter et al., *Current Opinion in Immunology*, 23: 399-406 (2011).
Michel et al., *Molecular Therapy: Nucleic Acids*, 8: 459-468 (2017).
Vazquez-Lombardi et al., *Antibodies*, 2: 426-451 (2013).
European Patent Office, International Search Report in International Application No. PCT/EP2019/053134 (May 31, 2019).
European Patent Office, Written Opinion of the International Searching Authority in International Application No. PCT/EP2019/053134 (May 31, 2019).
Diken, et al., Curr. Issues Mol. Biol., 22, 113-128 (2017).
Jiang, et al., Oncommunology, 5(6), e1163462 (2016).
Lees, et al., Cancer Immunol. Immunother, 48, 644-652, (2000).

* cited by examiner

A
mIL-2 [pg/ml]
50,000
40,000
30,000
20,000
10,000
0
Mock
mIL2
mAlb-mIL2
mIfnb1-mIL2
mIfnb1-mAlb-mIL2
B
[kDa]
Marker
Mock
Mock
Mock
Mock
mIL2
mIL2
mIL2
mIFNB1-mIL2
mIFNB1-mIL2
mIFNB1-mIL2
mAlb-mIL2
mAlb-mIL2
mAlb-mIL2
mIFNB1-mAlb-mIL2
mIFNB1-mAlb-mIL2
mIFNB1-mAlb-mIL2
Marker
Marker
mIFNB1-mAlb-mIL2
mAlb-mIL2
mIFNB1-mIL2
60
40
30
20
M 1 2 3 4 5 6 7 8 9 10 11 12 13 14 15 16 M M
mIL2
C
CTLL-2 proliferation
60,000
40,000
20,000
0
Rec IL2
mAlb-mIL2
mIFNβ1-mIL2
mIFNβ1-mAlb-mIL2
0
1:1458
1:486
1:162
1:54
1:18
1:6
1:2
Supernatant dilution A
mIL15sushi [pg/ml]
300,000
200,000
100,000
0
Mock
mAlb
mIL15Ra-mIL15
mIL15Ra-mIL15-mAlb
B
[kDa]
150
100
75
50
37
25
20
10
MmIL15Ra-IL15-MmAlb
MmIL15Ra-IL15
Marker
Mock
MmIL15Ra-IL15
MmIL15Ra-IL15-MmAlb
M
1
2
3
4
5
6
7
8
9
10
11
12
C
CTLL-2 proliferation
60,000
40,000
20,000
0
Mock
mAlb
Rec hIL15sushi
mIL15sushi
mIL15sushi-mAlb
0
1:1458
1:486
1:162
1:54
1:18
1:6
1:2
Supernatant dilution Figure 3
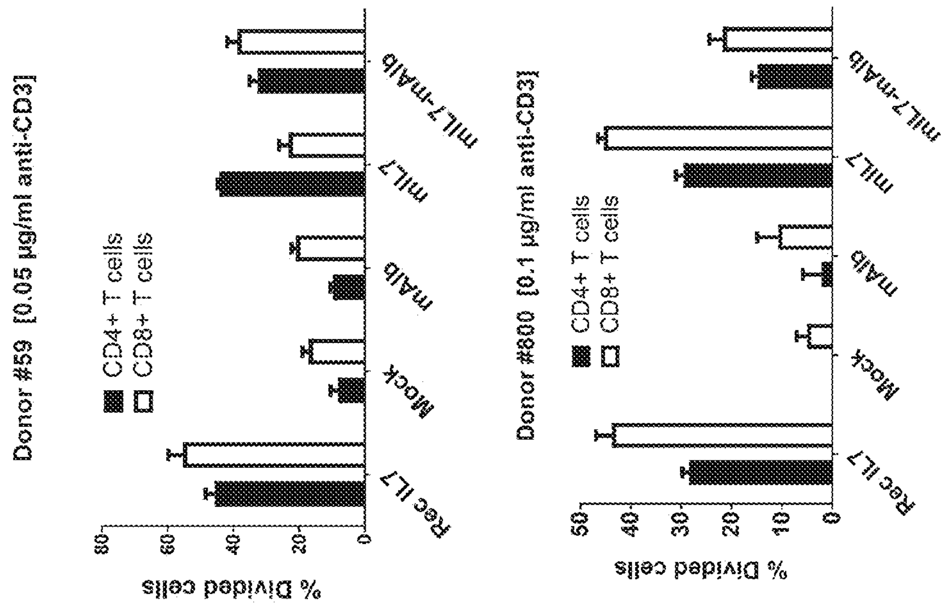
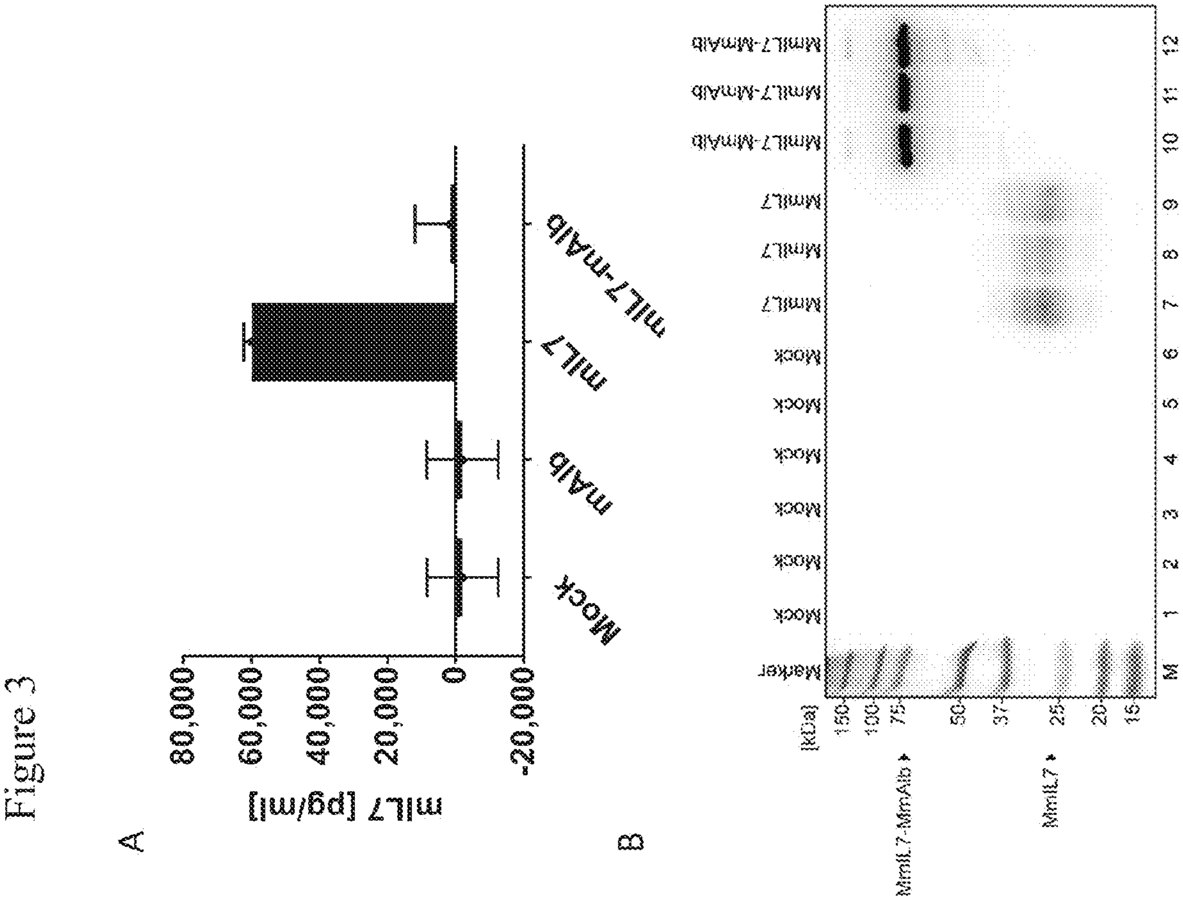

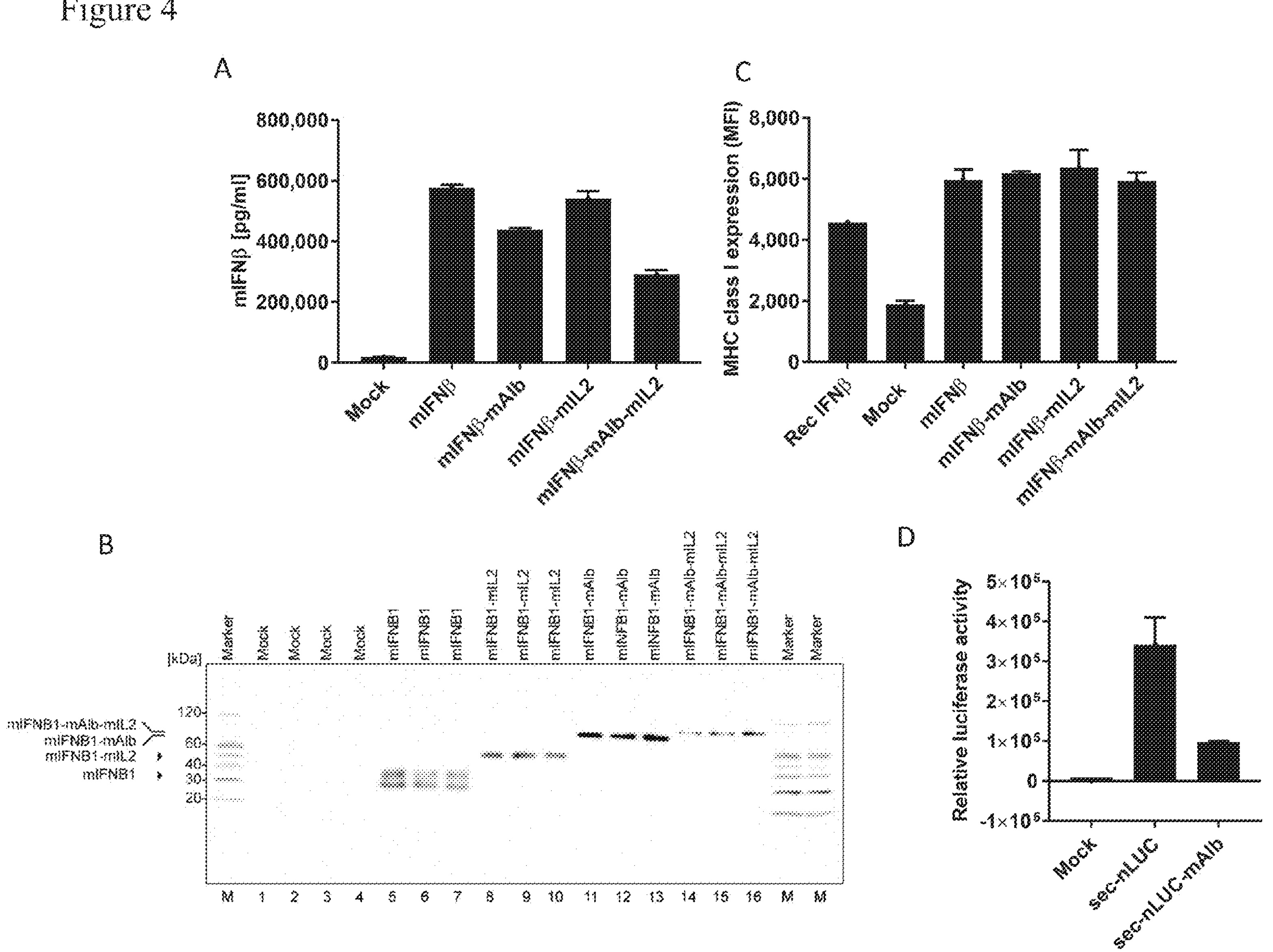
Figure 4
A
mIFNβ [pg/ml]
800,000
600,000
400,000
200,000
0
Mock
mIFNβ
mIFNβ-mAlb
mIFNβ-mIL2
mIFNβ-mAlb-mIL2
C
MHC class I expression (MFI)
8,000
6,000
4,000
2,000
0
Rec IFNβ
Mock
mIFNβ
mIFNβ-mAlb
mIFNβ-mIL2
mIFNβ-mAlb-mIL2
B
[kDa]
Marker
Mock
Mock
Mock
Mock
mIFNB1
mIFNB1
mIFNB1
mIFNB1-mIL2
mIFNB1-mIL2
mIFNB1-mIL2
mIFNB1-mAlb
mINFB1-mAlb
mINFB1-mAlb
mIFNB1-mAlb-mIL2
mIFNB1-mAlb-mIL2
mIFNB1-mAlb-mIL2
Marker
Marker
mIFNB1-mAlb-mIL2
mIFNB1-mAlb
mIFNB1-mIL2
mIFNB1
120
60
40
30
20
M 1 2 3 4 5 6 7 8 9 10 11 12 13 14 15 16 M M
D
Relative luciferase activity
5×10^5
4×10^5
3×10^5
2×10^5
1×10^5
0
-1×10^5
Mock
sec-nLUC
sec-nLUC-mAlb

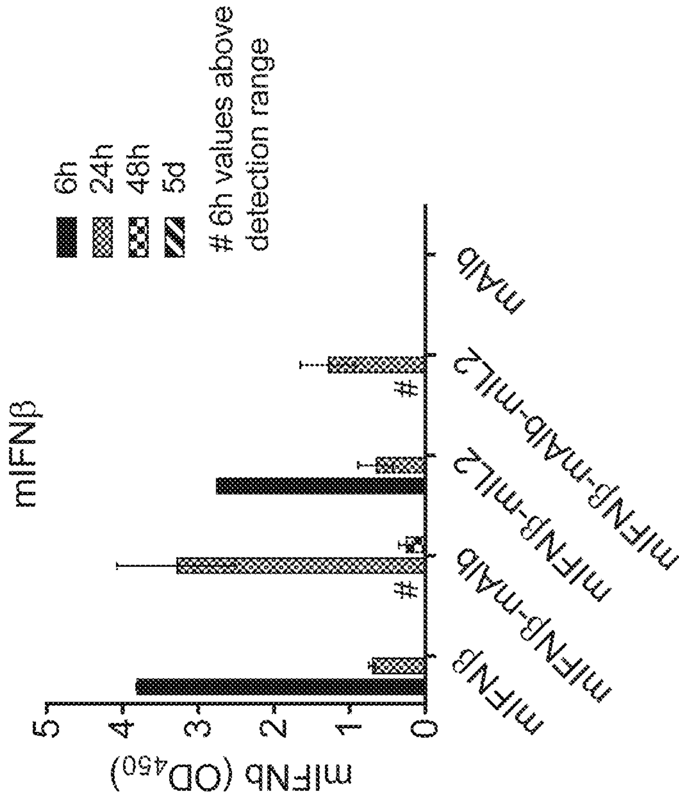
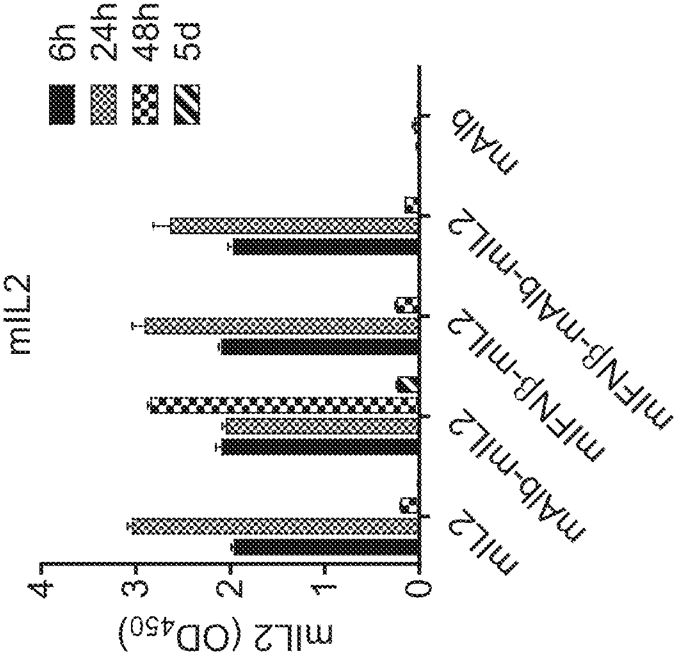
Figure 5

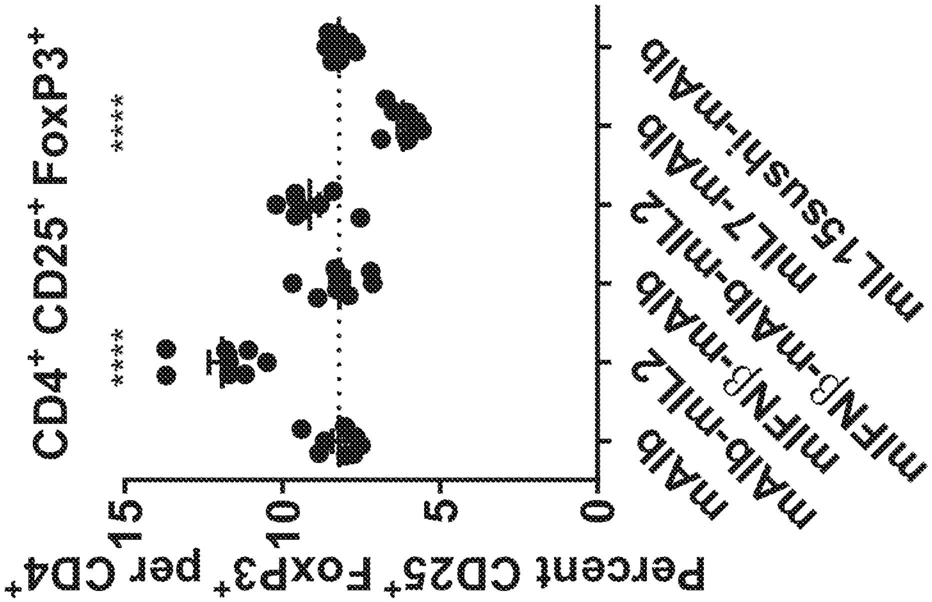
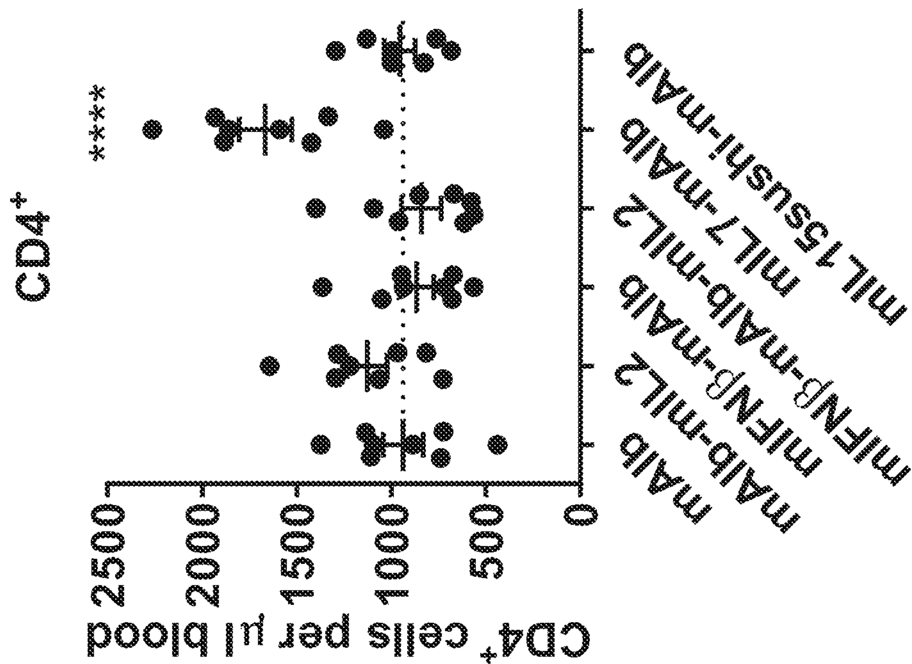
Figure 14

A

Figure 21
C
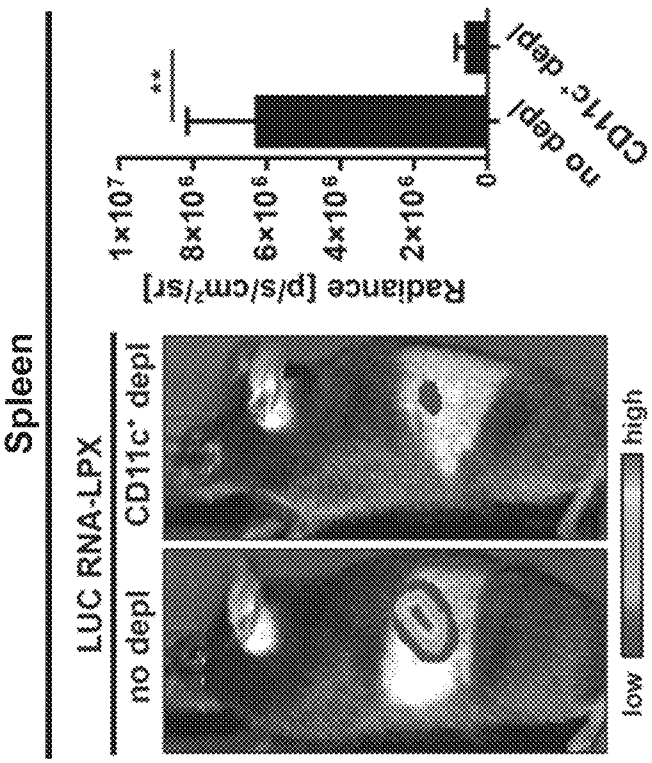
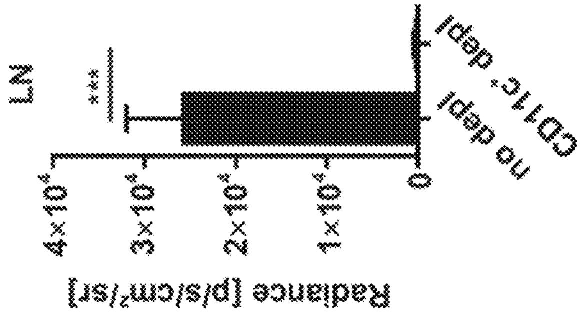
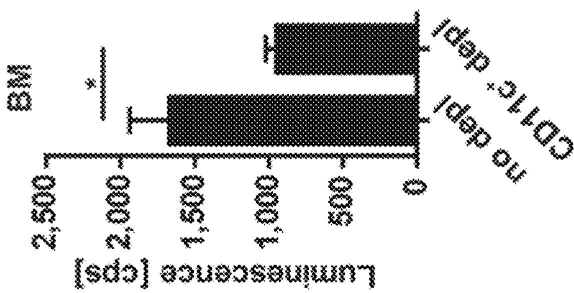

Figure 26
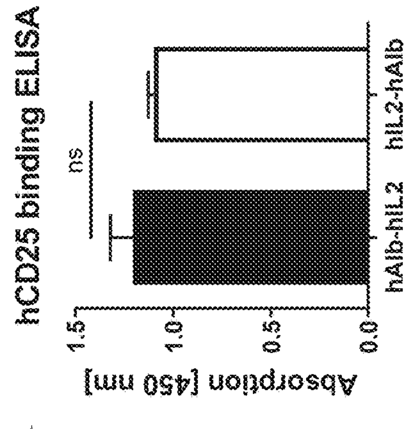
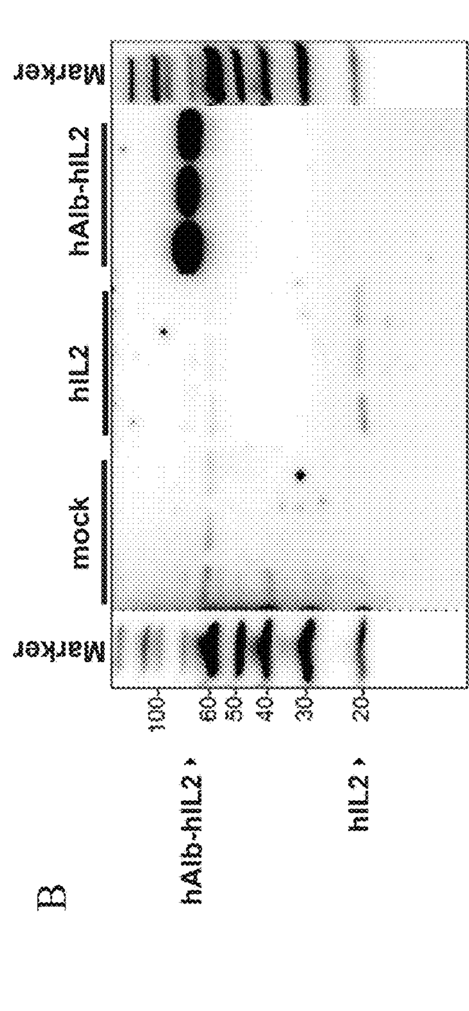
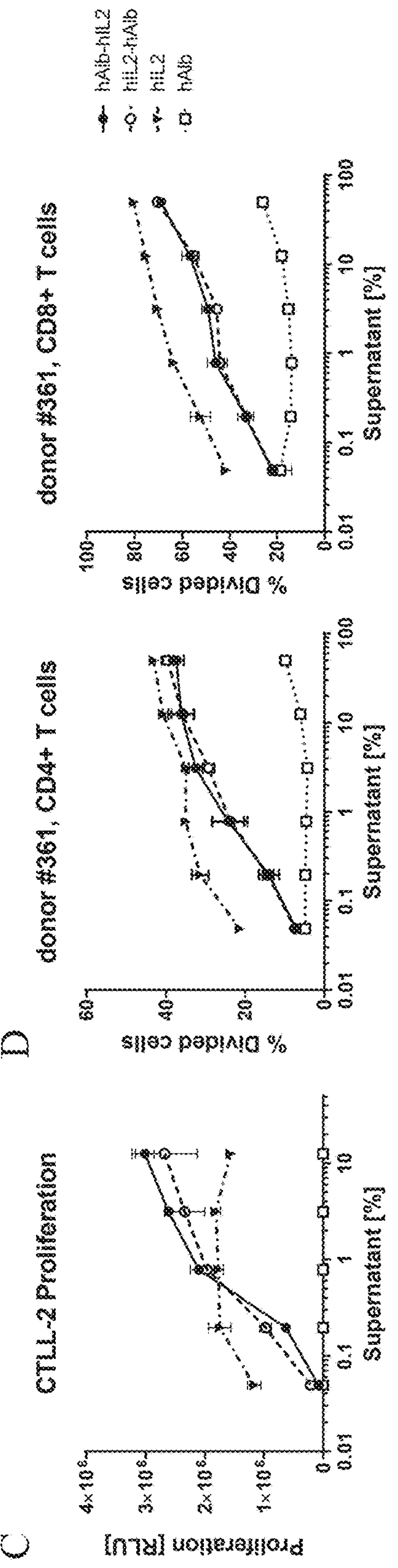

Figure 27
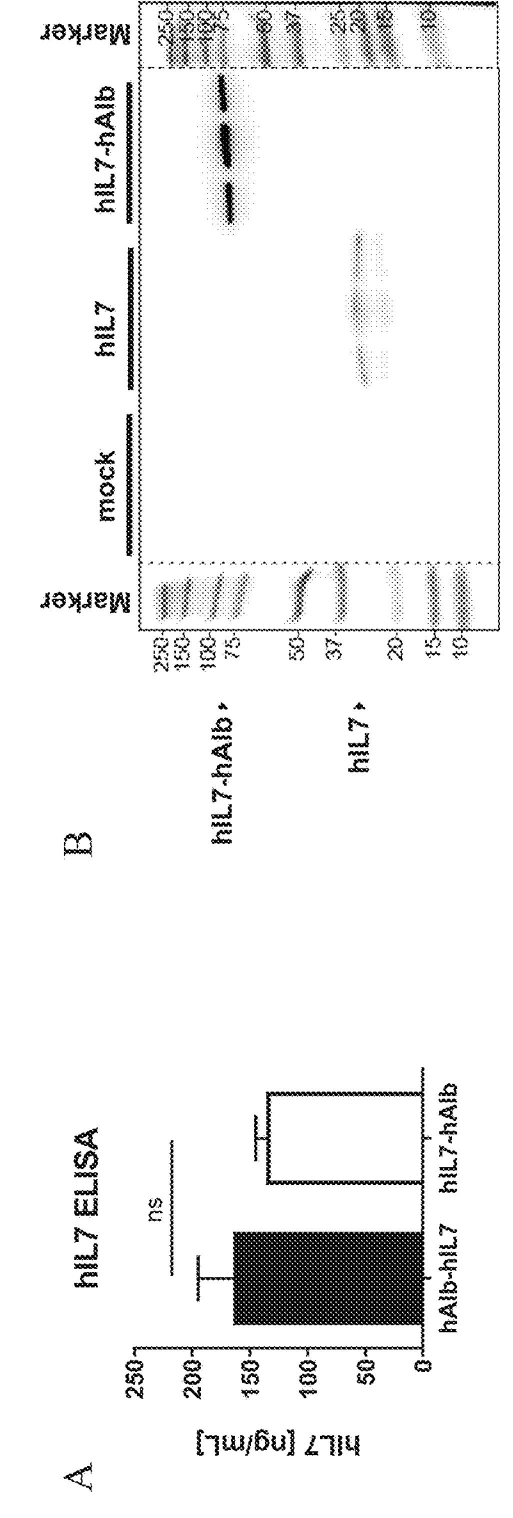
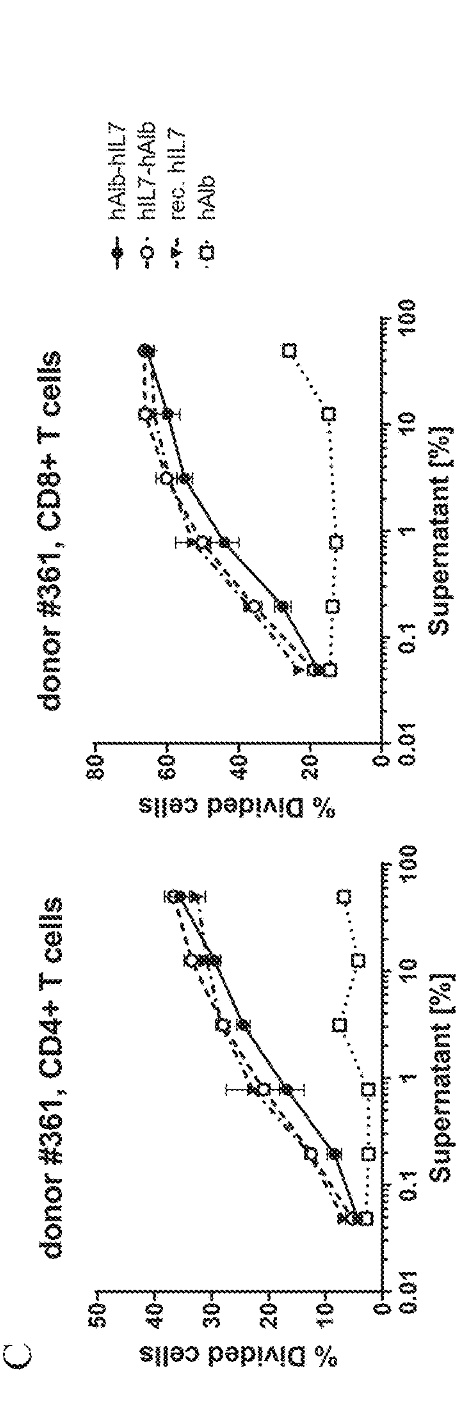

B

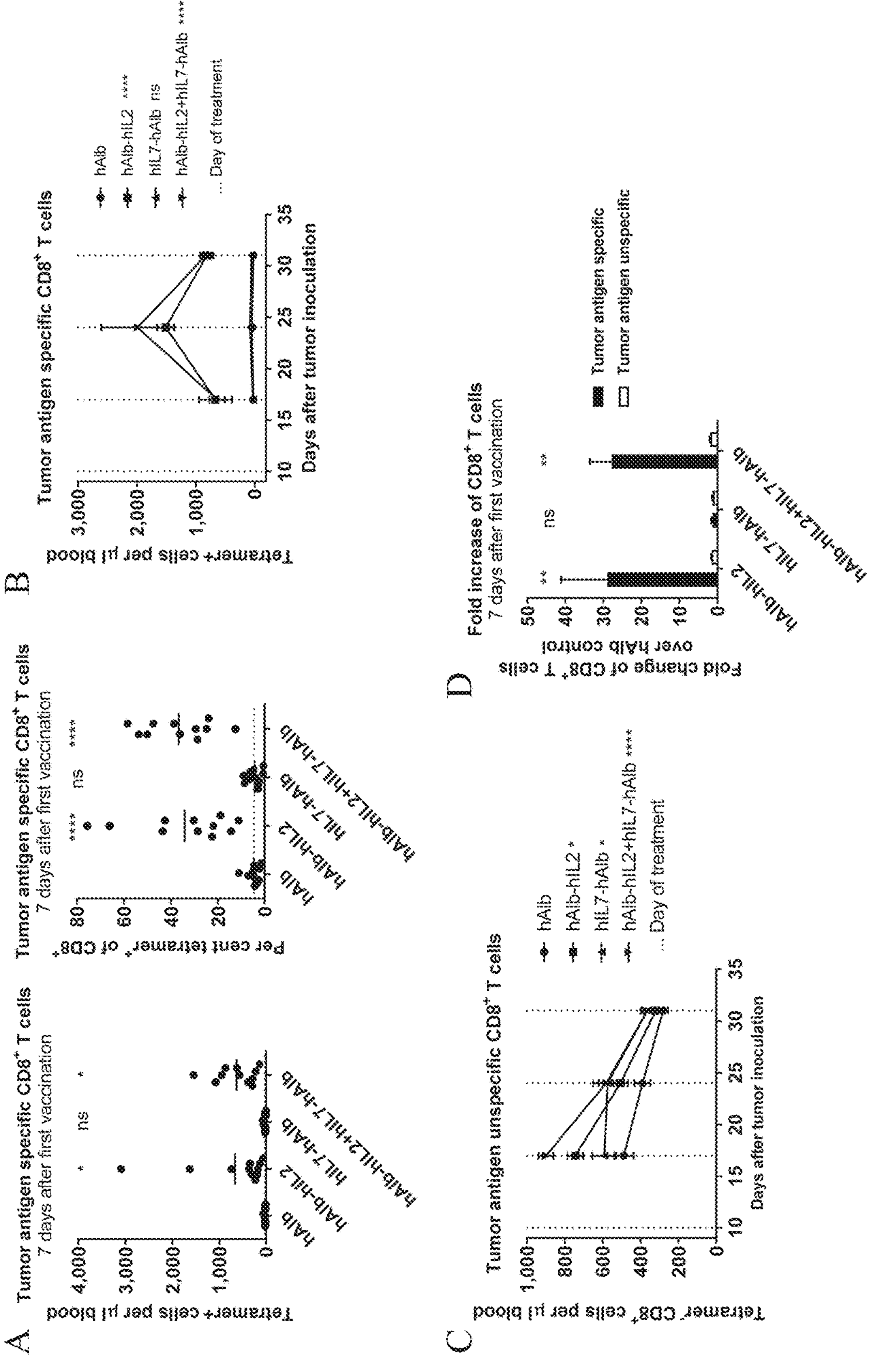
Figure 30
A
Tumor antigen specific CD8+ T cells
7 days after first vaccination
Tetramer+ cells per µl blood
4,000
3,000
2,000
1,000
0
*
ns
*
hAlb
hAlb-hIL2
hIL7-hAlb
hAlb-hIL2+hIL7-hAlb
Tumor antigen specific CD8+ T cells
7 days after first vaccination
Per cent tetramer+ of CD8+
80
60
40
20
0
****
ns
****
hAlb
hAlb-hIL2
hIL7-hAlb
hAlb-hIL2+hIL7-hAlb
B
Tumor antigen specific CD8+ T cells
Tetramer+ cells per µl blood
3,000
2,000
1,000
0
10
15
20
25
30
35
Days after tumor inoculation
hAlb
hAlb-hIL2 ****
hIL7-hAlb ns
hAlb-hIL2+hIL7-hAlb ****
... Day of treatment
C
Tumor antigen unspecific CD8+ T cells
Tetramer- CD8+ cells per µl blood
1,000
800
600
400
200
0
10
15
20
25
30
35
Days after tumor inoculation
hAlb
hAlb-hIL2 *
hIL7-hAlb *
hAlb-hIL2+hIL7-hAlb ****
... Day of treatment
D
Fold increase of CD8+ T cells
7 days after first vaccination
Fold change of CD8+ T cells over hAlb control
50
40
30
20
10
0
**
ns
**
hAlb-hIL2
hIL7-hAlb
hAlb-hIL2+hIL7-hAlb
Tumor antigen specific
Tumor antigen unspecific Figure 31
A
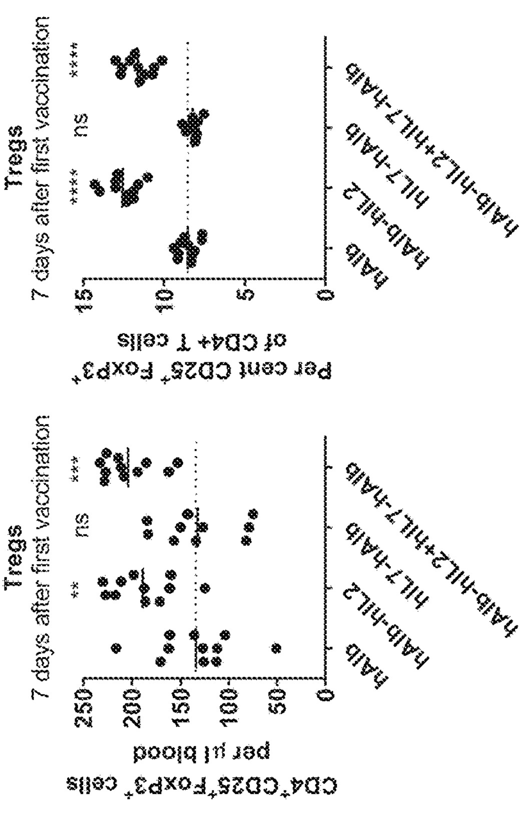
B
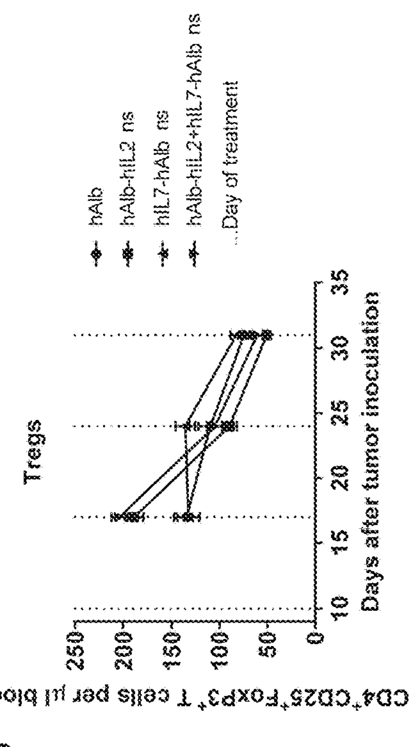

Figure 32
A
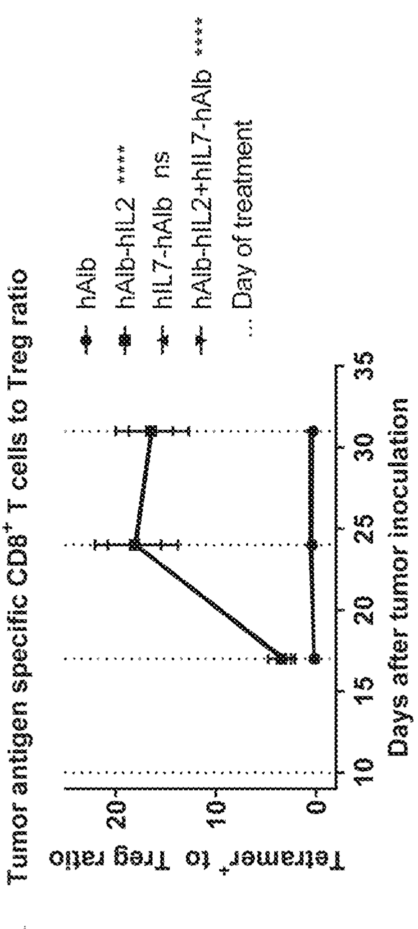
B
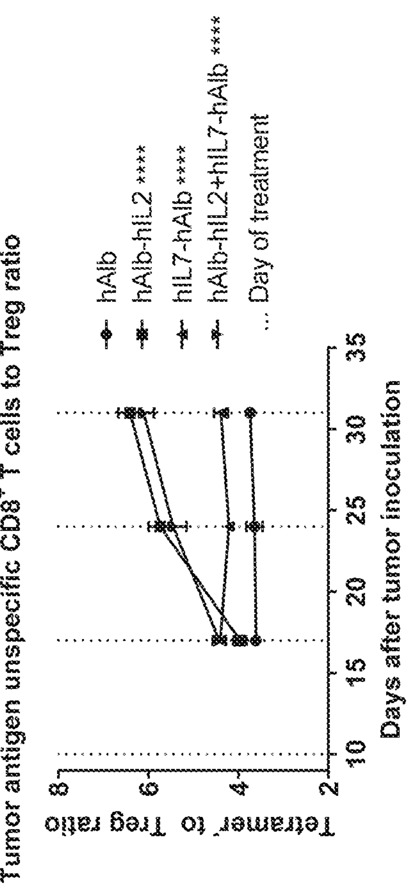

SEQUENCE LISTING

```
<160> NUMBER OF SEQ ID NOS: 5

<210> SEQ ID NO 1
<211> LENGTH: 133
<212> TYPE: PRT
<213> ORGANISM: Homo sapiens

<400> SEQUENCE: 1

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95
```

```
Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130


<210> SEQ ID NO 2
<211> LENGTH: 152
<212> TYPE: PRT
<213> ORGANISM: Homo sapiens

<400> SEQUENCE: 2

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His
145                 150


<210> SEQ ID NO 3
<211> LENGTH: 166
<212> TYPE: PRT
<213> ORGANISM: Homo sapiens

<400> SEQUENCE: 3

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125
```

```
Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165


<210> SEQ ID NO 4
<211> LENGTH: 165
<212> TYPE: PRT
<213> ORGANISM: Homo sapiens

<400> SEQUENCE: 4

Arg Ser Tyr Ser Leu Leu Arg Phe Gln Gln Arg Arg Ser Leu Ala Leu
1               5                   10                  15

Cys Gln Lys Leu Leu Arg Gln Leu Pro Ser Thr Pro Gln His Cys Leu
            20                  25                  30

Glu Ala Arg Met Asp Phe Gln Met Pro Glu Glu Met Lys Gln Ala Gln
        35                  40                  45

Gln Phe Gln Lys Glu Asp Ala Ile Leu Val Ile Tyr Glu Met Leu Gln
    50                  55                  60

Gln Ile Phe Asn Ile Leu Thr Arg Asp Phe Ser Ser Thr Gly Trp Ser
65                  70                  75                  80

Glu Thr Ile Ile Glu Asp Leu Leu Glu Glu Leu Tyr Glu Gln Met Asn
                85                  90                  95

His Leu Glu Pro Ile Gln Lys Glu Ile Met Gln Lys Gln Asn Ser Thr
            100                 105                 110

Met Gly Asp Thr Thr Val Leu His Leu Arg Lys Tyr Tyr Phe Asn Leu
        115                 120                 125

Val Gln Tyr Leu Lys Ser Lys Glu Tyr Asn Arg Cys Ala Trp Thr Val
    130                 135                 140

Val Arg Val Gln Ile Leu Arg Asn Phe Ser Phe Leu Thr Arg Leu Thr
145                 150                 155                 160

Gly Tyr Leu Arg Glu
                165


<210> SEQ ID NO 5
<211> LENGTH: 585
<212> TYPE: PRT
<213> ORGANISM: Homo sapiens

<400> SEQUENCE: 5

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110
```

-continued

```
Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
```

-continued

```
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585
```

TREATMENT USING CYTOKINE ENCODING RNA

CROSS-REFERENCE TO RELATED APPLICATIONS

This application is a National Stage Entry of International Application Number PCT/EP2019/053134, which was filed on Feb. 8, 2019 and claimed priority to International Application Number PCT/EP2018/053454, which was filed on Feb. 12, 2018. The contents of each of the aforementioned applications are incorporated herein by reference in their entireties.

SEQUENCE LISTING

The computer-readable Sequence Listing submitted on Jul. 30, 2020 and identified as follows: 10,901 bytes ASCII text file named "SequenceListing.txt," created Jul. 30, 2020, is incorporated herein by reference in its entirety.

TECHNICAL FIELD

The present disclosure relates to methods and compositions for inducing an immune response in a subject comprising co-administering to the subject RNA encoding peptides or proteins used for vaccination and RNA encoding IL2 attached to a pharmacokinetic modifying group and/or RNA encoding IL7 attached to a pharmacokinetic modifying group. The vaccine is particularly effective if an immune checkpoint inhibitor such as an anti-PD-L1 antibody is further administered. The present disclosure further relates to methods involving the target-specific delivery of a cytokine to a target organ or target tissue.

BACKGROUND

The immune system plays an important role in cancer, autoimmunity, allergy as well as in pathogen-associated diseases. T cells are important mediators of anti-tumor immune responses. CD8+ T cells can directly lyse tumor cells. CD4+ T cells, on the other hand, can mediate the influx of different immune subsets including CD8+ T cells and NK cells into the tumor. They are able to license dendritic cells (DCs) for the priming of anti-tumor CD8+ T-cell responses and can act directly on tumor cells via IFNγ mediated MHC upregulation and growth inhibition. CD8+ as well as CD4+ tumor specific T-cell responses can be induced via vaccination. In the context of an mRNA based vaccine platform, mRNA may be delivered via liposomal formulation (RNA-LPX) into antigen presenting cells located in secondary lymphoid organs without requirement for any additional adjuvant (Kreiter, S. et al. Nature 520, 692-696 (2015); Kranz, L. M. et al. Nature 534, 396-401 (2016)).

Tumors are known to escape T-cell mediated attack by upregulation of PD-L1 or by attraction of PD-L1 expressing immune cells. Interaction of PD-L1 and PD-1 on T cells inhibits their anti-tumoral functions. Antibodies blocking the PD-1/PD-L1 axis were shown to induce potent tumor control in a subset of patients with a high mutational burden correlating with an increased likelihood of pre-existing T-cell responses (Rizvi, N. A. et al. Science 348, 124-128 (2015)).

Hence, T-cell vaccines may benefit from PD-1/PD-L1 checkpoint blockade mediated reinvigoration of T cells. On the other hand, checkpoint blockade could benefit from T-cell vaccines in patients without a pre-existing T-cell response. Combination of mRNA vaccination and anti-PD-L1 checkpoint blockade is currently under clinical investigation (RO7198457).

Cytokines play an important role in immunity. For example, interleukin-2 (IL2) is known to support the differentiation, proliferation, survival and effector functions of T cells (Blattman, J. N. et al. Nat. Med. 9, 540-7 (2003)). Recombinant IL2, for example, has been used for decades in the treatment of late stage malignant melanoma (Maas, R. A., Dullens, H. F. & Den Otter, W. Cancer Immunol. Immunother. 36, 141-8 (1993)). Interleukin-7 (IL7) has been shown to play an important role in T and B cell lymphopoiesis and survival as well as memory T cell formation (Kaech, S. M. et al. Nat. Immunol. 4, 1191-1198 (2003); Fry, T. J. & Mackall, C. L. Blood 99, 3892-3904 (2002); Palmer, M. J. et al. Cell. Mol. Immunol. 5, 79-89 (2008)). On their own, these cytokines are ineffective cancer treatments. However, addition of cytokines to immunotherapies such as cancer vaccines and immune checkpoint blockade promises to further boost T-cell responses leading to a superior anti-tumor effect.

A complex interplay between cellular components such as dendritic cells (DC) and T cells as well as soluble components such as cytokines and chemokines regulate whether immunity is rather pro-inflammatory or predominantly tolerogenic. Therefore, there is a tight spatio-temporal regulation of cytokine expression in order to limit their activity to the cell of interest and to prevent toxic effects. Some cytokines such as interleukin-12 (IL12) are critically required during priming of a Th1 T-cell response (i.e. important for cancer/virus immunity) in the lymph node or the spleen but are unfavorable or even highly toxic when systemically administered (Lasek, W., Zagożdżon, R. & Jakobisiak, M. Cancer Immunol. Immunother. 63, 419-35 (2014)). Other cytokines like IL7 are required systemically for maintenance of T-cells in blood and tissue (Kaech, S. M. et al. Nat. Immunol. 4, 1191-8 (2003); Fry, T. J. & Mackall, C. L. Blood 99, 3892-3904 (2002); Palmer, M. J. et al. Cell. Mol. Immunol. 5, 79-89 (2008)). Again other cytokines, such as IL2, are not only required in the secondary lymphoid organs during T cell priming but also during maintenance in the blood and tissue or, in the case of cancer immunity, during the effector function of T cells in the tumor (Blattman, J. N. et al. Nat. Med. 9, 540-7 (2003)).

Cancer vaccines can be used to stimulate the immune system against an antigen expressed by tumor cells. These therapies show promising results, however, their effectiveness remains limited.

There is a need for novel strategies to increase the effectiveness of vaccines, in particular cancer vaccines.

SUMMARY

The inventors surprisingly found that the effectiveness of RNA encoding peptides or proteins used for vaccination (RNA encoding antigen) can be increased by co-administering RNA encoding IL2 attached to a pharmacokinetic modifying group (hereafter referred to as "extended-pharmacokinetic (PK) IL2") and/or RNA encoding IL7 attached to a pharmacokinetic modifying group (hereafter referred to as "extended-pharmacokinetic (PK) IL7"). The vaccine is particularly effective if the RNA encoding extended-PK IL2 and/or the RNA encoding extended-PK IL7 is targeted to the liver for systemic availability. Liver cells can be efficiently transfected and are able to produce large amounts of protein. Antigen-encoding mRNA is preferably targeted to secondary lymphoid organs. Furthermore, the vaccine is particularly effective if an immune checkpoint inhibitor such as an anti-PD-L1 antibody is further administered.

In one aspect, the invention relates to a method for inducing an immune response in a subject comprising administering to the subject:

a. RNA encoding extended pharmacokinetic (PK) interleukin (IL)-2 and/or RNA encoding extended pharmacokinetic (PK) interleukin (IL)-7; and
b. RNA encoding a peptide or protein comprising an epitope for inducing an immune response against an antigen in said subject.

In one embodiment, the extended-PK IL2 comprises a fusion protein. In one embodiment, the fusion protein comprises an IL2 moiety and a moiety selected from the group consisting of serum albumin, an immunoglobulin fragment, transferrin, and Fn3, or variants thereof.

In one embodiment, the extended-PK IL7 comprises a fusion protein. In one embodiment, the fusion protein comprises an IL7 moiety and a moiety selected from the group consisting of serum albumin, an immunoglobulin fragment, transferrin, and Fn3, or variants thereof.

In one embodiment, the serum albumin comprises mouse serum albumin or human serum albumin. In one embodiment, the immunoglobulin fragment comprises an immunoglobulin Fc domain.

In one embodiment, the method further comprises administering to the subject:

c. an immune checkpoint inhibitor.

In one embodiment, the immune checkpoint inhibitor targets the interaction between (i) PD-1 and PD-L1, or (ii) CTLA-4 and CD80 or CD86. In one embodiment, the immune checkpoint inhibitor is an antibody or antibody fragment. In one embodiment, the antibody or antibody fragment targets PD-1, PD-L1, or CTLA-4.

In one embodiment, the RNA encoding extended-PK IL2 and/or the RNA encoding extended-PK IL7, the RNA encoding a peptide or protein comprising an epitope for inducing an immune response against an antigen in said subject, and optionally the immune checkpoint inhibitor are administered simultaneously or sequentially.

In one embodiment, the method comprises administering to the subject:

a. the RNA encoding extended-PK IL2 and optionally the RNA encoding extended-PK IL7;
b. the RNA encoding a peptide or protein comprising an epitope for inducing an immune response against an antigen in said subject; and
c. the immune checkpoint inhibitor.

In one embodiment, the method comprises administering to the subject:

a. the RNA encoding extended-PK IL7 and optionally the RNA encoding extended-PK IL2;
b. the RNA encoding a peptide or protein comprising an epitope for inducing an immune response against an antigen in said subject; and
c. the immune checkpoint inhibitor.

In one embodiment, the method comprises administering to the subject:

a-1. the RNA encoding extended-PK IL2;
a-2. the RNA encoding extended-PK IL7;
b. the RNA encoding a peptide or protein comprising an epitope for inducing an immune response against an antigen in said subject; and
c. the immune checkpoint inhibitor.

In one embodiment, the treatment increases the number of CD127 positive T cells which are specific for the antigen. In one embodiment, the treatment decreases the number of short-lived effector cells. In one embodiment, the treatment increases the ratio of antigen-specific T cells to T regulatory cells.

In one embodiment, the method is a method for treating or preventing cancer in a subject, wherein the antigen is a tumor-associated antigen. In one embodiment, no therapeutic antibody or antibody fragment against a tumor antigen is administered.

In a further aspect, the invention relates to a method for treating or preventing cancer in a subject comprising administering to the subject:

a. RNA encoding extended pharmacokinetic (PK) interleukin (IL)-2 and/or RNA encoding extended pharmacokinetic (PK) interleukin (IL)-7; and
b. RNA encoding a peptide or protein comprising an epitope for inducing an immune response against a tumor-associated antigen in said subject.

In one embodiment, the cancer is selected from the group consisting of melanoma, leukemia, lymphoma, lung cancer, breast cancer, prostate cancer, ovarian cancer, colon cancer, mesothelioma, renal cell carcinoma, and brain cancer.

Embodiments of the method for treating or preventing cancer in a subject are as described above for the method for inducing an immune response in a subject.

In a further aspect, the invention relates to a medical preparation comprising:

a. RNA encoding extended pharmacokinetic (PK) interleukin (IL)-2 and/or RNA encoding extended pharmacokinetic (PK) interleukin (IL)-7; and
b. RNA encoding a peptide or protein comprising an epitope for inducing an immune response against an antigen in a subject.

In one embodiment, the extended-PK IL2 comprises a fusion protein. In one embodiment, the fusion protein comprises an IL2 moiety and a moiety selected from the group consisting of serum albumin, an immunoglobulin fragment, transferrin, and Fn3, or variants thereof.

In one embodiment, the extended-PK IL7 comprises a fusion protein. In one embodiment, the fusion protein comprises an IL7 moiety and a moiety selected from the group consisting of serum albumin, an immunoglobulin fragment, transferrin, and Fn3, or variants thereof.

In one embodiment, the serum albumin comprises mouse serum albumin or human serum albumin. In one embodiment, the immunoglobulin fragment comprises an immunoglobulin Fc domain.

In one embodiment, the medical preparation further comprises:

c. an immune checkpoint inhibitor.

In one embodiment, the immune checkpoint inhibitor targets the interaction between (i) PD-1 and PD-L1, or (ii) CTLA-4 and CD80 or CD86. In one embodiment, the immune checkpoint inhibitor is an antibody or antibody fragment. In one embodiment, the antibody or antibody fragment targets PD-1, PD-L1, or CTLA-4.

In one embodiment, the medical preparation comprises:

a. the RNA encoding extended-PK IL2 and/or the RNA encoding extended-PK IL7;
b. the RNA encoding a peptide or protein comprising an epitope for inducing an immune response against an antigen in a subject; and
c. the immune checkpoint inhibitor.

In one embodiment, the medical preparation comprises:

a-1. the RNA encoding extended-PK IL2;
a-2. the RNA encoding extended-PK IL7;

b. the RNA encoding a peptide or protein comprising an epitope for inducing an immune response against an antigen in a subject; and c. the immune checkpoint inhibitor.

In one embodiment, the medical preparation is a kit. In one embodiment, the medical preparation comprises each RNA in a separate container. In one embodiment, the immune checkpoint inhibitor is in a container not comprising the RNA. In one embodiment, the medical preparation further comprises instructions for use of the medical preparation for treating or preventing cancer wherein the antigen is a tumor-associated antigen.

In one embodiment, the medical preparation is a pharmaceutical composition comprising the RNAs. In one embodiment, the pharmaceutical composition further comprises one or more pharmaceutically acceptable carriers, diluents and/or excipients.

In one embodiment of the medical preparation, the RNA is present in a form selected from a liquid form, a solid form, or a combination thereof. In one embodiment, the solid form is a frozen form or a dehydrated form. In one embodiment, the dehydrated form is a freeze-dried or spray-dried form.

In a further aspect, the invention relates to the medical preparation described herein for pharmaceutical use. In one embodiment, the pharmaceutical use comprises a therapeutic or prophylactic treatment of a disease or disorder.

In a further aspect, the invention relates to the medical preparation described herein for use in a method for treating or preventing cancer in a subject, wherein the antigen is a tumor-associated antigen.

In one embodiment, the cancer described herein is selected from the group consisting of melanoma, leukemia, lymphoma, lung cancer, breast cancer, prostate cancer, ovarian cancer, colon cancer, mesothelioma, renal cell carcinoma, and brain cancer.

In one embodiment, the medical preparation does not comprise a therapeutic antibody or antibody fragment against a tumor antigen.

In a further aspect, the invention relates to RNA for use in a method for inducing an immune response in a subject, wherein the method comprises administering to the subject:

a. RNA encoding extended pharmacokinetic (PK) interleukin (IL)-2 and/or RNA encoding extended pharmacokinetic (PK) interleukin (IL)-7; and b. RNA encoding a peptide or protein comprising an epitope for inducing an immune response against an antigen in said subject.

In one embodiment, the extended-PK IL2 comprises a fusion protein. In one embodiment, the fusion protein comprises an IL2 moiety and a moiety selected from the group consisting of serum albumin, an immunoglobulin fragment, transferrin, and Fn3, or variants thereof.

In one embodiment, the extended-PK IL7 comprises a fusion protein. In one embodiment, the fusion protein comprises an IL7 moiety and a moiety selected from the group consisting of serum albumin, an immunoglobulin fragment, transferrin, and Fn3, or variants thereof.

In one embodiment, the serum albumin comprises mouse serum albumin or human serum albumin. In one embodiment, the immunoglobulin fragment comprises an immunoglobulin Fc domain.

In one embodiment of the RNA, the method further comprises administering to the subject:

c. an immune checkpoint inhibitor.

In one embodiment, the immune checkpoint inhibitor targets the interaction between (i) PD-1 and PD-L1, or (ii) CTLA-4 and CD80 or CD86. In one embodiment, the immune checkpoint inhibitor is an antibody or antibody fragment. In one embodiment, the antibody or antibody fragment targets PD-1, PD-L1, or CTLA-4.

In one embodiment, the RNA encoding extended-PK IL2 and/or the RNA encoding extended-PK IL7, the RNA encoding a peptide or protein comprising an epitope for inducing an immune response against an antigen in said subject, and optionally the immune checkpoint inhibitor are administered simultaneously or sequentially.

In one embodiment of the RNA, the method comprises administering to the subject:

a. the RNA encoding extended-PK IL2 and optionally the RNA encoding extended-PK IL7;

b. the RNA encoding a peptide or protein comprising an epitope for inducing an immune response against an antigen in said subject; and c. the immune checkpoint inhibitor.

In one embodiment of the RNA, the method comprises administering to the subject:

a. the RNA encoding extended-PK IL7 and optionally the RNA encoding extended-PK IL2;

b. the RNA encoding a peptide or protein comprising an epitope for inducing an immune response against an antigen in said subject; and c. the immune checkpoint inhibitor.

In one embodiment of the RNA, the method comprises administering to the subject:

a-1. the RNA encoding extended-PK IL2;

a-2. the RNA encoding extended-PK IL7;

b. the RNA encoding a peptide or protein comprising an epitope for inducing an immune response against an antigen in said subject; and c. the immune checkpoint inhibitor.

In one embodiment of the RNA, the treatment increases the number of CD127 positive T cells which are specific for the antigen. In one embodiment of the RNA, the treatment decreases the number of short-lived effector cells. In one embodiment of the RNA, the treatment increases the ratio of antigen-specific T cells to T regulatory cells.

In one embodiment of the RNA, the method is a method for treating or preventing cancer in a subject, wherein the antigen is a tumor-associated antigen. In one embodiment, no therapeutic antibody or antibody fragment against a tumor antigen is administered.

In a further aspect, the invention relates to RNA for use in a method for treating or preventing cancer in a subject comprising administering to the subject:

a. RNA encoding extended pharmacokinetic (PK) interleukin (IL)-2 and/or RNA encoding extended pharmacokinetic (PK) interleukin (IL)-7; and b. RNA encoding a peptide or protein comprising an epitope for inducing an immune response against a tumor-associated antigen in said subject.

In one embodiment, the cancer is selected from the group consisting of melanoma, leukemia, lymphoma, lung cancer, breast cancer, prostate cancer, ovarian cancer, colon cancer, mesothelioma, renal cell carcinoma, and brain cancer.

In one embodiment, the RNA is or comprises one or more of the RNAs administered in said method. In one embodiment, the RNA is or comprises one or more selected from the group consisting of the RNA encoding extended-PK IL2, the RNA encoding extended-PK IL7, and the RNA encoding a peptide or protein comprising an epitope for inducing an immune response against an antigen in said subject. In one embodiment, the RNA is or comprises the RNA encoding extended-PK IL2. In one embodiment, the RNA is or comprises the RNA encoding extended-PK IL7. In one embodiment, the RNA is or comprises the RNA encoding a peptide or protein comprising an epitope for inducing an immune response against an antigen in said subject.

In one embodiment, the RNA is or comprises a. the RNA encoding extended-PK IL2 and/or the RNA encoding extended-PK IL7; and
b. the RNA encoding a peptide or protein comprising an epitope for inducing an immune response against an antigen in said subject.

In one embodiment, the RNA is or comprises a-1. the RNA encoding extended-PK IL2;
a-2. the RNA encoding extended-PK IL7; and
b. the RNA encoding a peptide or protein comprising an epitope for inducing an immune response against an antigen in said subject.

In one embodiment of all aspects described herein, RNA encoding extended pharmacokinetic (PK) interleukin (IL)-2 and/or RNA encoding extended pharmacokinetic (PK) interleukin (IL)-7 is delivered to liver for expression of the encoded protein and/or is formulated for delivery to liver. In one embodiment of all aspects described herein, RNA encoding a peptide or protein comprising an epitope is delivered to the lymphatic system for expression of the encoded protein and/or is formulated for delivery to the lymphatic system.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

A, ELISA analysis of HEK-293T-17 supernatants after expression of mIL2 encoding constructs. HEK-293T-17 cells were lipofected with mRNAs encoding for the indicated proteins or without mRNA (Mock), supernatants were harvested after 24 h of expression and used for ELISA analysis. B, Western blot analysis of HEK-293T-17 supernatants after 24 h of expression of mIL2 encoding mRNAs. HEK-293T-17 cells were lipofected with mRNAs encoding for the indicated proteins, supernatants were harvested after 24 h of expression and used for Western blot analysis with anti-mIL2 antibody. C, CTLL-2 proliferation assay to analyze the biological activity of mIL2 encoding constructs. CTLL-2 cells were cultivated for 72 h in the presence of HEK-293T-17 supernatants harvested after 24 h of expression of mRNAs encoding the indicated proteins. CTLL-2 proliferation in the presence of recombinant IL2 served as control. Supernatants of HEK-293T-17 lipofected in the absence of mRNA (Mock) served as control. Rec. IL2: recombinant interleukin-2, mAlb: murine serum albumin, mIL2: murine interleukin-2, mIFNβ: murine interferon-β, rec: recombinant.

Figure 2:
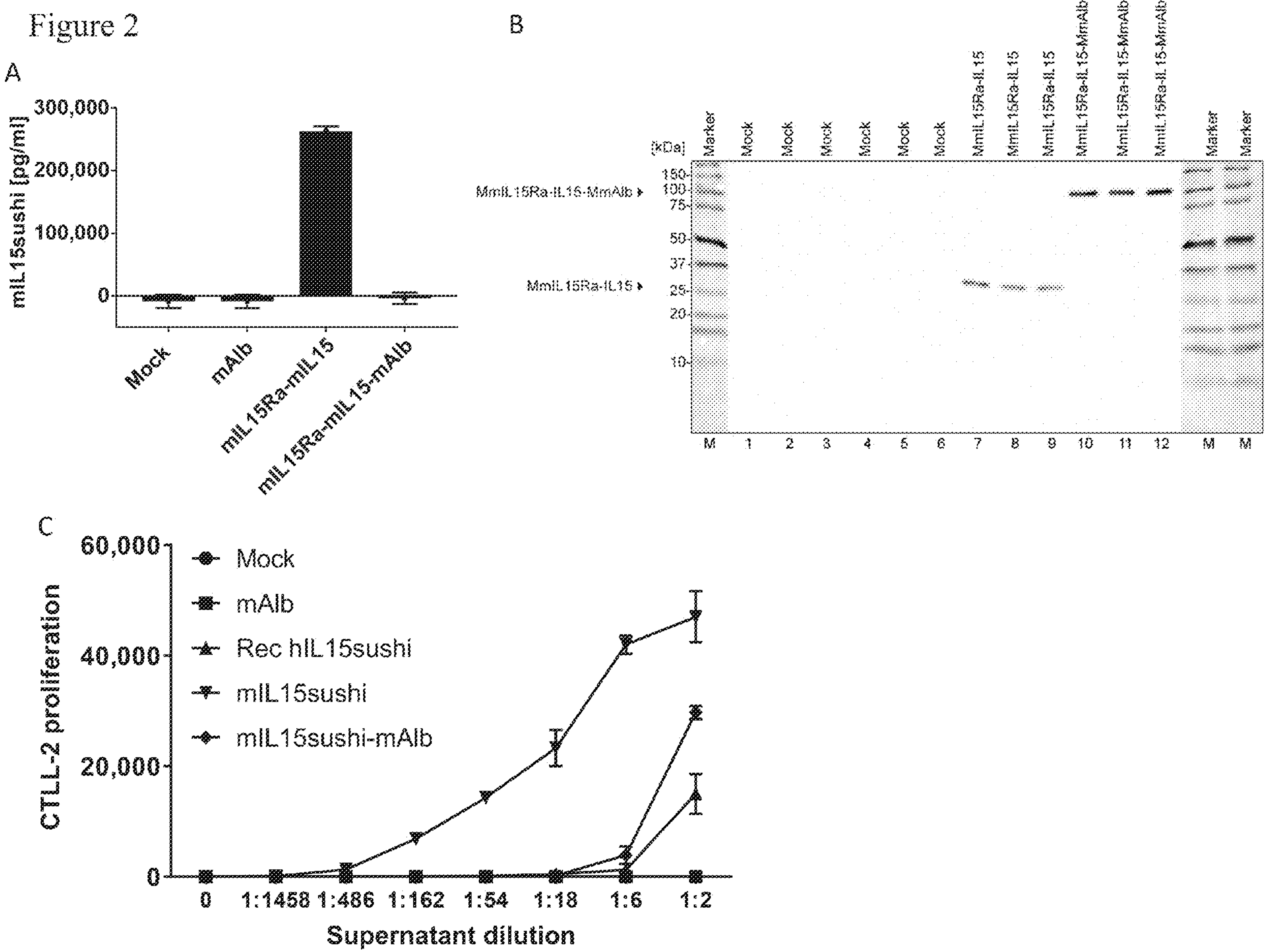

FIG. 2: Validation of mIL15sushi encoding constructs.

A, ELISA analysis of HEK-293T-17 supernatants after expression of mIL15sushi encoding constructs. HEK-293T-17 cells were lipofected with mRNAs encoding the indicated proteins or without mRNA (Mock), supernatants were harvested after 24 h of expression and used for ELISA analysis. B, Western blot analysis of HEK-293T-17 supernatants after 24 h of expression of mIL15sushi encoding mRNAs. HEK-293T-17 cells were lipofected with mRNAs encoding the indicated proteins, supernatants were harvested after 24 h of expression and used for Western blot analysis with anti-mIL15 antibody. C, CTLL-2 proliferation assay to analyze the biological activity of mIL15sushi encoding constructs. CTLL-2 cells were cultivated for 72 h in the presence of HEK-293T-17 supernatants harvested after 24 h of expression of mRNAs encoding the indicated proteins. CTLL-2 proliferation in the presence of recombinant hIL15sushi served as positive control. Supernatants of HEK-293T-17 lipofected in the absence of mRNA (Mock) served as control. Rec hIL15sushi: recombinant human IL15 fused to interleukin-15 receptor α, mAlb or MmAlb: murine serum albumin, mIL15sushi or MmIL15sushi: mouse interleukin-15 fused to interleukin-15 receptor α.

FIG. 3: Validation of mIL7 encoding constructs.

A, ELISA analysis of HEK-293T-17 supernatants after expression of mIL7 encoding constructs. HEK-293T-17 cells were lipofected with mRNAs encoding the indicated proteins or without mRNA (Mock), supernatants were harvested after 24 h of expression and used for ELISA analysis. B, Western blot analysis of HEK-293T-17 supernatants after 24 h of expression of mIL7 encoding mRNAs. HEK-293T-17 cells were lipofected with mRNAs encoding the indicated proteins, supernatants were harvested after 24 h of expression and used for Western blot analysis with anti-mIL7 antibody. C, T cell proliferation assay to analyze the biological activity of mIL7 encoding constructs. PBMCs of two different donors (donor #59 upper panel; donor #800 lower panel) cells were activated with anti-CD3 antibody (donor #59 0.05 μg/ml, donor #800 0.1 μg/ml), stained with carboxyfluorescein succinimidyl ester (CFSE) and cultivated for 96 h in the presence of HEK-293T-17 supernatants harvested after 24 h of expression of mRNAs encoding the indicated proteins. T cell proliferation in the presence of recombinant IL7 served as a positive control. T-cell proliferation was analysed by CFSE monitoring using flow cytometry after anti-CD4-PE and anti-CD8-PE-Cy7 staining. Supernatants of HEK-293T-17 lipofected in the absence of mRNA (Mock) served as control. Rec IL7: recombinant interleukin-7, mAlb or MmAlb: murine serum albumin, mIL7 or MmIL7: murine interleukin-7.

FIG. 4: Validation of mIFNβ and sec-nLUC encoding constructs.

A, ELISA analysis of HEK-293T-17 supernatants after expression of mIFNβ encoding constructs. HEK-293T-17 cells were lipofected with mRNAs encoding the indicated proteins or without mRNA (Mock), supernatants were harvested after 24 h of expression and used for ELISA analysis. B, Western blot analysis of HEK-293T-17 supernatants after 24 h of expression of mIFNβ encoding mRNAs. HEK-293T-17 cells were lipofected with mRNAs encoding the indicated proteins, supernatants were harvested after 24 h of expression and used for Western blot analysis with anti-mIFNβ antibody. C, To assess the biological activity of mIFNβ encoding constructs the capacity of the resulting mRNAs was analyzed by mIFNβ dependent upregulation of MHC class I expression in murine colon carcinoma cells (CT26). CT26 cells were cultivated for 24 h in the presence of HEK-293T-17 supernatants harvested after 24 h of expression of mIFNβ encoding mRNAs. Recombinant IFNβ served as control. Surface level of MHC class I on CT26 cells after the treatment was assessed by MHC class I staining with FITC coupled H2Kb antibody and subsequent flow cytometry analysis. D, Expression of sec-nLUC and luciferase activity of the resulting gene-products was determined in supernatants of HEK-293T-17 after 24 h of expression of sec-nLUC encoding mRNAs. The luciferase activity in supernatants after expression of mRNAs encoding the indicated proteins is plotted. Supernatants of HEK-293T-17 lipofected in the absence of mRNA (Mock) served as control. Rec IFNβ: recombinant interferon-β, mAlb: murine serum albumin, mIFNβ: murine interferon-β, mIL2: murine interleukin-2, sec-n LUC: secreted nano-luciferase.

FIG. 5: Systemic availability of cytokines is prolonged when fused to mAlb and encoded on nucleoside-modified mRNA.

C57BL/6 mice (n=3 per group and time-point) were injected i.v. with 3 μg unaltered or mAlb-fusion protein-encoding mRNA (as indicated) formulated with TransIT. Blood was retrieved and serum prepared 6, 24 and 48 h and 5 days after injection. Cytokine concentrations were determined in the blood 6, 24 and 48 h and 5 days after injection. Mean±s.e.m. mAlb: murine serum albumin, mIL2: murine interleukin-2, mIFNβ: murine interferon-β.

Figure 6:
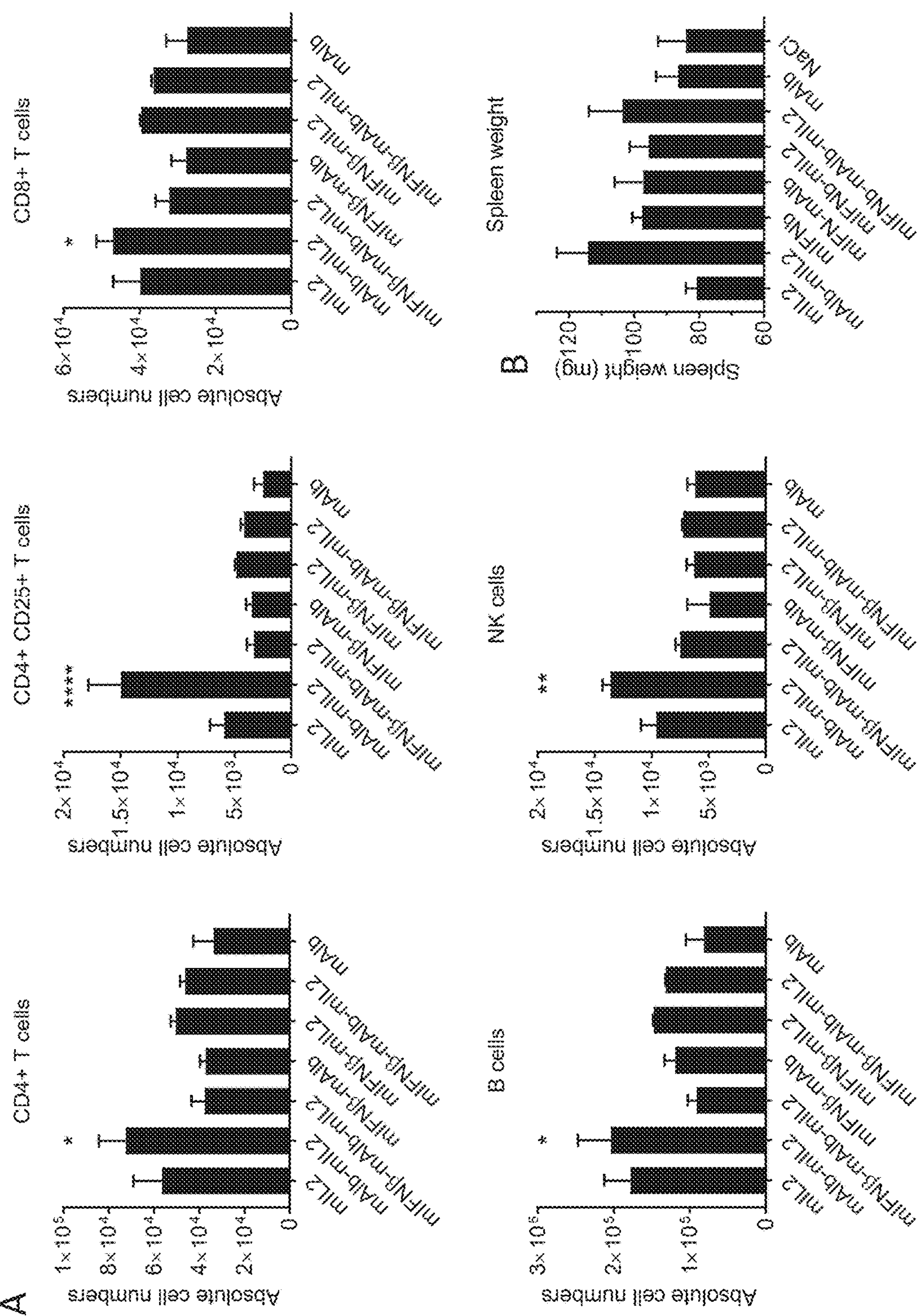

FIG. 6: mAlb-mIL2 expands immune cell subsets in the spleen.

Spleens were isolated from C57BL/6 mice treated as described in FIG. 5 on day 5 after mRNA injection and absolute cell numbers of immune cell subsets were determined by flow cytometry. Depicted are absolute cell numbers of T cell subsets, B cells and NK cells per spleen (A), and spleen weights (B). Statistical significance was determined using a one-way ANOVA followed by Dunnett's multiple comparison test (see Table 1). Mean±s.e.m.

Figure 7:
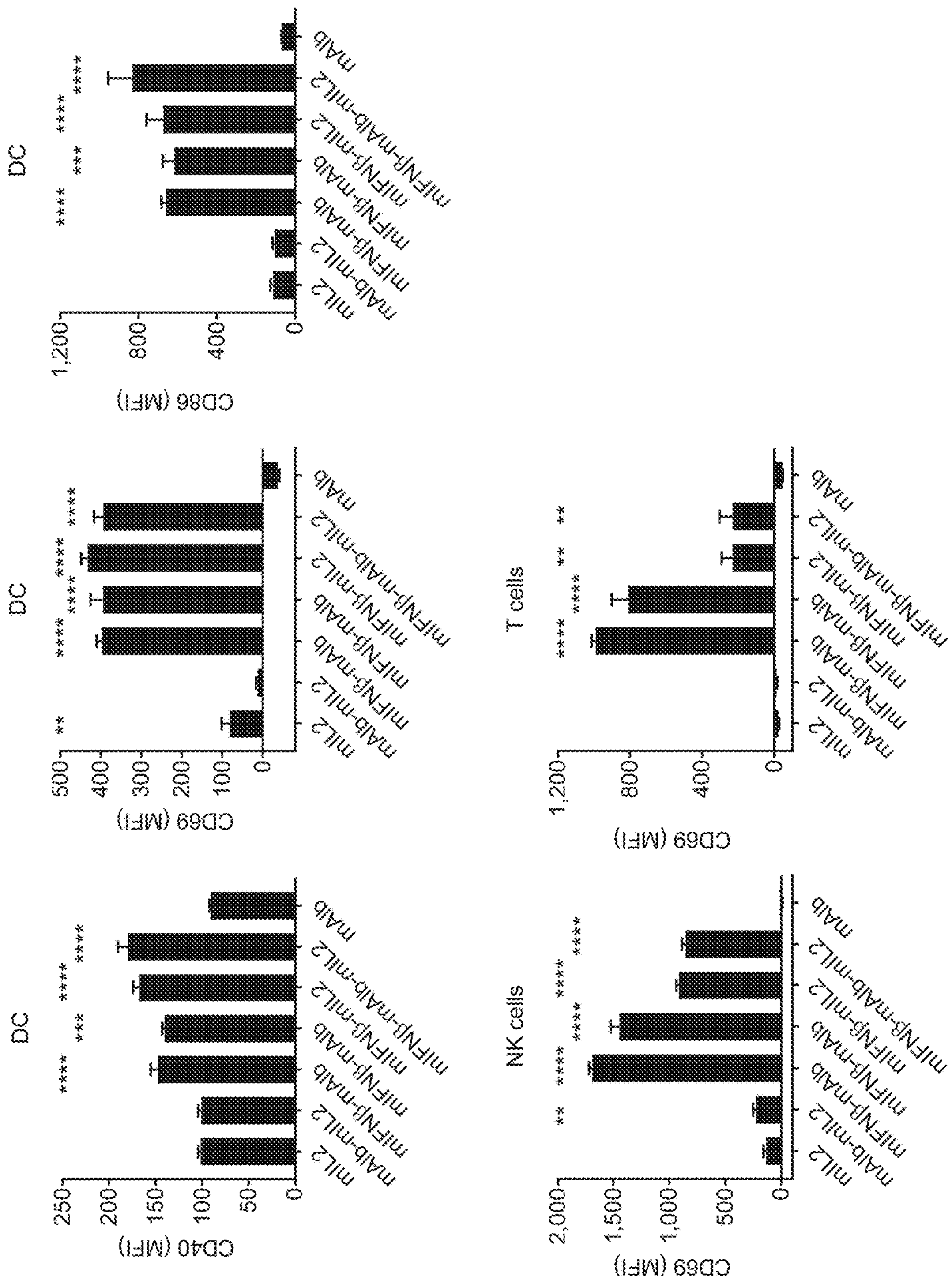

FIG. 7: mIFNβ-mAlb activates immune cell subsets in the spleen.

Figure 24:
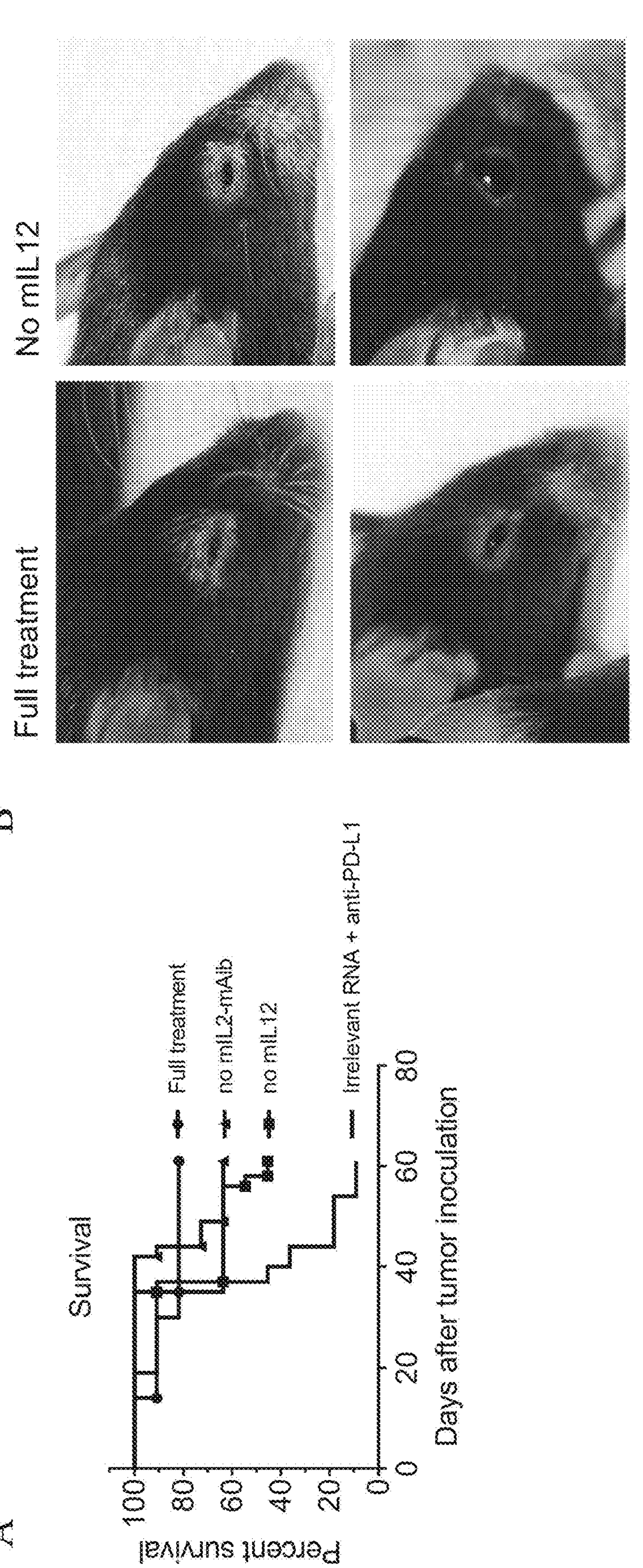

Spleens were isolated from C57BL/6 mice treated as described in FIG. 5 24 h after mRNA injection and activation status of immune cell subsets (CD40, CD69 and CD86 expression) was determined by flow cytometry. Depicted are median fluorescence intensities (MFI). Statistical significance was determined using a one-way ANOVA followed by Dunnett's multiple comparison test (see Table 2). Mean±s.e.m.

Figure 8:
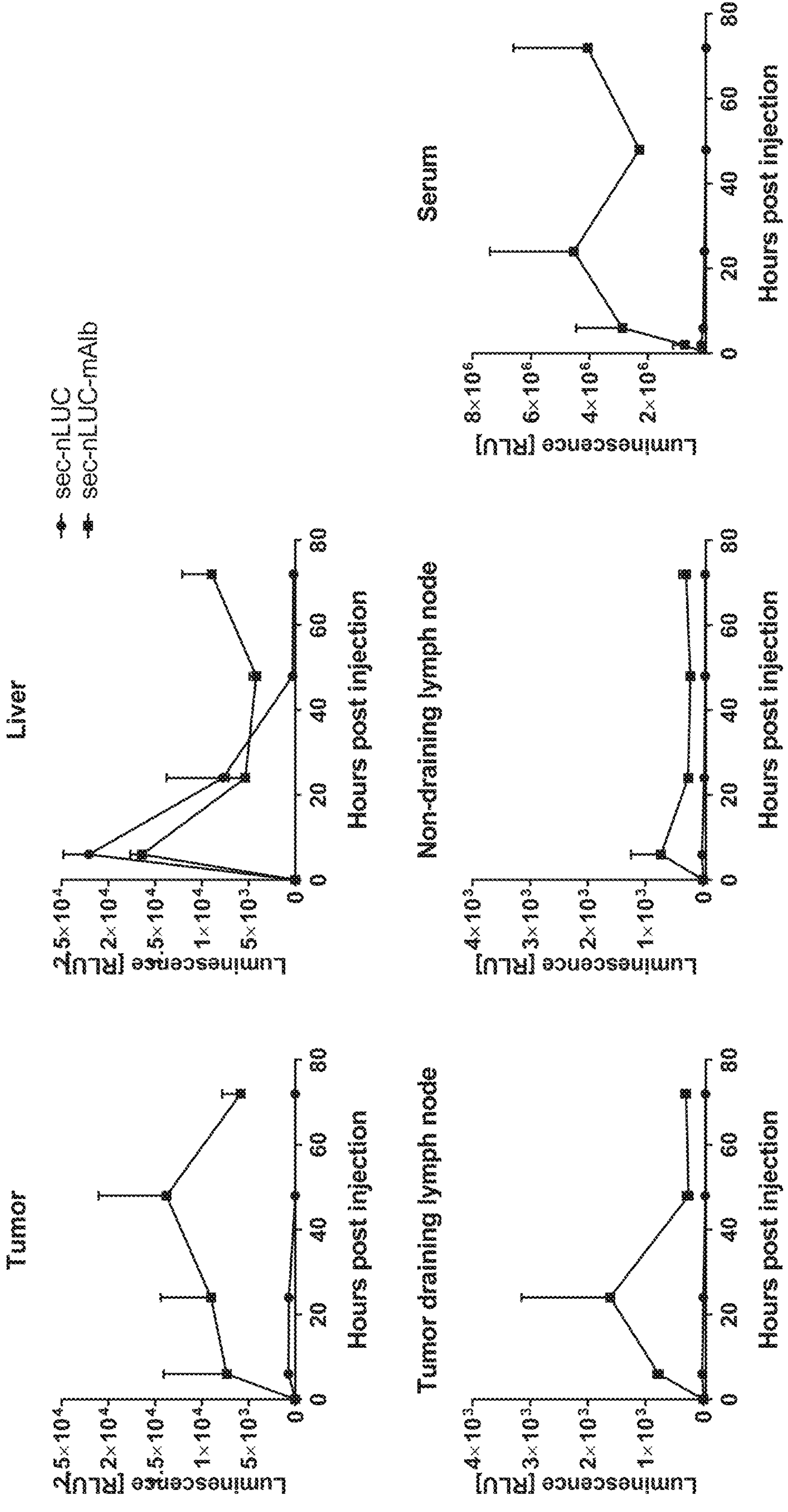

FIG. 8: mAlb fusion enhances and prolongs protein availability in the blood, tumor and tumor-draining lymph node.

BALB/c mice (n=3 mice per group and time-point) were inoculated with $5\times10^5$ CT26 tumor cells in 100 μl PBS s.c. and injected i.v. on day 24 with 3 μg sec-nLUC, sec-nLUC fused to mAlb (sec-nLUC-mAlb) formulated with TransIT, or remained untreated (control). Serum was prepared 2, 6, 24, 48 and 72 h, and tissues harvested 6, 24, 48 and 72 h after injection. Bioluminescence intensity was quantified from 50 μl serum or 30 μg total protein derived from tissue lysates. Data received from the control group served as baseline at time-point 0. Mean±s.e.m.

Figure 9:
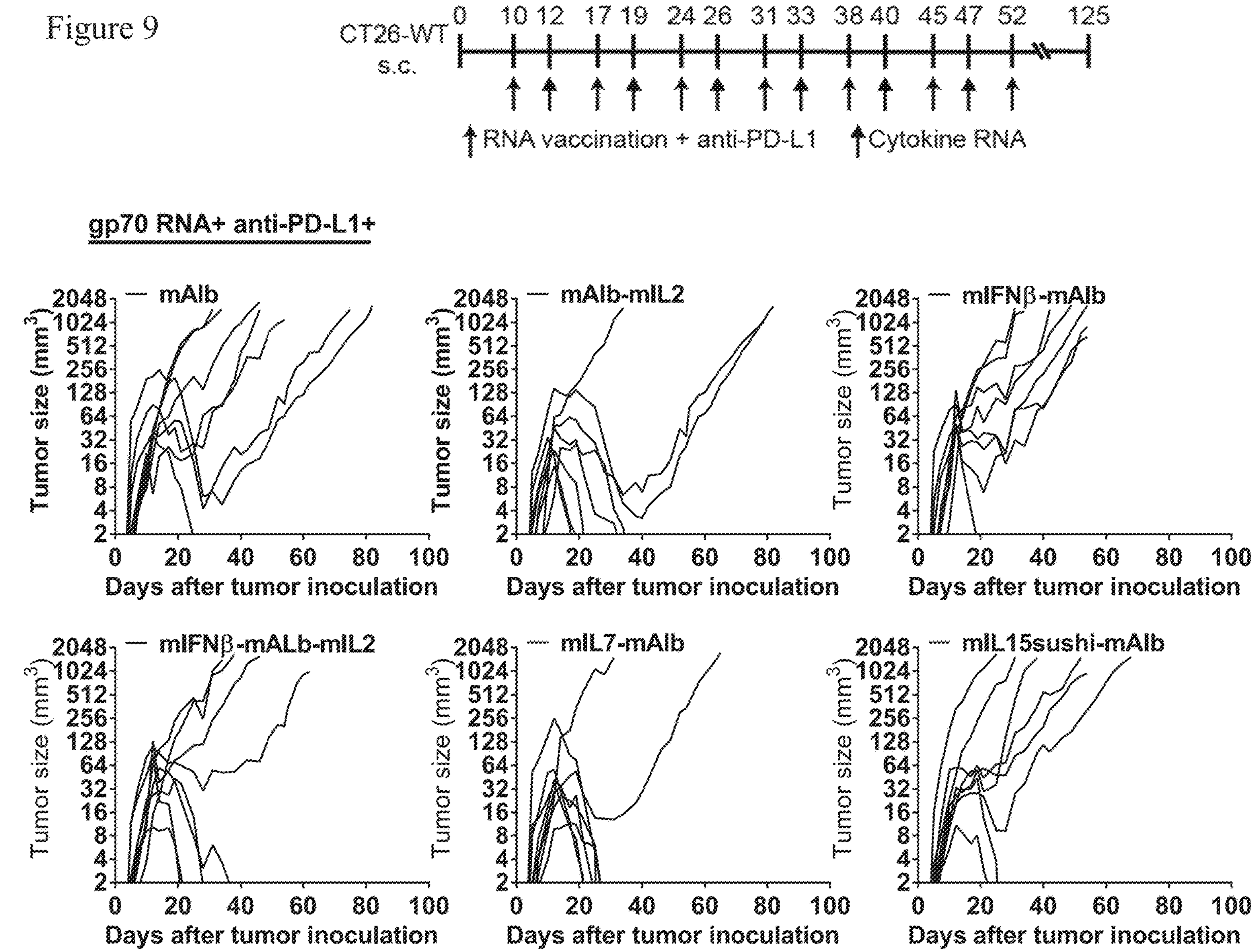

FIG. 9: mAlb-mIL2 and mIL7-mAlb potently boosts tumor control of mRNA vaccination and PD-L1 blockade.

BALB/c mice (n=8 per group) were injected subcutaneously with $5\times10^5$ CT26-WT tumor cells in 100 μl PBS s.c. Ten days later, mice were treated with gp70 mRNA lipoplex vaccination (20 μg i.v.) and an anti-PD-L1 blocking antibody (200 μg i.p. on first treatment, then 100 μg i.p.). Two days later, 1 μg nucleoside-modified mRNA encoding various cytokines (as indicated in the figure) was injected i.v. in a liver targeting nanoparticle formulation. As control, murine albumin (mAlb) RNA was administered. The treatment schedule was repeated weekly as depicted in the upper panel. Growth curves of individual mice are shown. mIL2: murine Interleukin-2, mIFNβ: murine Interferon-β, mIL7: murine Interleukin-7, mIL15sushi: mouse Interleukin-15 fused to Interleukin-15 receptor α.

Figure 10:
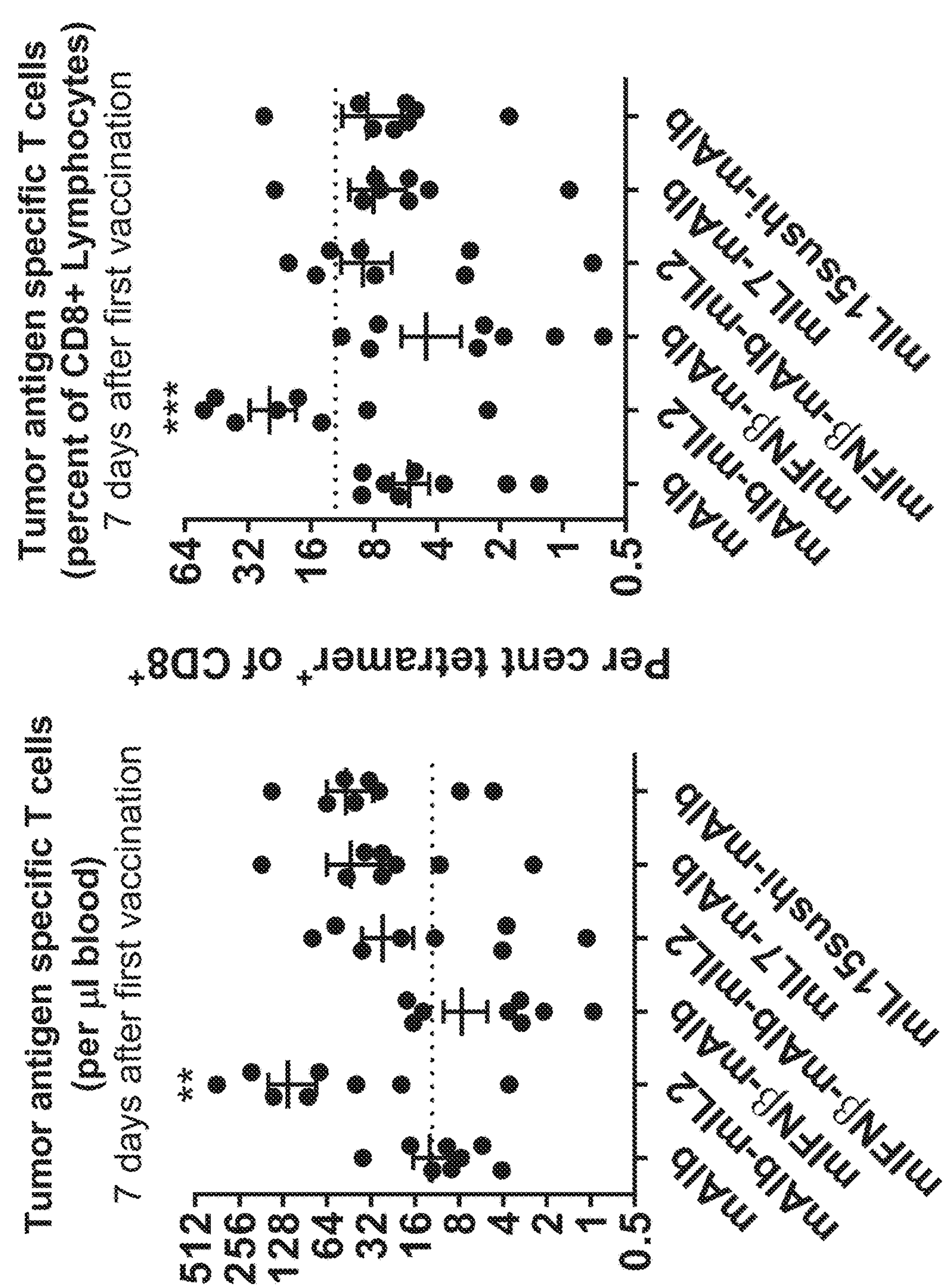

FIG. 10: mAlb-mIL2 readily increases vaccine induced T-cell responses.

CT26-WT tumor bearing mice depicted in FIG. 9 were analyzed by flow cytometry for gp70 AH1 tetramer+ CD8+ T cells in blood 7 days after the first treatment (day 17 after tumor inoculation). Absolute numbers per μl blood (left) and the fraction of tetramer+ cells among CD8+ T cells (right) are depicted. Statistical significance was determined using a one-way ANOVA followed by Dunnett's multiple comparison test. Mean±s.e.m.

Figure 11:
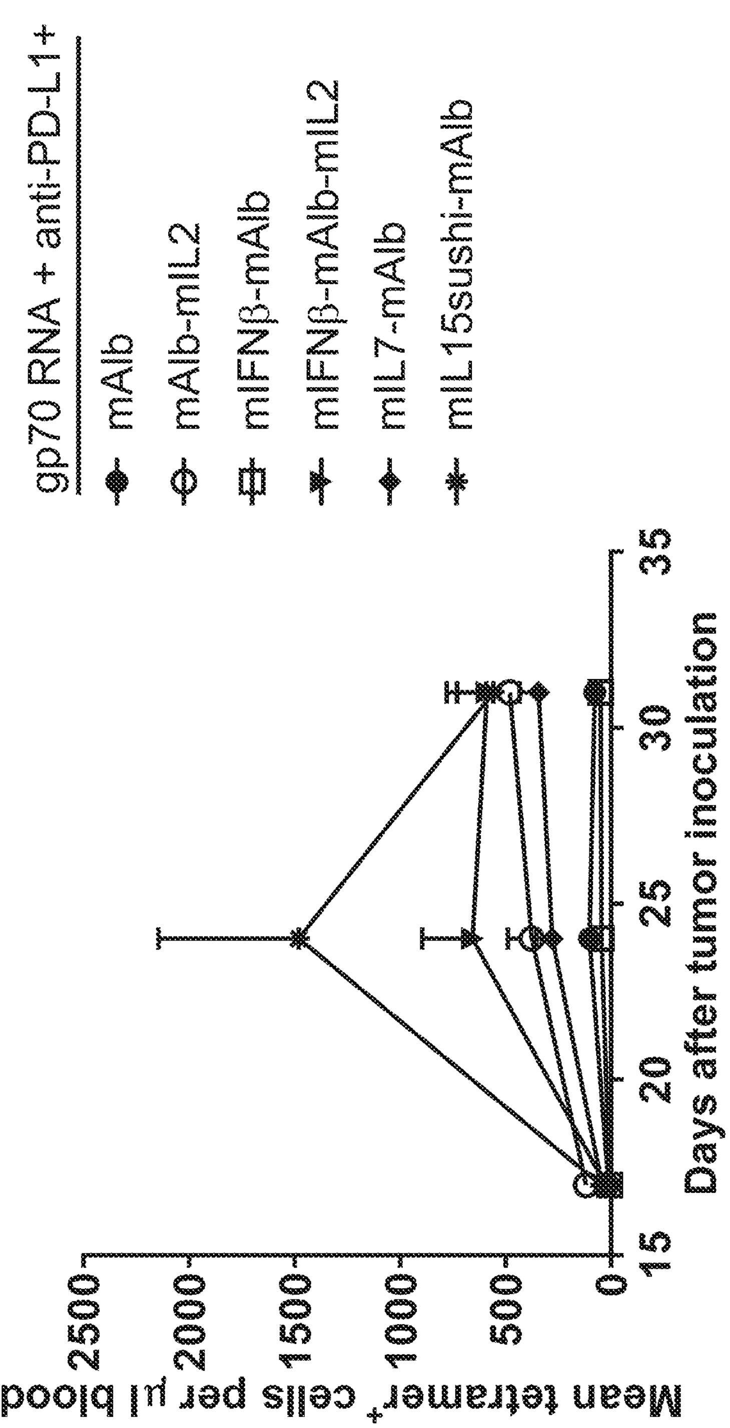

FIG. 11: mAlb-mIL2 and mIL7-mAlb maintain high titers of antigen specific T-cells.

Depicted is the number of gp70 AH1 tetramer+ CD8+ cells per μl blood at day 17, 24 and 31 after tumor inoculation of mice introduced in FIG. 9. Mean±s.e.m.

Figure 12:
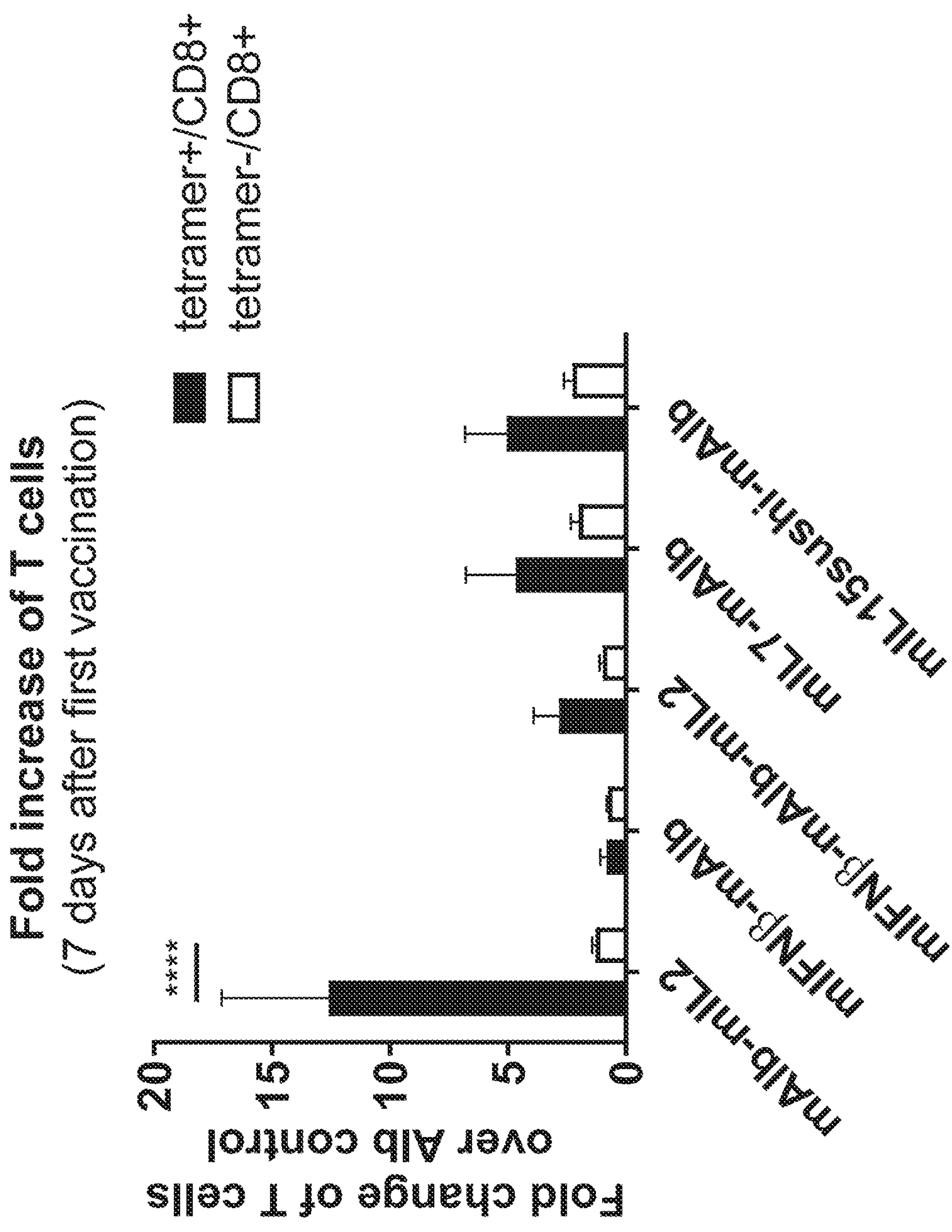

FIG. 12: mAlb-mIL2 expands predominantly tumor antigen specific T cells.

Fold increase over the median CD8+ tetramer positive or CD8+ tetramer negative T-cell count of mAlb treated control animals introduced in FIG. 9 seven days after the first treatment is shown. Statistical significance was determined using a one-way ANOVA followed by Sidaks's multiple comparison test. Mean±s.e.m.

Figure 13:
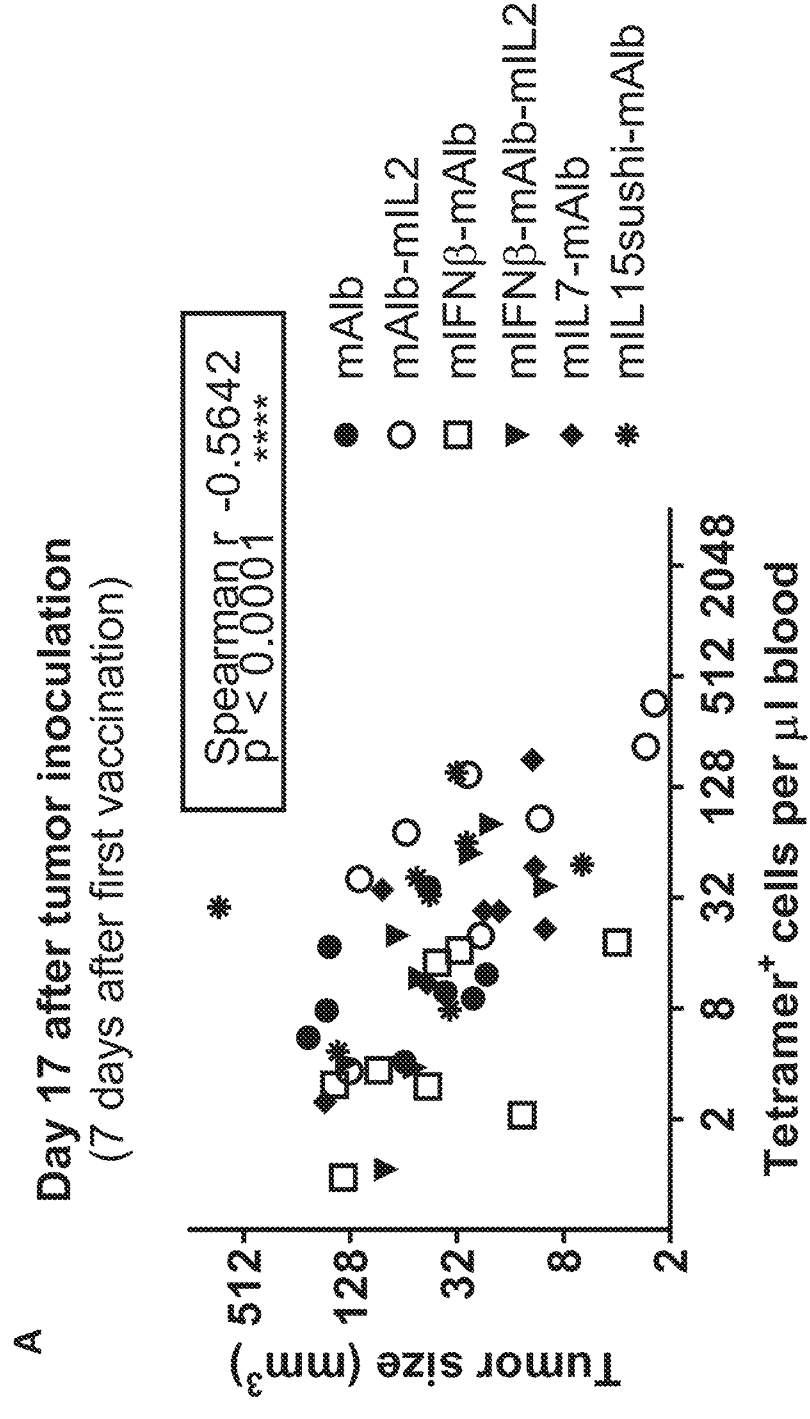
Figure 13:
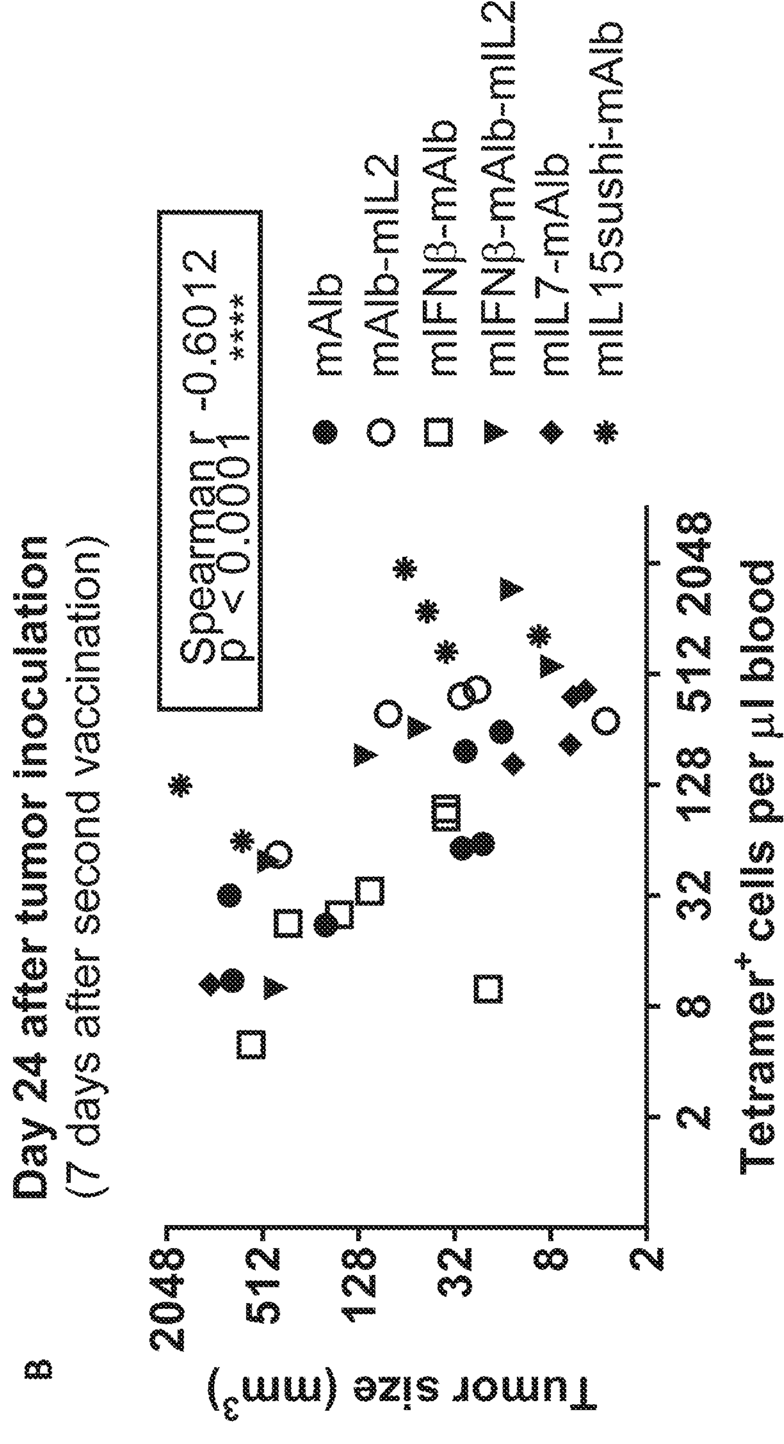
Figure 13:
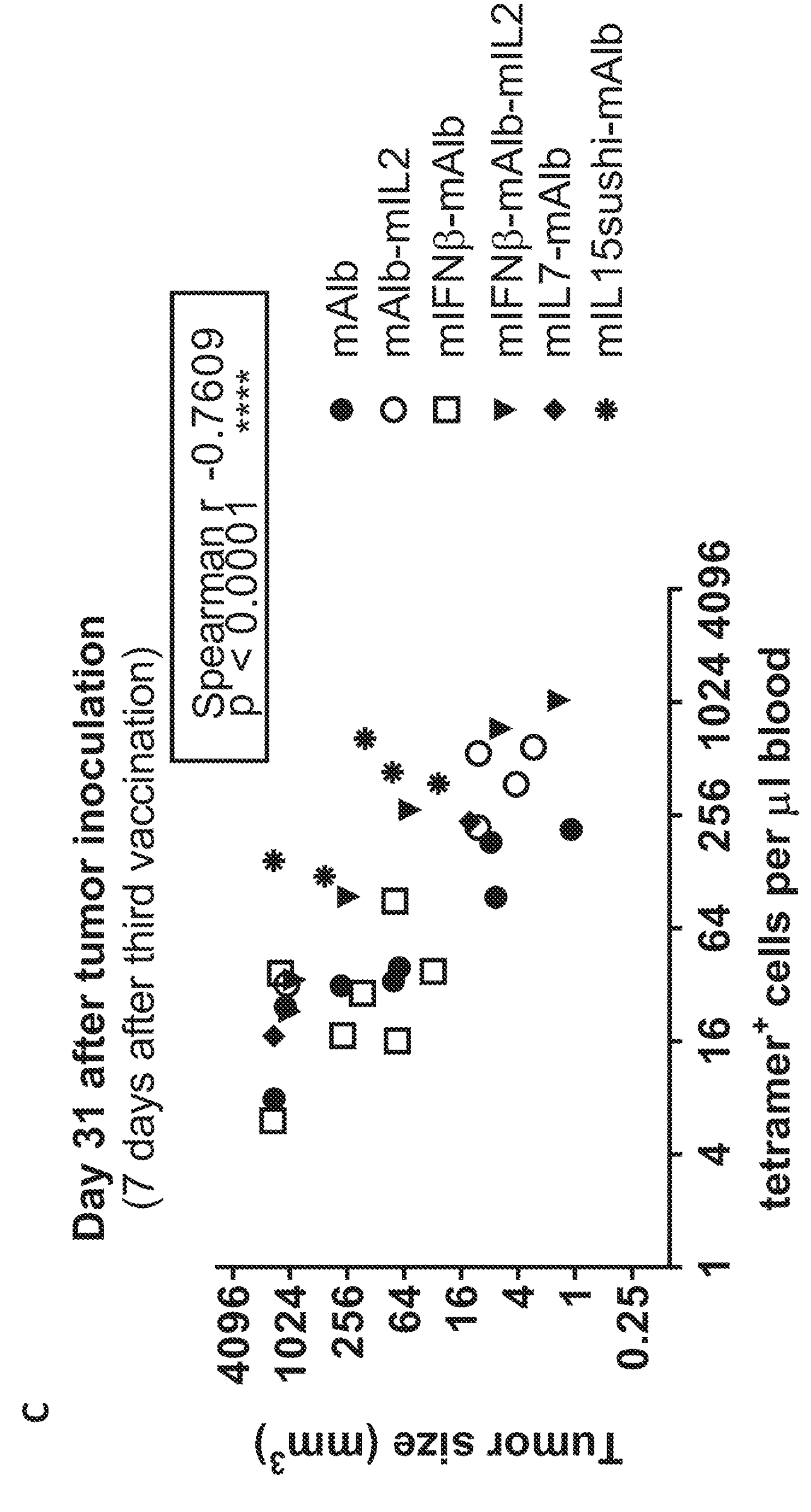

FIG. 13: Tumor size inversely correlates with tumor-antigen specific T cell titers.

The number of tetramer positive cells per μl blood from mice introduced in FIG. 9 is plotted against tumor size on day 17 (A), 24 (B) and 31 (C). Significance was determined based on Spearman's rank correlation coefficient.

FIG. 14: IL7-mAlb strongly increases CD4+ T cell numbers while decreasing the fraction of CD4+ CD25+ FoxP3+ regulatory T cells.

Quantification of CD4+ (absolute number) and CD4+ CD25+ FoxP3+ (fraction of CD4+ T cells) T cells by flow cytometry. Blood of mice (introduced in FIG. 9) was analyzed on day 31 after tumor inoculation. Significance was determined using a one-way ANOVA followed by Dunnett's multiple comparison test. Mean±s.e.m.

Figure 15:
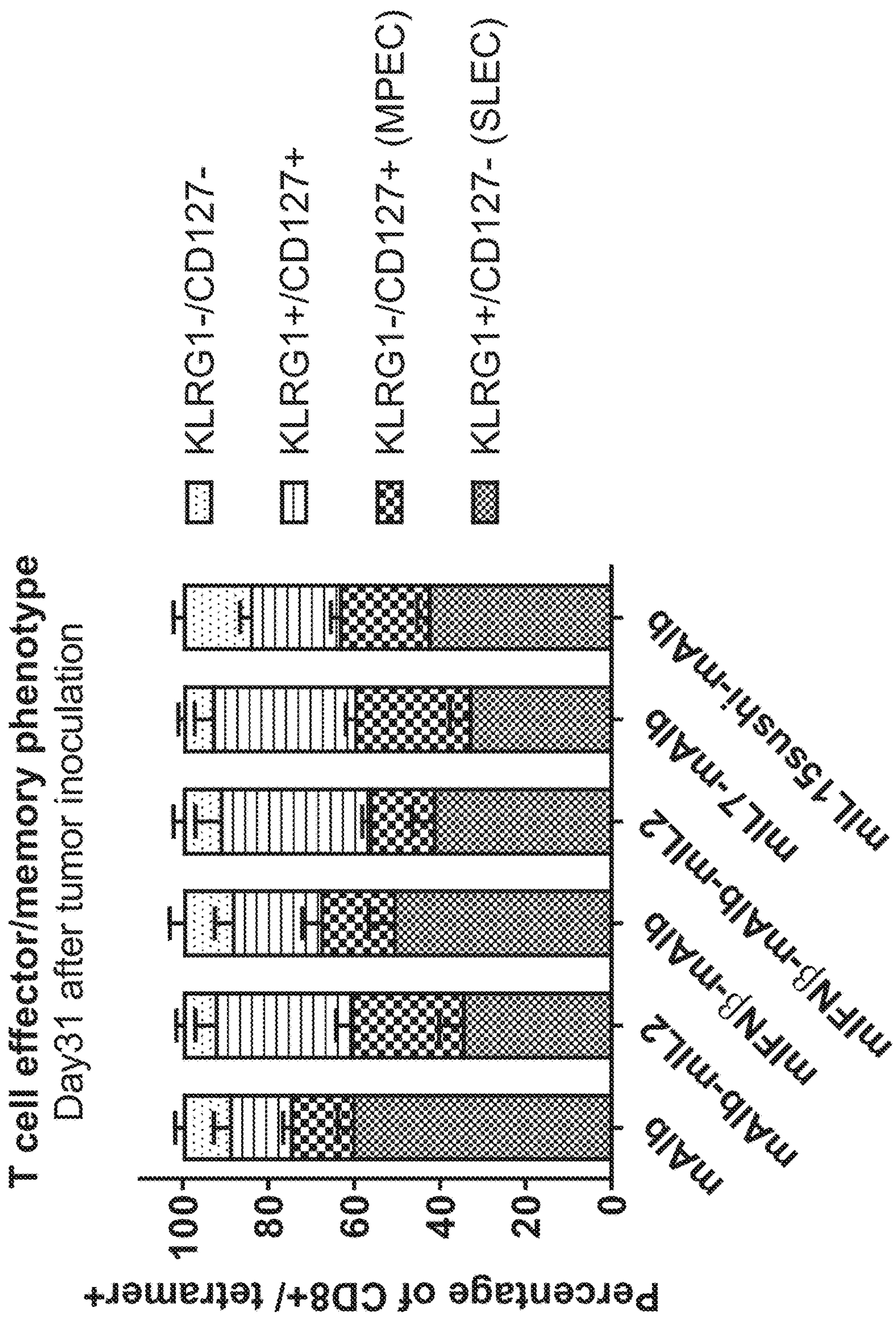

FIG. 15: mIL7-mAlb and mAlb-mIL2 reduce the fraction of antigen specific short lived effector cells for the sake of long lived CD127+ memory precursor cells.

31 days after tumor inoculation blood of mice introduced in FIG. 9 was analyzed for markers of short lived effector cells (SLEC, KLRG1+/CD127−) and CD127+ cells (memory precursor effector cells; MPEG, KLRG1−/CD127+) (KLRG1+/CD127+). CD127: interleukin-7 receptor, KLRG-1: Killer cell lectin-like receptor subfamily G member 1. Two-way ANOVA analysis followed by Dunnett's multiple comparisons test revealed a significant reduction of SLECs and increase in CD127+ cells by mAlb-mIL2 and mIL7-mAlb (see Table 3).

Figure 16:
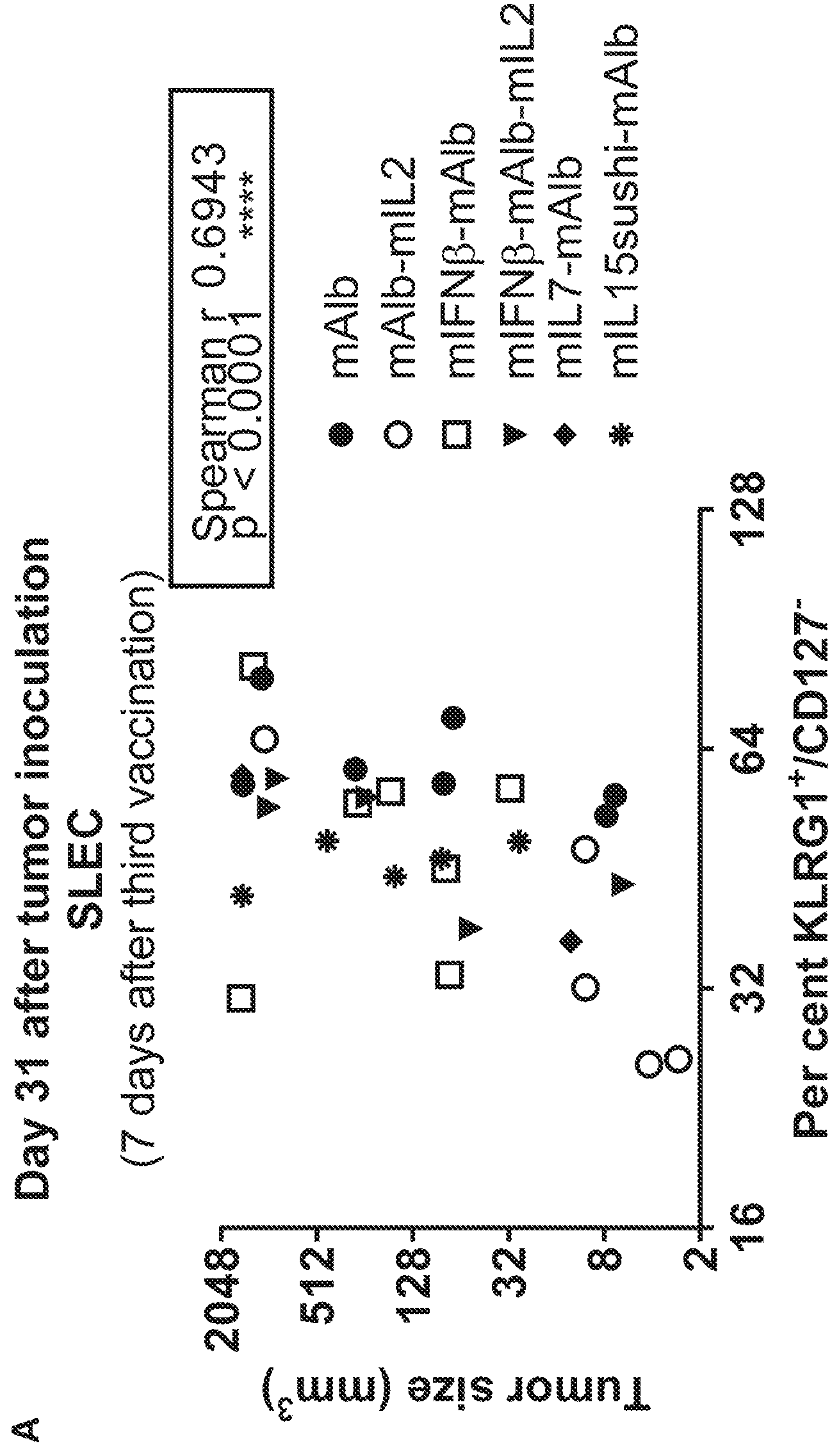
Figure 16:
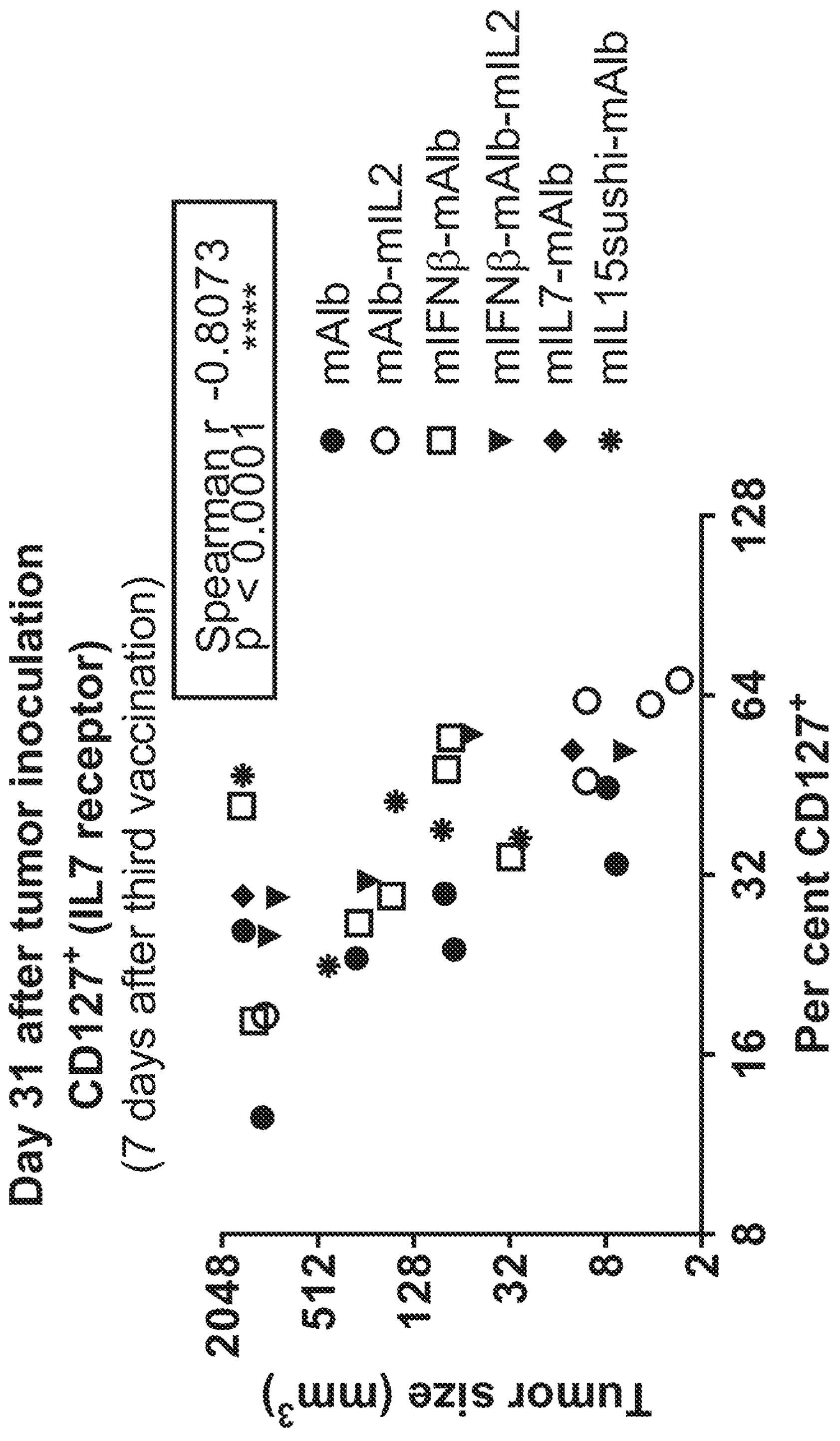

FIG. 16: Short lived effector-cell frequency positively correlates with tumor volume whereas a high CD127+ antigen specific T-cells frequency goes along with a reduced tumor size.

Percent SLEC (A) or CD127+ (B) cells among gp70 AH1 tetramer+ CD8+ cells are plotted against tumor size on day 31 from mice introduced in FIG. 9. Significance was determined based on Spearman's rank correlation coefficient.

Figure 17:
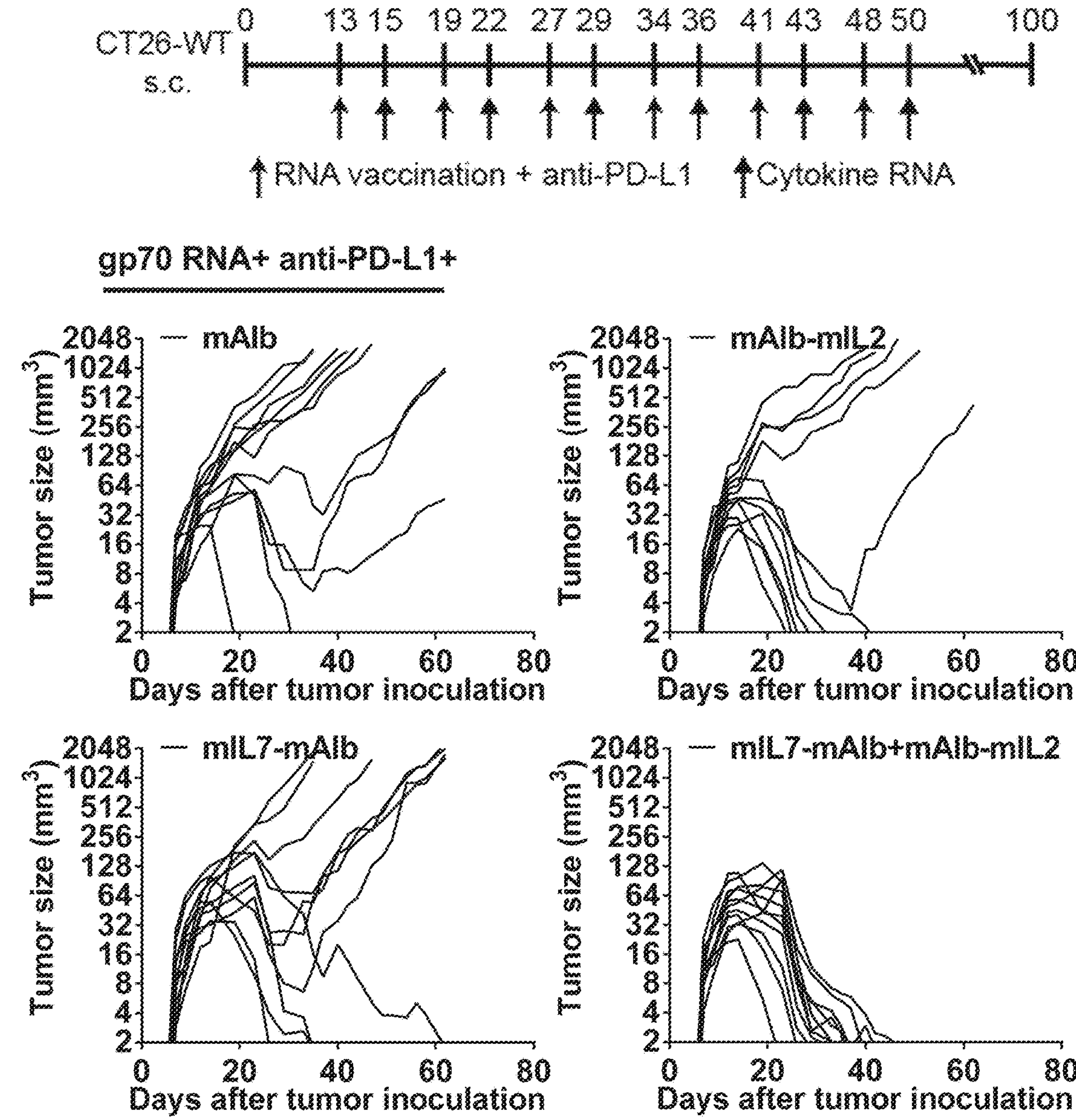

FIG. 17: Combination of mAlb-mIL2 and mIL7-mAlb with mRNA vaccination and PD-L1 blockade results in complete tumor eradication.

CT26-WT tumor bearing mice (n=11) were treated as described in FIG. 9. Mice received weekly gp70 RNA-LPX and anti-PD-L1 blocking antibody injections. After two days, nucleoside-modified mRNA encoding mAlb-mIL2, mIL7-mAlb or both (1 μg each) was administered. Treatment was started at day 13 after tumor inoculation (see upper panel). Growth curves of individual mice are shown.

Figure 18:
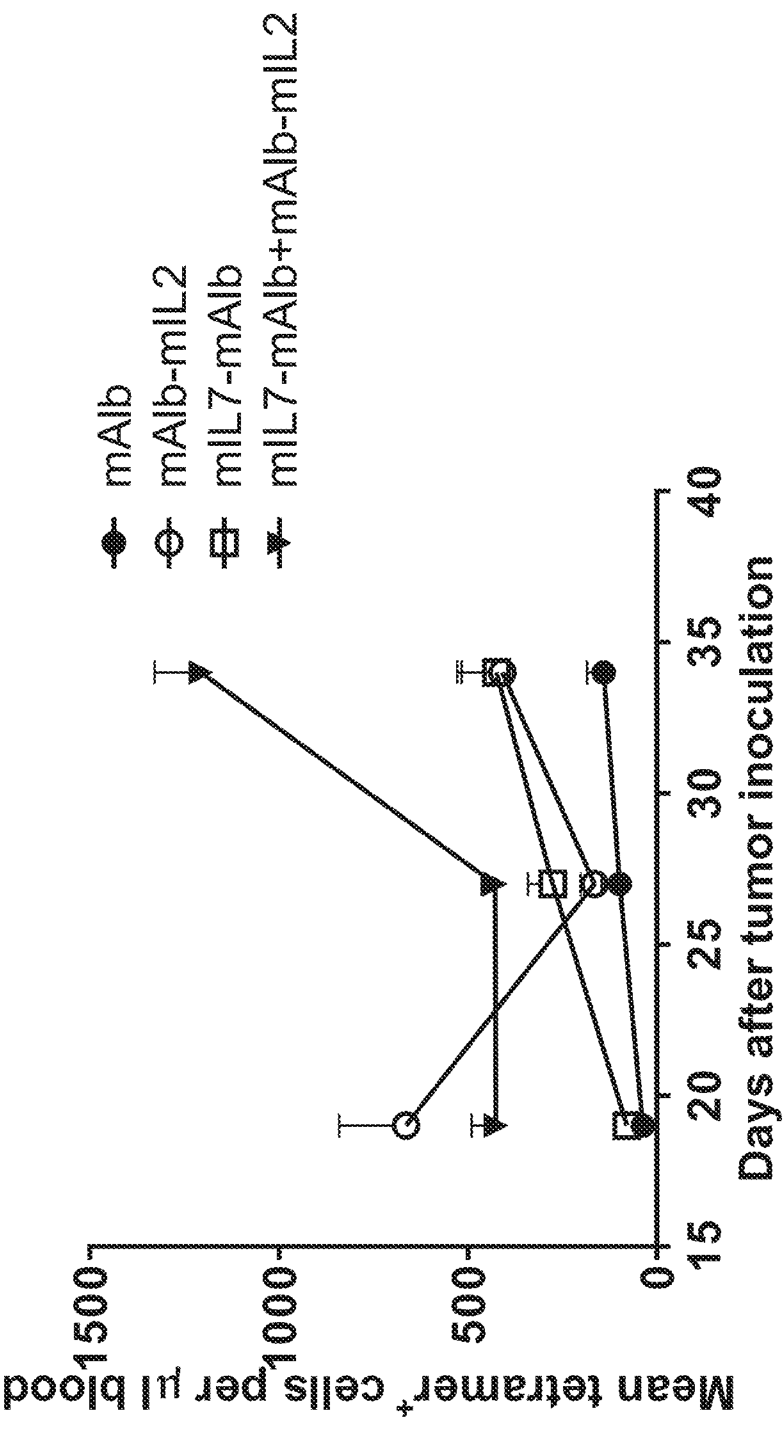
Figure 18:
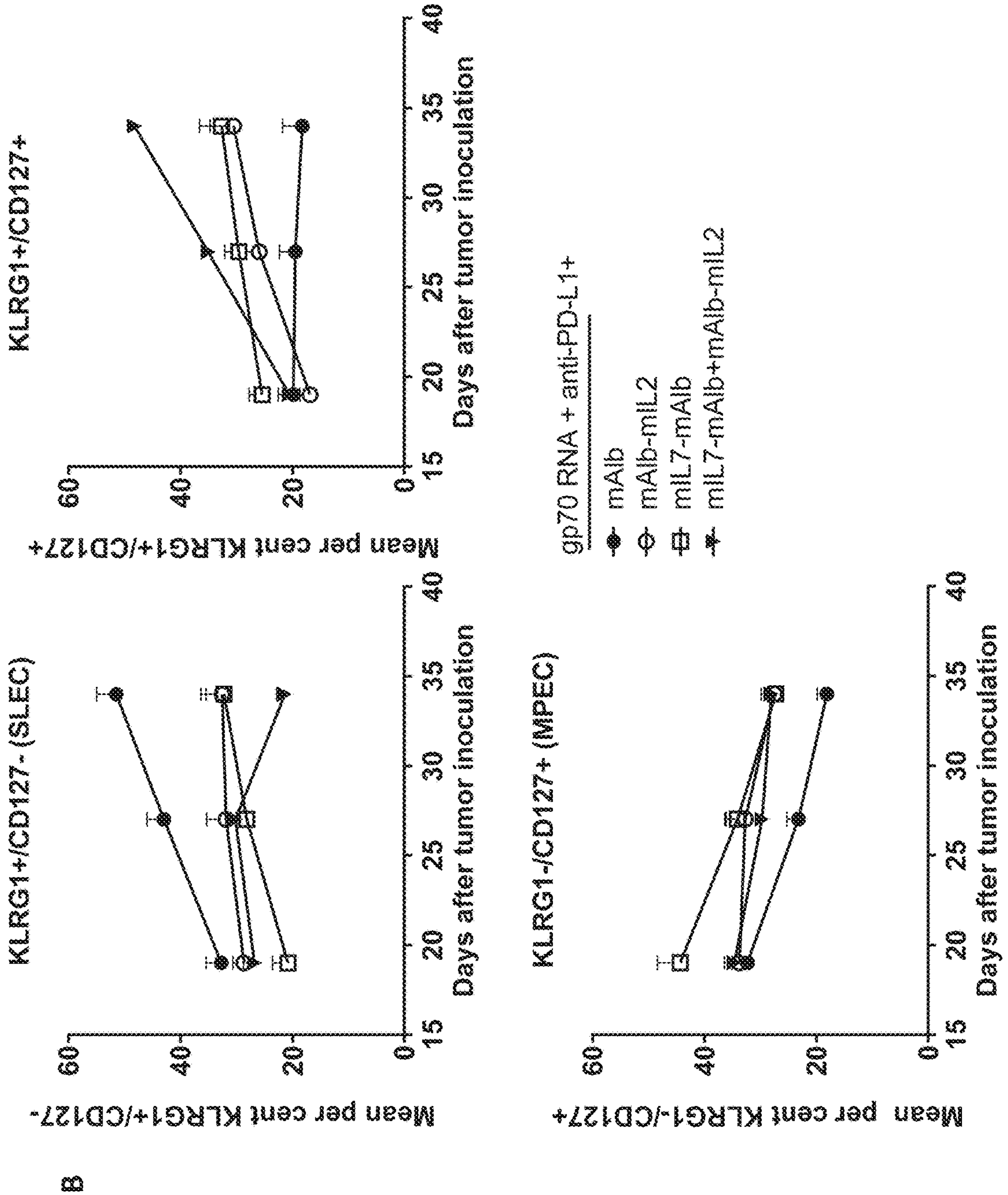

FIG. 18: mAlb-mIL2 and mIL7-mAlb synergize in boosting long lasting vaccine induced T-cell responses.

Blood of mice depicted in FIG. 17 was analyzed by flow cytometry for gp70 AH1 tetramer+ CD8+ T cells (A) and their expression of KLRG1 and CD127 (B) on day 19, 27 and 34 after tumor inoculation. Mean±s.e.m.

Figure 19:
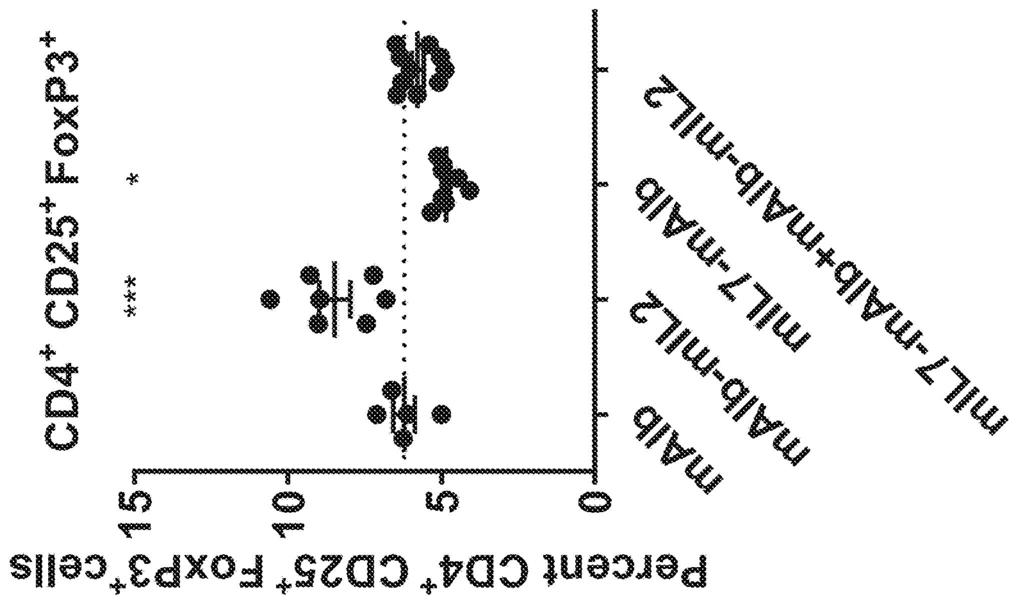

FIG. 19: mIL7-mAlb normalizes protumoral regulatory T-cell numbers increased by mALb-mIL2.

On day 57 after tumor inoculation remaining mice depicted in FIG. 17 were analyzed for the fraction of CD4+ CD25+ FoxP3+ regulatory T cells among CD4+ T cells in blood. Significance was determined using a one-way ANOVA followed by Dunnett's multiple comparison test. Mean±s.e.m.

Figure 20:
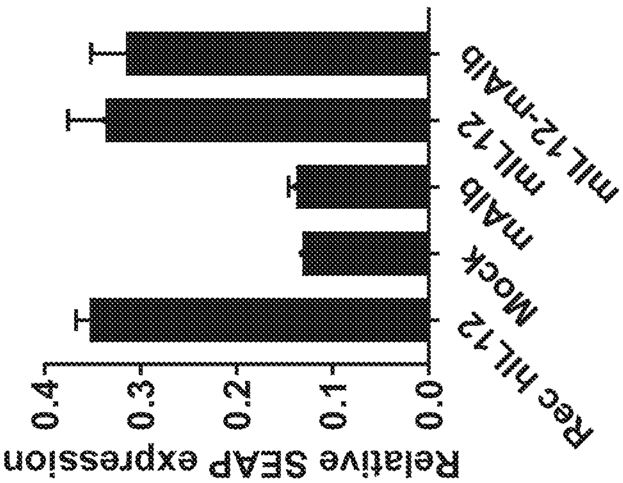

FIG. 20: Validation of mIL12 encoding constructs

HEK-Blue IL12 luciferase assay to analyze the biological activity of mIL12 encoding mRNAs. HEK-Blue IL12 cells were cultivated for 24 h in the presence of HEK-293T-17 supernatants harvested after 24 h of expression of mRNAs encoding the indicated proteins. Recombinant human IL12 served as control. Supernatants of HEK-293T-17 lipofected in the absence of mRNA (Mock) served as control. Rec hIL12: recombinant human interleukin-12, mAlb: murine serum albumin, mIL12: murine interleukin-12, SEAP: secreted embryonic alkaline phosphatase.

Figure 21:
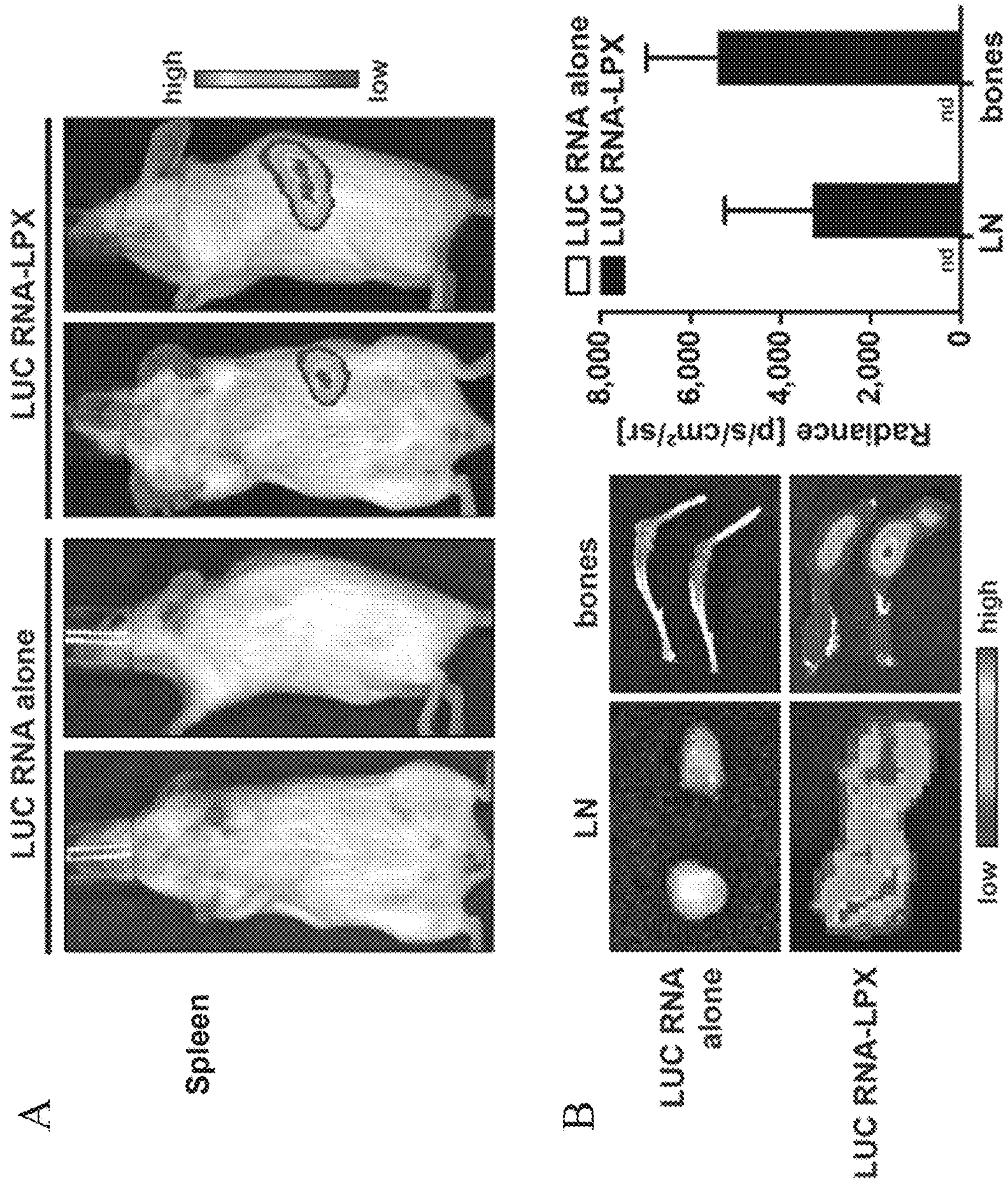

FIG. 21: Expression of mRNA encoded proteins confined to DCs in secondary lymphoid organs.

A, BALB/c mice (n=5 per group) were injected i.v. with 20 μg LUC-encoding RNA-LPX or LUC mRNA alone and bioluminescence was determined 6 h after injection by in vivo imaging. B, Inguinal lymph nodes and bones were isolated from BALB/c mice (n=5 per group) 24 h after injection of 100 μg LUC RNA-LPX or LUC mRNA alone and bioluminescence was quantified by ex vivo imaging. C, CD11c-DTR mice (n=3 per group) were treated i.p. with 4 ng/g body weight DT 12 h prior to injection of 100 μg LUC RNA-LPX and bioluminescence was quantified in the spleen and inguinal lymph nodes in vivo, and of bone marrow single-cell suspensions by ex vivo LUC assay 6 h after injection. Data corrected for background bioluminescence of untreated organs or cells. Mean±SD. DT: diphtheria toxin; LUC: luciferase; BM: bone marrow; LN: lymph node. Data derived in part from (Kranz, L. M. et al. Nature 534, 396-401 (2016)) with permission from Lena Kranz.

Figure 22:
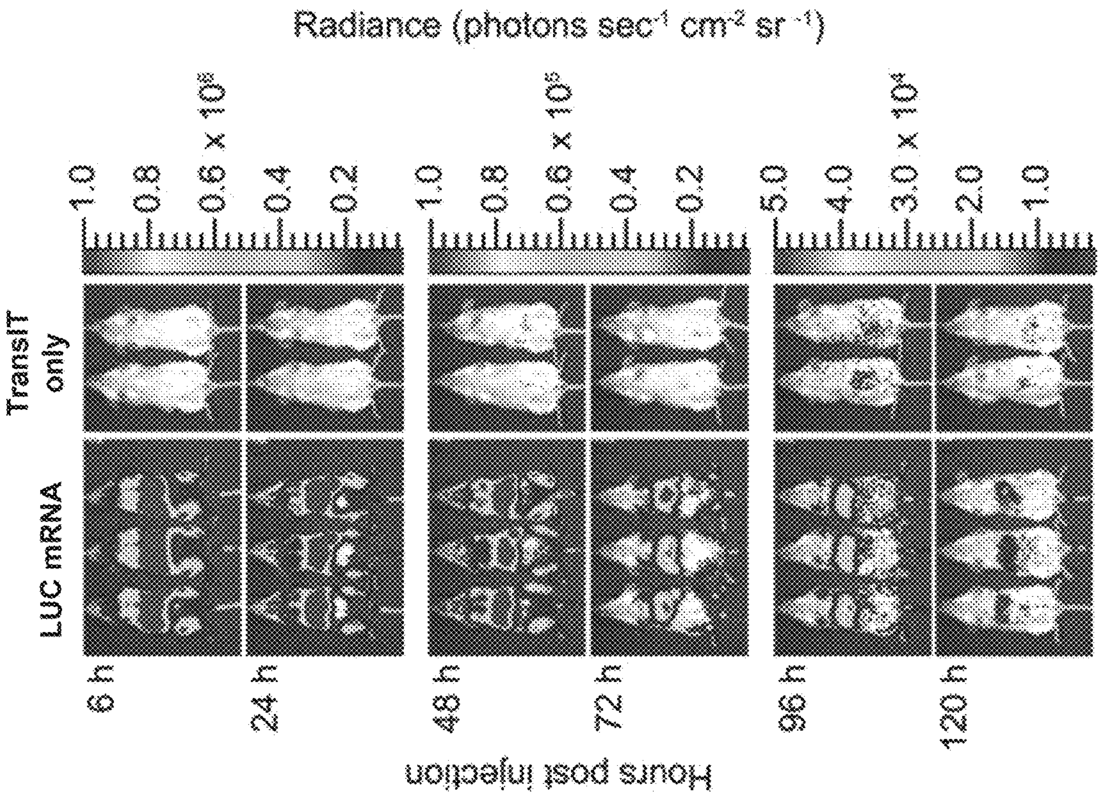

FIG. 22: Expression of mRNA encoded proteins confined to the liver.

BALB/c mice were injected i.v. with 5 μg polymer/lipid formulated LUC mRNA (n=3) or with the polymer/lipid (TransIT) alone (n=2) and bioluminescence was determined at the timepoints indicated after injection by in vivo imaging. LUC: luciferase. Data derived from (Stadler, C. et al Nat Med 23(7):815-817 (2017)) with permission from Katalin Kariko.

Figure 23:
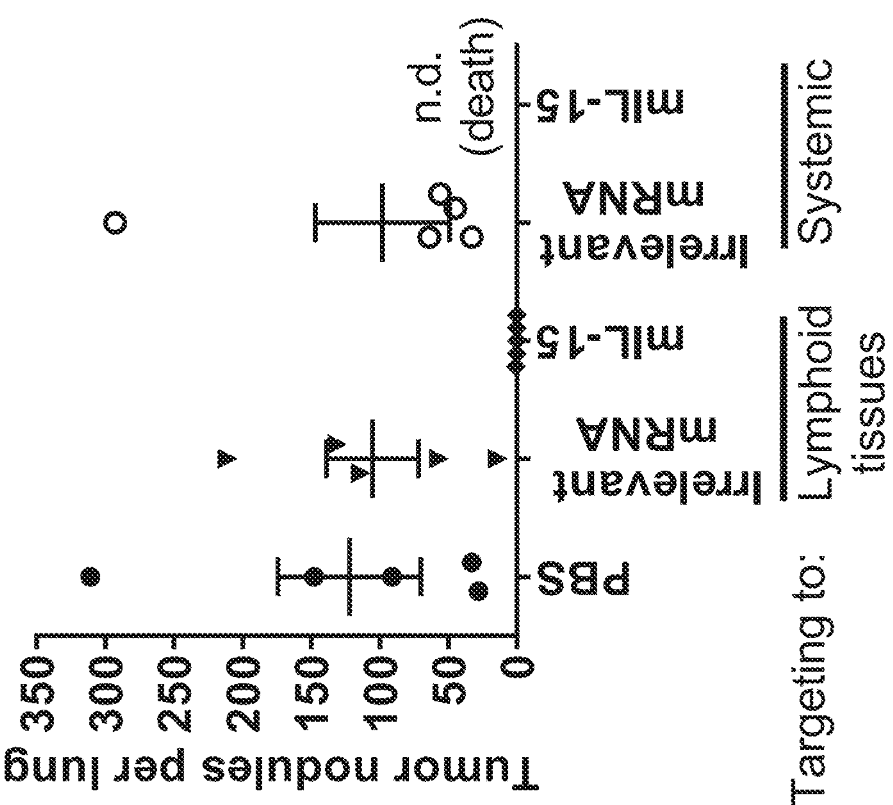

FIG. 23: High efficacy without toxicity of mIL15 encoding mRNA targeted to secondary lymphoid organs.

BALB/c mice (n=5 per group) were injected i.v. with $4\times10^5$ CT26-B2MKO tumor cells (CT26 cells that lack functional MHC class I on their surface) in 200 μl PBS. Four and seven days later, mice were treated with mIL15 mRNA either delivered via RNA-LPX into secondary lymphoid organs (40 μg) or into the liver (3 μg i.v.) for systemic availability. As control, the same amount of LUC encoding irrelevant mRNA as well as PBS was used. 12 days after tumor inoculation lungs were harvested and tumor nodules were counted. All mice that received liver targeted (systemic) mIL15 mRNA died upon the second treatment and could not be analyzed (n.d., not determined). mIL15: mouse IL15 fused to mouse IL15 receptor α.

FIG. 24: Combination of IL12 and IL2 targeted according to physiological function boosts tumor-specific T cell therapy and therapeutic efficacy C57BL/6 mice (n=11 per group) were inoculated with $3\times10^5$ B16F10 melanoma cells. Eight days after tumor inoculation mice were stratified according to tumor size and received either an RNA-LPX based T-cell vaccine i.v. containing 10 μg of the differentiation antigen tyrosinase related protein-2 ($TRP2_{180-188}$) as well as 10 μg of the MHC class II-restricted neoantigen B16_M30[9], or irrelevant mRNA (20 μg vaccine backbone without insert). All mice received 200 μg (consecutive treatments with 100 μg) of an anti-PD-L1 antibody (clone 6E11, mIgG2A, L234A, L235A, P329G; Genentech) in 200 μl PBS i.p. Mice were co-injected i.v. with 3 μg (1 μg from fourth treatment on) mIL12 mRNA or irrelevant mRNA delivered as RNA-LPX (delivery to secondary lymphoid organs). Roughly 48 h later, 1 μg mRNA encoding mIL2-mAlb or 1 μg mAlb control formulated with TransIT (delivery to liver for systemic availability) was injected i.v. The treatment schedule was repeated weekly for seven weeks. Depicted are survival of mice (A) and representative mice showing signs of vitiligo around the eyes in response to treatment with mRNA vaccination with anti-PD-L1 antibody and mIL12 combined with mAlb-mIL2, mIL12 alone or mAlb-mIL2 alone (B).

Figure 25:
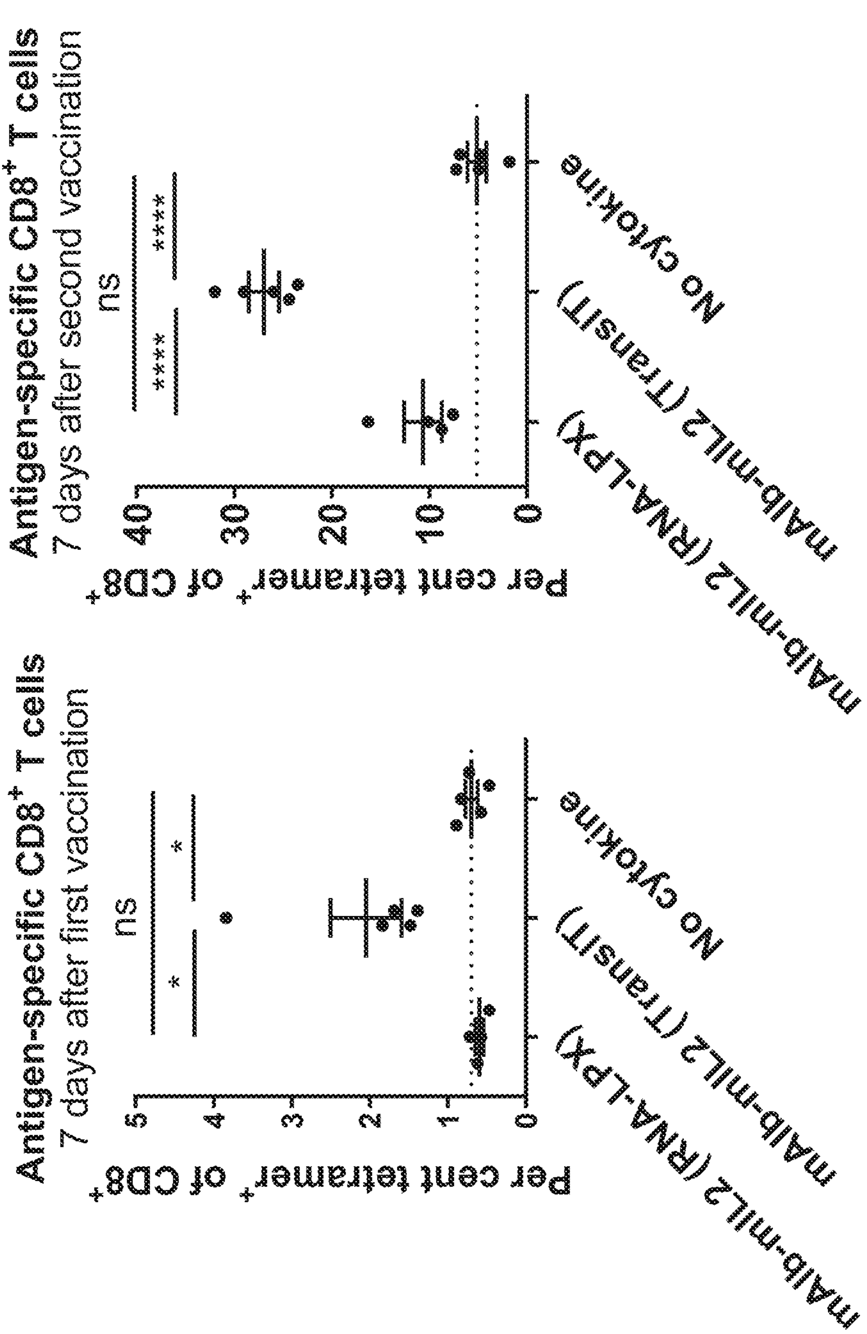

FIG. 25: Liver but not secondary lymphoid organ targeted mAlb-mIL2 readily increases vaccine induced T-cell responses.

BALB/c mice (n=5) were treated with gp70 RNA-LPX vaccination (20 μg i.v.) and an anti-PD-L1 blocking antibody (100 μg i.p.) on day 0 and 7, followed two days later by administration of 1 μg mRNA encoding mAlb-mIL2 either in TransIT (mAlb-mIL2 (TransIT)) or as lipoplex ((mAlb-mIL2 (RNA-LPX)). On day 7 and 14 blood was analyzed by flow cytometry for gp70 AH1 tetramer $CD8^+$ T cells. Statistical significance was determined using a one-way ANOVA followed by Tukey's multiple comparisons test. Mean±s.e.m.

FIG. 26: Validation of hIL2 encoding constructs.

A, Binding of hIL2 constructs to human IL2 receptor alpha (CD25) by ELISA. Plate-bound recombinant human CD25 was incubated with hIL2-containing supernatants from lipofection of 3 μg hIL2-encoding mRNA in HEK-293T-17 and bound protein was detected via an HRP-conjugated anti-human serum albumin antibody. Data shown are mean±SD of n=2 technical replicates. B, Western blot analysis of HEK-293T-17 supernatants after 24 h of expression of hIL2 encoding mRNAs. HEK-293T-17 cells were lipofected with mRNAs encoding for the indicated proteins, supernatants were harvested after 24 h of expression and used for Western blot analysis with anti-hIL2 antibody. C, CTLL-2 proliferation assay measuring biological activity of hIL2 constructs. CD25high mouse T cell line CTLL-2 was incubated for 72 h with a serial dilution of hIL2-containing supernatants and proliferation was measured by quantitating viable cells via ATP amount using the CellTiter-Glo® 2.0 Assay. Supernatants of HEK-293T-17 cells lipofected with mRNA encoding for hAlb were used as negative control. Data shown are mean±SD of n=2 technical replicates. RLU=relative luminescence units. D, Bioactivity of hIL2 constructs in human CD4+ and CD8+ T cells. CFSE-labeled human PBMCs were incubated with a suboptimal concentration of anti-CD3 antibody and serial dilutions of hIL2-containing supernatants for four days. Supernatants of HEK-293T-17 cells lipofected with mRNA encoding for hAlb were used as negative control. hIL2-mediated enhancement of antigen-unspecific proliferation of CD4+ T cells and CD8+ T cells was measured by flow cytometry. Data is shown from one representative donor as mean values of % divided cells as calculated using FlowJo v10.4 software. Error bars (SD) indicate the variation within the experiment (three replicates).

FIG. 27: Validation of hIL7 encoding constructs.

A, Expression of mRNA-encoded hIL7 constructs. HEK-293T-17 cells were lipofected with 3 μg mRNA (400 ng mRNA complexed per μL Lipofectamine MessengerMAX). After 20 h of incubation, hIL7 levels in cell-free supernatants were measured by ELISA. Data shown are mean±SD of n=2-3 replicates. B, Western blot analysis of HEK-293T-17 supernatants after 24 h of expression of hIL7 encoding mRNAs. HEK-293T-17 cells were lipofected with mRNAs encoding for the indicated proteins, supernatants were harvested after 24 h of expression and used for Western blot analysis with anti-hIL7 antibody. C, Bioactivity of hIL7 constructs in human CD4+ and CD8+ T cells. CFSE-labeled human PBMCs were incubated with a sub-optimal concentration of anti-CD3 antibody and serial dilutions of hIL7-containing supernatants for four days. Supernatants of HEK-293T-17 cells lipofected with mRNA encoding for hAlb were included as negative control and recombinant hIL-7 protein as positive control. hIL7-mediated enhancement of antigen-unspecific proliferation of CD4+ T cells and CD8+ T cells was measured by flow cytometry. Data is shown from one representative donor as mean values of % divided cells as calculated using FlowJo v10.4 software. Error bars (SD) indicate the variation within the experiment (three replicates).

Figure 28:
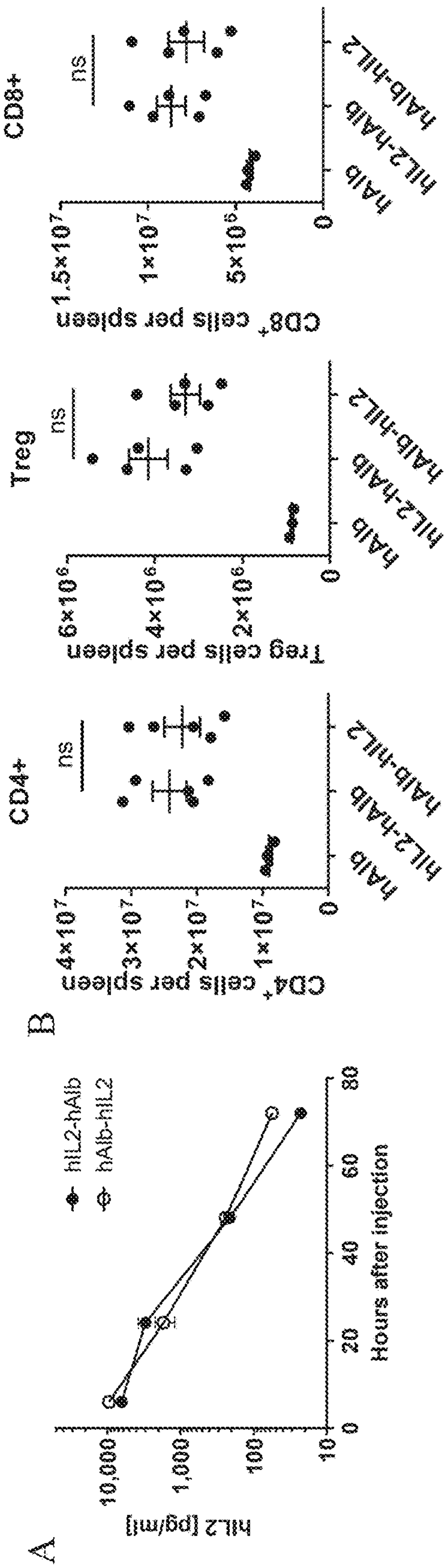

FIG. 28: The respective order of cytokine and albumin moiety within the active protein neither influences stability, pharmacokinetic profile nor functionality in vivo.

BALB/c mice (n=3 per group and time point) were injected i.v. with 1 μg hIL2 fused to the N-(hIL2-hAlb) or C-terminus (hAlb-hIL2) of hAlb or control mRNA encoding hAlb formulated with TransIT i.v. A, Cytokine levels were determined in the serum 6, 24 and 48 h and 72 h after injection by hIL2 singleplex assay. B, Absolute T lymphocyte numbers were determined in the spleen 96 h after injection by flow cytometry. Mean±s.e.m.

Figure 29:
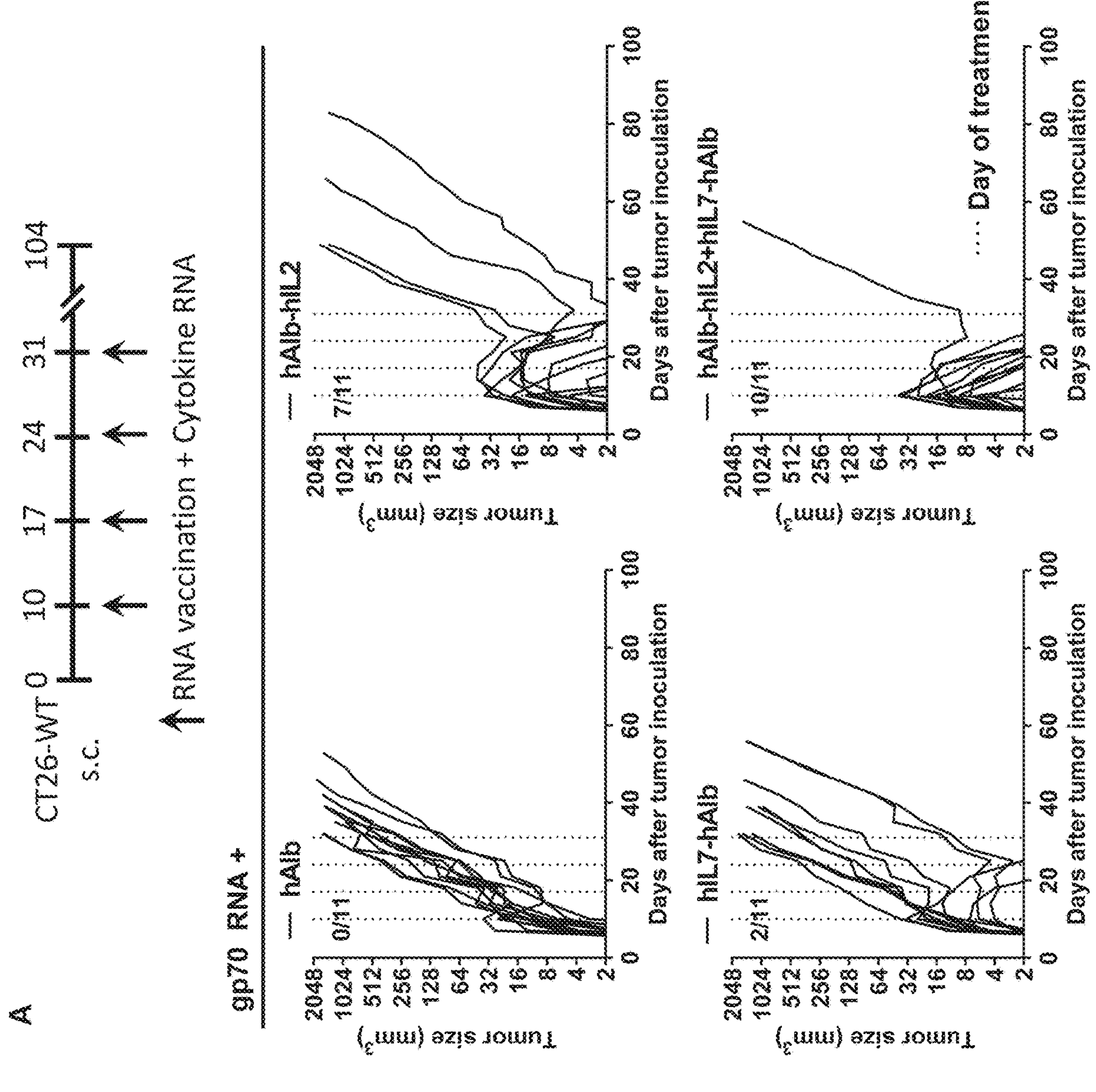
Figure 29:
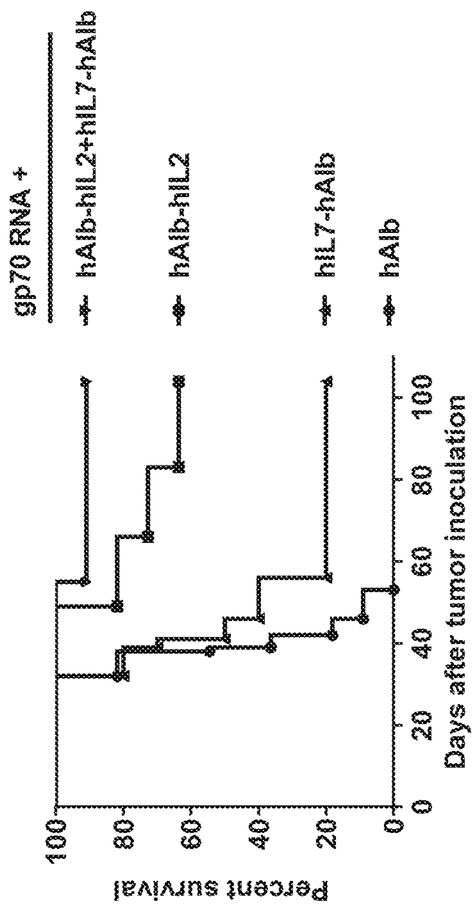

FIG. 29: Tumor rejection by the combination of hAlb-hIL2 and hIL7-hAlb with mRNA vaccination.

BALB/c mice (n=11 per group) were injected subcutaneously with $5\times10^5$ CT26-WT tumor cells in 100 μl PBS s.c. Ten days later, mice were treated with gp70 RNA-LPX (20 μg i.v.) and 3 μg hAlb-hIL2, hIL7-hAlb, or the combination of the two, formulated as lipid nanoparticles (LNP) and injected i.v. (liver targeting). As control, hAlb RNA was administered. The treatment schedule was repeated weekly as depicted in the upper panel. A, Growth curves of individual mice are shown. B, Percent survival of treatment groups is depicted.

FIG. 30: hAlb-hIL2 and the combination of hAlb-hIL2 and hIL7-hAlb boost vaccine induced antigen specific over unspecific CD8+ T cell responses.

CT26 tumor bearing mice described in Example 21 were analyzed by flow cytometry for gp70 AH1 tetramer+ CD8+ T cells in blood 7 days after each of three consecutive treatments (day 17, 24 and 31 after tumor inoculation). A, Absolute numbers of tumor antigen specific CD8+ T cells (left) as well as the fraction thereof among CD8+ T cells (right) after the first vaccination are depicted. B, Absolute numbers of tumor antigen specific and C, unspecific CD8+ T cells after each vaccination over time. D, Fold increase over the median antigen specific or unspecific CD8+ T-cell count of hAlb treated control animals seven days after the first treatment is shown. Statistical significance was determined using a one-way ANOVA (A) or two-way ANOVA (B) followed by Dunnett's multiple comparisons test, and two-way ANOVA followed by Sidak's multiple comparisons test (C, D). Mean±s.e.m.

FIG. 31: hAlb-hIL2 and hIL7-hAlb control T reg cell levels over time.

CT26 tumor bearing mice described in Example 21 were analyzed by flow cytometry for Treg cells in blood 7 days after each of three consecutive treatments (day 17, 24 and 31 after tumor inoculation). A, Absolute numbers of CD4+ CD25+ FoxP3+ Treg cells (left) as well as the fraction thereof among CD4+ T cells (right) after the first vaccination are depicted. B, Absolute numbers of CD4+ CD25+ FoxP3+ Treg cells after each vaccination over time. Statistical significance was determined using a one-way ANOVA (A) or two-way ANOVA (B) followed by Dunnett's multiple comparisons test. Mean±s.e.m.

FIG. 32: hAlb-hIL2 and hIL7-hAlb both expand CD8+ T cells over Treg cells. The ratios of absolute numbers of tumor antigen specific (A) or unspecific CD8+ T cells over Treg cells (B) from CT26 tumor bearing mice in Example 21 and analyzed in Example 22 and 23 are depicted. Statistical significance was determined using a two-way ANOVA followed by Dunnett's multiple comparisons test. Mean±s.e.m.

DETAILED DESCRIPTION

Although the present disclosure is described in detail below, it is to be understood that this disclosure is not limited to the particular methodologies, protocols and reagents described herein as these may vary. It is also to be understood that the terminology used herein is for the purpose of describing particular embodiments only, and is not intended to limit the scope of the present disclosure which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present disclosure will employ, unless otherwise indicated, conventional methods of chemistry, biochemistry, cell biology, immunology, and recombinant DNA techniques which are explained in the literature in the field (cf., e.g., Molecular Cloning: A Laboratory Manual, 2nd Edition, J. Sambrook et al. eds., Cold Spring Harbor Laboratory Press, Cold Spring Harbor 1989).

In the following, the elements of the present disclosure will be described. These elements are listed with specific embodiments, however, it should be understood that they may be combined in any manner and in any number to create additional embodiments. The variously described examples and embodiments should not be construed to limit the present disclosure to only the explicitly described embodiments. This description should be understood to disclose and encompass embodiments which combine the explicitly described embodiments with any number of the disclosed elements. Furthermore, any permutations and combinations of all described elements should be considered disclosed by this description unless the context indicates otherwise.

The term "about" means approximately or nearly, and in the context of a numerical value or range set forth herein in one embodiment means ±20%, ±10%, ±5%, or ±3% of the numerical value or range recited or claimed.

The terms "a" and "an" and "the" and similar reference used in the context of describing the disclosure (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it was individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the disclosure and does not pose a limitation on the scope of the claims. No language in the specification should be construed as indicating any non-claimed element essential to the practice of the disclosure.

Unless expressly specified otherwise, the term "comprising" is used in the context of the present document to indicate that further members may optionally be present in addition to the members of the list introduced by "comprising". It is, however, contemplated as a specific embodiment of the present disclosure that the term "comprising" encompasses the possibility of no further members being present, i.e., for the purpose of this embodiment "comprising" is to be understood as having the meaning of "consisting of".

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the present disclosure was not entitled to antedate such disclosure.

In the following, definitions will be provided which apply to all aspects of the present disclosure. The following terms have the following meanings unless otherwise indicated. Any undefined terms have their art recognized meanings.

According to the disclosure, the term "peptide" comprises oligo- and polypeptides and refers to substances which comprise about two or more, about 3 or more, about 4 or more, about 6 or more, about 8 or more, about 10 or more, about 13 or more, about 16 or more, about 20 or more, and up to about 50, about 100 or about 150, consecutive amino acids linked to one another via peptide bonds. The term "protein" or "polypeptide" refers to large peptides, in particular peptides having at least about 151 amino acids, but the terms "peptide", "protein" and "polypeptide" are used herein usually as synonyms.

A "therapeutic protein" has a positive or advantageous effect on a condition or disease state of a subject when provided to the subject in a therapeutically effective amount. In one embodiment, a therapeutic protein has curative or palliative properties and may be administered to ameliorate, relieve, alleviate, reverse, delay onset of or lessen the severity of one or more symptoms of a disease or disorder. A therapeutic protein may have prophylactic properties and may be used to delay the onset of a disease or to lessen the severity of such disease or pathological condition. The term "therapeutic protein" includes entire proteins or peptides, and can also refer to therapeutically active fragments thereof. It can also include therapeutically active variants of a protein. Examples of therapeutically active proteins include, but are not limited to, cytokines.

"Fragment", with reference to an amino acid sequence (peptide or protein), relates to a part of an amino acid sequence, i.e. a sequence which represents the amino acid sequence shortened at the N-terminus and/or C-terminus. A fragment shortened at the C-terminus (N-terminal fragment) is obtainable e.g. by translation of a truncated open reading frame that lacks the 3'-end of the open reading frame. A fragment shortened at the N-terminus (C-terminal fragment) is obtainable e.g. by translation of a truncated open reading frame that lacks the 5'-end of the open reading frame, as long as the truncated open reading frame comprises a start codon that serves to initiate translation. A fragment of an amino acid sequence comprises e.g. at least 50%, at least 60%, at least 70%, at least 80%, at least 90% of the amino acid residues from an amino acid sequence. A fragment of an amino acid sequence preferably comprises at least 6, in particular at least 8, at least 12, at least 15, at least 20, at least 30, at least 50, or at least 100 consecutive amino acids from an amino acid sequence.

For the purposes of the present disclosure, "variants" of an amino acid sequence (peptide or protein) comprise amino acid insertion variants, amino acid addition variants, amino acid deletion variants and/or amino acid substitution variants. The term "variant" includes all splice variants, post-translationally modified variants, conformations, isoforms and species homologs, in particular those which are naturally expressed by cells.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible. Amino acid addition variants comprise amino- and/or carboxy-terminal fusions of one or more amino acids, such as 1, 2, 3, 5, 10, 20, 30, 50, or more amino acids. Amino acid deletion variants are characterized by the removal of one or more amino acids from the sequence, such as by removal of 1, 2, 3, 5, 10, 20, 30, 50, or more amino acids. The deletions may be in any position of the protein. Amino acid deletion variants that comprise the deletion at the N-terminal and/or C-terminal end of the protein are also called N-terminal and/or C-terminal truncation variants. Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in peptide and protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids.

Preferably the degree of similarity, preferably identity between a given amino acid sequence and an amino acid sequence which is a variant of said given amino acid sequence will be at least about 60%, 65%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences.

The term "percentage identity" is intended to denote a percentage of amino acid residues which are identical between the two sequences to be compared, obtained after the best alignment, this percentage being purely statistical and the differences between the two sequences being distributed randomly and over their entire length. Sequence comparisons between two amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

Homologous amino acid sequences exhibit according to the disclosure at least 40%, in particular at least 50%, at least 60%, at least 70%, at least 80%, at least 90% and preferably at least 95%, at least 98 or at least 99% identity of the amino acid residues.

The amino acid sequence variants described herein may readily be prepared by the skilled person, for example, by recombinant DNA manipulation. The manipulation of DNA sequences for preparing peptides or proteins having substitutions, additions, insertions or deletions, is described in detail in Sambrook et al. (1989), for example. Furthermore, the peptides and amino acid variants described herein may be readily prepared with the aid of known peptide synthesis techniques such as, for example, by solid phase synthesis and similar methods.

In one embodiment, a fragment or variant of an amino acid sequence (peptide or protein) is preferably a "functional fragment" or "functional variant". The term "functional fragment" or "functional variant" of an amino acid sequence relates to any fragment or variant exhibiting one or more functional properties identical or similar to those of the amino acid sequence from which it is derived, i.e., it is functionally equivalent. With respect to cytokines, one particular function is one or more immunomodulatory activities displayed by the amino acid sequence from which the fragment or variant is derived and/or binding to the receptor (s) the amino acid sequence from which the fragment or variant is derived binds to.

An amino acid sequence (peptide or protein) "derived from" a designated amino acid sequence (peptide or protein) refers to the origin of the first amino acid sequence. Preferably, the amino acid sequence which is derived from a particular amino acid sequence has an amino acid sequence that is identical, essentially identical or homologous to that particular sequence or a fragment thereof. Amino acid sequences derived from a particular amino acid sequence may be variants of that particular sequence or a fragment thereof. For example, it will be understood by one of ordinary skill in the art that the cytokines (e.g., IL2 or IL7) suitable for use herein may be altered such that they vary in sequence from the naturally occurring or native sequences from which they were derived, while retaining the desirable activity of the native sequences.

In the present disclosure, the term "RNA" relates to a nucleic acid molecule which includes ribonucleotide residues. In preferred embodiments, the RNA contains all or a majority of ribonucleotide residues. As used herein, "ribonucleotide" refers to a nucleotide with a hydroxyl group at the 2'-position of a β-D-ribofuranosyl group. RNA encompasses without limitation, double stranded RNA, single stranded RNA, isolated RNA such as partially purified RNA, essentially pure RNA, synthetic RNA, recombinantly produced RNA, as well as modified RNA that differs from naturally occurring RNA by the addition, deletion, substitution and/or alteration of one or more nucleotides. Such alterations may refer to addition of non-nucleotide material to internal RNA nucleotides or to the end(s) of RNA. It is also contemplated herein that nucleotides in RNA may be non-standard nucleotides, such as chemically synthesized nucleotides or deoxynucleotides. For the present disclosure, these altered RNAs are considered analogs of naturally-occurring RNA.

In certain embodiments of the present disclosure, the RNA is messenger RNA (mRNA) that relates to a RNA transcript which encodes a peptide or protein. As established in the art, mRNA generally contains a 5' untranslated region (5'-UTR), a peptide coding region and a 3' untranslated region (3'-UTR). In some embodiments, the RNA is produced by in vitro transcription or chemical synthesis. In one embodiment, the mRNA is produced by in vitro transcription using a DNA template where DNA refers to a nucleic acid that contains deoxyribonucleotides.

In one embodiment, RNA is in vitro transcribed RNA (IVT-RNA) and may be obtained by in vitro transcription of an appropriate DNA template. The promoter for controlling transcription can be any promoter for any RNA polymerase. A DNA template for in vitro transcription may be obtained by cloning of a nucleic acid, in particular cDNA, and introducing it into an appropriate vector for in vitro transcription. The cDNA may be obtained by reverse transcription of RNA.

In one embodiment, the RNA may have modified ribonucleotides. Examples of modified ribonucleotides include, without limitation, 5-methylcytidine, pseudouridine and/or 1-methyl-pseudouridine.

In some embodiments, the RNA according to the present disclosure comprises a 5'-cap. In one embodiment, the RNA of the present disclosure does not have uncapped 5'-triphosphates. In one embodiment, the RNA may be modified by a 5'-cap analog. The term "5'-cap" refers to a structure found on the 5'-end of an mRNA molecule and generally consists of a guanosine nucleotide connected to the mRNA via a 5' to 5' triphosphate linkage. In one embodiment, this guanosine is methylated at the 7-position. Providing an RNA with a 5'-cap or 5'-cap analog may be achieved by in vitro transcription, in which the 5'-cap is co-transcriptionally expressed into the RNA strand, or may be attached to RNA post-transcriptionally using capping enzymes.

In some embodiments, RNA according to the present disclosure comprises a 5'-UTR and/or a 3'-UTR. The term "untranslated region" or "UTR" relates to a region in a DNA molecule which is transcribed but is not translated into an amino acid sequence, or to the corresponding region in an RNA molecule, such as an mRNA molecule. An untranslated region (UTR) can be present 5' (upstream) of an open reading frame (5'-UTR) and/or 3' (downstream) of an open reading frame (3'-UTR). A 5'-UTR, if present, is located at the 5' end, upstream of the start codon of a protein-encoding region. A 5'-UTR is downstream of the 5'-cap (if present), e.g. directly adjacent to the 5'-cap. A 3'-UTR, if present, is located at the 3' end, downstream of the termination codon of a protein-encoding region, but the term "3'-UTR" does preferably not include the poly(A) tail. Thus, the 3'-UTR is upstream of the poly(A) sequence (if present), e.g. directly adjacent to the poly(A) sequence.

In some embodiments, the RNA according to the present disclosure comprises a 3'-poly(A) sequence. The term "poly (A) sequence" relates to a sequence of adenyl (A) residues which typically is located at the 3'-end of a RNA molecule. According to the disclosure, in one embodiment, a poly(A) sequence comprises at least about 20, at least about 40, at least about 80, or at least about 100, and up to about 500, up to about 400, up to about 300, up to about 200, or up to about 150 A nucleotides, and in particular about 120 A nucleotides.

In the context of the present disclosure, the term "transcription" relates to a process, wherein the genetic code in a DNA sequence is transcribed into RNA. Subsequently, the RNA may be translated into peptide or protein.

With respect to RNA, the term "expression" or "translation" relates to the process in the ribosomes of a cell by which a strand of mRNA directs the assembly of a sequence of amino acids to make a peptide or protein.

According to the disclosure, the term "RNA encodes" means that the RNA, if present in the appropriate environment, such as within cells of a target tissue, can direct the assembly of amino acids to produce the peptide or protein it encodes during the process of translation. In one embodiment, RNA is able to interact with the cellular translation machinery allowing translation of the peptide or protein. A cell may produce the encoded peptide or protein intracellularly (e.g. in the cytoplasm and/or in the nucleus), may secrete the encoded peptide or protein, or may produce it on the surface.

As used herein, the terms "linked," "fused", or "fusion" are used interchangeably. These terms refer to the joining together of two or more elements or components or domains.

As used herein, "half-life" refers to the time taken for the serum or plasma concentration of a peptide or protein to reduce by 50%, in vivo, for example due to degradation and/or clearance or sequestration by natural mechanisms. An extended-PK interleukin (IL) suitable for use herein is stabilized in vivo and its half-life increased by, e.g., fusion to serum albumin (e.g., HSA or MSA), which resist degradation and/or clearance or sequestration. The half-life can be determined in any manner known per se, such as by pharmacokinetic analysis. Suitable techniques will be clear to the person skilled in the art, and may for example generally involve the steps of suitably administering a suitable dose of the amino acid sequence or compound to a subject; collecting blood samples or other samples from said subject at regular intervals; determining the level or concentration of the amino acid sequence or compound in said blood sample; and calculating, from (a plot of) the data thus obtained, the time until the level or concentration of the amino acid sequence or compound has been reduced by 50% compared to the initial level upon dosing. Further details are provided in, e.g., standard handbooks, such as Kenneth, A. et al., Chemical Stability of Pharmaceuticals: A Handbook for Pharmacists and in Peters et al., Pharmacokinetic Analysis: A Practical Approach (1996). Reference is also made to Gibaldi, M. et al., Pharmacokinetics, 2nd Rev. Edition, Marcel Dekker (1982).

Cytokines are a category of small proteins (~5-20 kDa) that are important in cell signalling. Their release has an effect on the behavior of cells around them. Cytokines are involved in autocrine signalling, paracrine signalling and endocrine signalling as immunomodulating agents. Cytokines include chemokines, interferons, interleukins, lymphokines, and tumour necrosis factors but generally not hormones or growth factors (despite some overlap in the terminology). Cytokines are produced by a broad range of cells, including immune cells like macrophages, B lymphocytes, T lymphocytes and mast cells, as well as endothelial cells, fibroblasts, and various stromal cells. A given cytokine may be produced by more than one type of cell. Cytokines act through receptors, and are especially important in the immune system; cytokines modulate the balance between humoral and cell-based immune responses, and they regulate the maturation, growth, and responsiveness of particular cell populations. Some cytokines enhance or inhibit the action of other cytokines in complex ways.

Interleukin-2 (IL2) is a cytokine that induces proliferation of antigen-activated T cells and stimulates natural killer (NK) cells. The biological activity of IL2 is mediated through a multi-subunit IL2 receptor complex (IL2R) of three polypeptide subunits that span the cell membrane: p55 (IL2Rα, the alpha subunit, also known as CD25 in humans), p75 (IL2Rβ, the beta subunit, also known as CD122 in humans) and p64 (IL2Rγ, the gamma subunit, also known as CD 132 in humans). T cell response to IL2 depends on a variety of factors, including: (1) the concentration of IL2; (2) the number of IL2R molecules on the cell surface; and (3) the number of IL2R occupied by IL2 (i.e., the affinity of the binding interaction between IL2 and IL2R (Smith, "Cell Growth Signal Transduction is Quantal" In Receptor Activation by Antigens, Cytokines, Hormones, and Growth Factors 766:263-271, 1995)). The IL2:1L2R complex is internalized upon ligand binding and the different components undergo differential sorting. When administered as an intravenous (i.v.) bolus, IL2 has a rapid systemic clearance (an initial clearance phase with a half-life of 12.9 minutes followed by a slower clearance phase with a half-life of 85 minutes) (Konrad et al., Cancer Res. 50:2009-2017, 1990).

Outcomes of systemic IL2 administration in cancer patients are far from ideal. While 15 to 20 percent of patients respond objectively to high-dose IL2, the great majority do not, and many suffer severe, life-threatening side effects, including nausea, confusion, hypotension, and septic shock. The severe toxicity associated with high-dose IL2 treatment is largely attributable to the activity of natural killer (NK) cells.

Attempts to reduce serum concentration by reducing dose and adjusting dosing regimen have been attempted, and while less toxic, such treatments were also less efficacious.

According to the disclosure, in certain embodiments, IL2 is attached to a pharmacokinetic modifying group. The resulting molecule, hereafter referred to as "extended-pharmacokinetic (PK) IL2," has a prolonged circulation half-life relative to free IL2. The prolonged circulation half-life of extended-PK IL2 permits in vivo serum IL2 concentrations to be maintained within a therapeutic range, potentially leading to the enhanced activation of many types of immune cells, including T cells. Because of its favorable pharmacokinetic profile, extended-PK IL2 can be dosed less frequently and for longer periods of time when compared with unmodified IL2.

According to the disclosure, IL2 (optionally as a portion of extended-PK IL2) may be naturally occurring IL2 or a fragment or variant thereof. IL2 may be human IL2 and may be derived from any vertebrate, especially any mammal. In one embodiment, IL2 comprises the amino acid sequence of SEQ ID NO: 1 or an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 1. In one embodiment, IL2 or a IL2 fragment or variant binds to the IL2 receptor, in particular to the alpha subunit of the IL2 receptor.

In certain embodiments, the IL2 moiety of the extended-PK IL2 is human IL2. In other embodiments, the IL2 moiety of the extended-PK IL2 is a fragment or variant of human IL2.

In certain embodiments described herein, IL2 is fused to a heterologous polypeptide (i.e., a polypeptide that is not IL2). The heterologous polypeptide can increase the circulating half-life of IL2. As discussed in further detail infra, the polypeptide that increases the circulating half-life may be serum albumin, such as human or mouse serum albumin.

IL7 is a hematopoietic growth factor secreted by stromal cells in the bone marrow and thymus. It is also produced by keratinocytes, dendritic cells, hepatocytes, neurons, and epithelial cells, but is not produced by normal lymphocytes. IL7 is a cytokine important for B and T cell development. IL7 cytokine and the hepatocyte growth factor form a heterodimer that functions as a pre-pro-B cell growth-stimulating factor. Knockout studies in mice suggested that IL7 plays an essential role in lymphoid cell survival.

IL7 binds to the IL7 receptor, a heterodimer consisting of IL7 receptor α and common γ chain receptor. Binding results in a cascade of signals important for T-cell development within the thymus and survival within the periphery. Knockout mice which genetically lack IL7 receptor exhibit thymic atrophy, arrest of T-cell development at the double positive stage, and severe lymphopenia. Administration of IL7 to mice results in an increase in recent thymic emigrants, increases in B and T cells, and increased recovery of T cells after cyclophosphamide administration or after bone marrow transplantation.

According to the disclosure, in certain embodiments, IL7 is attached to a pharmacokinetic modifying group. The resulting molecule, hereafter referred to as "extended-pharmacokinetic (PK) IL7," has a prolonged circulation half-life relative to free IL7. The prolonged circulation half-life of extended-PK IL7 permits in vivo serum IL7 concentrations to be maintained within a therapeutic range, potentially leading to the enhanced survival of many types of immune cells, including T cells. Because of its favorable pharmacokinetic profile, extended-PK IL7 can be dosed less frequently and for longer periods of time when compared with unmodified IL7.

According to the disclosure, IL7 may be naturally occurring IL7 or a fragment or variant thereof. IL7 may be human IL7 and may be derived from any vertebrate, especially any mammal. In one embodiment, IL7 comprises the amino acid sequence of SEQ ID NO: 2 or an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 2. In one embodiment, IL7 or a IL7 fragment or variant binds to the IL7 receptor.

In certain embodiments, the IL7 moiety of the extended-PK IL7 is human IL7. In other embodiments, the IL7 moiety of the extended-PK IL7 is a fragment or variant of human IL7.

In certain embodiments described herein, IL7 is fused to a heterologous polypeptide (i.e., a polypeptide that is not IL7). The heterologous polypeptide can increase the circulating half-life of IL7. As discussed in further detail infra, the polypeptide that increases the circulating half-life may be serum albumin, such as human or mouse serum albumin.

Interferons (IFNs) are a group of signaling proteins made and released by host cells in response to the presence of several pathogens, such as viruses, bacteria, parasites, and also tumor cells. In a typical scenario, a virus-infected cell will release interferons causing nearby cells to heighten their anti-viral defenses.

The IFNβ proteins are produced in large quantities by fibroblasts. They have antiviral activity that is involved mainly in innate immune response. Two types of IFNβ have been described, IFNβ1 and IFNβ3. The natural and recombinant forms of IFNβ1 have antiviral, antibacterial, and anticancer properties. Interferon-β1a (tradenames: Avonex and Rebif) and Interferon-β1b (tradenames: Betaseron/Betaferon) are used as drugs.

According to the disclosure, IFN-β may be naturally occurring IFN-β or a fragment or variant thereof. IFN-β may be human IFN-β and may be derived from any vertebrate, especially any mammal. In one embodiment, IFN-β comprises the amino acid sequence of SEQ ID NO: 3 or 4 or an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 3 or 4.

The cytokines, e.g. interleukins, described herein, such as IL2 or IL7, may be fused to an extended-PK group, which increases circulation half-life. Non-limiting examples of extended-PK groups are described infra. It should be understood that other PK groups that increase the circulation half-life of cytokines, or variants thereof, are also applicable to the present disclosure. In certain embodiments, the extended-PK group is a serum albumin domain (e.g., mouse serum albumin, human serum albumin).

As used herein, the term "PK" is an acronym for "pharmacokinetic" and encompasses properties of a compound including, by way of example, absorption, distribution, metabolism, and elimination by a subject. As used herein, an "extended-PK group" refers to a protein, peptide, or moiety that increases the circulation half-life of a biologically active molecule when fused to or administered together with the biologically active molecule. Examples of an extended-PK group include serum albumin (e.g., HSA), Fc or Fc fragments and variants thereof, transferrin and variants thereof, and human serum albumin (HSA) binders (as disclosed in U.S. Publication Nos. 2005/0287153 and 2007/0003549). Other exemplary extended-PK groups are disclosed in Kontermann et al., Current Opinion in Biotechnology 2011; 22: 868-876, which is herein incorporated by reference in its entirety. As used herein, an "extended-PK IL" refers to an interleukin (IL) moiety in combination with an extended-PK group. In one embodiment, the extended-PK IL is a fusion protein in which an IL moiety is linked or fused to an extended-PK group. An exemplary fusion protein is an HSA/IL2 fusion in which an IL2 moiety is fused with HSA. Another exemplary fusion protein is an HSA/IL7 fusion in which an IL7 moiety is fused with HSA.

In certain embodiments, the serum half-life of an extended-PK cytokine is increased relative to the cytokine alone (i.e., the cytokine not fused to an extended-PK group). In certain embodiments, the serum half-life of the extended-PK cytokine is at least 20, 40, 60, 80, 100, 120, 150, 180, 200, 400, 600, 800, or 1000% longer relative to the serum half-life of the cytokine alone. In certain embodiments, the serum half-life of the extended-PK cytokine is at least 1.5-fold, 2-fold, 2.5-fold, 3-fold, 3.5 fold, 4-fold, 4.5-fold, 5-fold, 6-fold, 7-fold, 8-fold, 10-fold, 12-fold, 13-fold, 15-fold, 17-fold, 20-fold, 22-fold, 25-fold, 27-fold, 30-fold, 35-fold, 40-fold, or 50-fold greater than the serum half-life of the cytokine alone. In certain embodiments, the serum half-life of the extended-PK cytokine is at least 10 hours, 15 hours, 20 hours, 25 hours, 30 hours, 35 hours, 40 hours, 50 hours, 60 hours, 70 hours, 80 hours, 90 hours, 100 hours, 110 hours, 120 hours, 130 hours, 135 hours, 140 hours, 150 hours, 160 hours, or 200 hours.

In certain embodiments, the extended-PK group includes serum albumin, or fragments thereof or variants of the serum albumin or fragments thereof (all of which for the purpose of the present disclosure are comprised by the term "albumin"). Polypeptides described herein may be fused to albumin (or a fragment or variant thereof) to form albumin fusion proteins. Such albumin fusion proteins are described in U.S. Publication No. 20070048282.

As used herein, "albumin fusion protein" refers to a protein formed by the fusion of at least one molecule of albumin (or a fragment or variant thereof) to at least one molecule of a protein such as a therapeutic protein, in particular IL2 or IL7 (or fragment or variant thereof). The albumin fusion protein may be generated by translation of a nucleic acid in which a polynucleotide encoding a therapeutic protein is joined in-frame with a polynucleotide encoding an albumin. The therapeutic protein and albumin, once part of the albumin fusion protein, may each be referred to as a "portion", "region" or "moiety" of the albumin fusion protein (e.g., a "therapeutic protein portion" or an "albumin protein portion"). In a highly preferred embodiment, an albumin fusion protein comprises at least one molecule of a therapeutic protein (including, but not limited to a mature form of the therapeutic protein) and at least one molecule of albumin (including but not limited to a mature form of albumin). In one embodiment, an albumin fusion protein is processed by a host cell such as a cell of the target organ for administered RNA, e.g. a liver cell, and secreted into the circulation. Processing of the nascent albumin fusion protein that occurs in the secretory pathways of the host cell used for expression of the RNA may include, but is not limited to signal peptide cleavage; formation of disulfide bonds; proper folding; addition and processing of carbohydrates (such as for example, N- and O-linked glycosylation); specific proteolytic cleavages; and/or assembly into multimeric proteins. An albumin fusion protein is preferably encoded by RNA in a non-processed form which in particular has a signal peptide at its N-terminus and following secretion by a cell is preferably present in the processed form wherein in particular the signal peptide has been cleaved off. In a most preferred embodiment, the "processed form of an albumin fusion protein" refers to an albumin fusion protein product which has undergone N-terminal signal peptide cleavage, herein also referred to as a "mature albumin fusion protein".

In preferred embodiments, albumin fusion proteins comprising a therapeutic protein have a higher plasma stability compared to the plasma stability of the same therapeutic protein when not fused to albumin. Plasma stability typically refers to the time period between when the therapeutic protein is administered in vivo and carried into the bloodstream and when the therapeutic protein is degraded and cleared from the bloodstream, into an organ, such as the kidney or liver, that ultimately clears the therapeutic protein from the body. Plasma stability is calculated in terms of the half-life of the therapeutic protein in the bloodstream. The half-life of the therapeutic protein in the bloodstream can be readily determined by common assays known in the art.

As used herein, "albumin" refers collectively to albumin protein or amino acid sequence, or an albumin fragment or variant, having one or more functional activities (e.g., biological activities) of albumin. In particular, "albumin" refers to human albumin or fragments or variants thereof especially the mature form of human albumin, or albumin from other vertebrates or fragments thereof, or variants of these molecules. The albumin may be derived from any vertebrate, especially any mammal, for example human, cow, sheep, or pig. Non-mammalian albumins include, but are not limited to, hen and salmon. The albumin portion of the albumin fusion protein may be from a different animal than the therapeutic protein portion.

In certain embodiments, the albumin is human serum albumin (HSA), or fragments or variants thereof, such as those disclosed in U.S. Pat. No. 5,876,969, WO 2011/124718, WO 2013/075066, and WO 2011/0514789.

The terms, human serum albumin (HSA) and human albumin (HA) are used interchangeably herein. The terms, "albumin" and "serum albumin" are broader, and encompass human serum albumin (and fragments and variants thereof) as well as albumin from other species (and fragments and variants thereof).

As used herein, a fragment of albumin sufficient to prolong the therapeutic activity or plasma stability of the therapeutic protein refers to a fragment of albumin sufficient in length or structure to stabilize or prolong the therapeutic activity or plasma stability of the protein so that the plasma stability of the therapeutic protein portion of the albumin fusion protein is prolonged or extended compared to the plasma stability in the non-fusion state.

The albumin portion of the albumin fusion proteins may comprise the full length of the albumin sequence, or may include one or more fragments thereof that are capable of stabilizing or prolonging the therapeutic activity or plasma stability. Such fragments may be of 10 or more amino acids in length or may include about 15, 20, 25, 30, 50, or more contiguous amino acids from the albumin sequence or may include part or all of specific domains of albumin. For instance, one or more fragments of HSA spanning the first two immunoglobulin-like domains may be used. In a preferred embodiment, the HSA fragment is the mature form of HSA.

Generally speaking, an albumin fragment or variant will be at least 100 amino acids long, preferably at least 150 amino acids long.

According to the disclosure, albumin may be naturally occurring albumin or a fragment or variant thereof. Albumin may be human albumin and may be derived from any vertebrate, especially any mammal. In one embodiment, albumin comprises the amino acid sequence of SEQ ID NO: 5 or an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 5.

Preferably, the albumin fusion protein comprises albumin as the N-terminal portion, and a therapeutic protein as the C-terminal portion. Alternatively, an albumin fusion protein comprising albumin as the C-terminal portion, and a therapeutic protein as the N-terminal portion may also be used. In other embodiments, the albumin fusion protein has a therapeutic protein fused to both the N-terminus and the C-terminus of albumin. In a preferred embodiment, the therapeutic proteins fused at the N- and C-termini are the same therapeutic proteins. In another preferred embodiment, the therapeutic proteins fused at the N- and C-termini are different therapeutic proteins. In one embodiment, the different therapeutic proteins may be useful to treat or prevent the same or a related disease, disorder, or condition. In one embodiment, the different therapeutic proteins are both cytokines, wherein preferably one of the different therapeutic proteins is IL2 or IL7 and the other is an interferon such as IFNβ. In one embodiment, the albumin fusion protein has IFNβ fused to the N-terminus and IL2 fused to the C-terminus of albumin.

In one embodiment, the therapeutic protein(s) is (are) joined to the albumin through (a) peptide linker(s). A linker peptide between the fused portions may provide greater physical separation between the moieties and thus maximize the accessibility of the therapeutic protein portion, for instance, for binding to its cognate receptor. The linker peptide may consist of amino acids such that it is flexible or more rigid. The linker sequence may be cleavable by a protease or chemically.

As used herein, the term "Fc region" refers to the portion of a native immunoglobulin formed by the respective Fc domains (or Fc moieties) of its two heavy chains. As used herein, the term "Fc domain" refers to a portion or fragment of a single immunoglobulin (Ig) heavy chain wherein the Fc domain does not comprise an Fv domain. In certain embodiments, an Fc domain begins in the hinge region just upstream of the papain cleavage site and ends at the C-terminus of the antibody. Accordingly, a complete Fc domain comprises at least a hinge domain, a CH2 domain, and a CH3 domain. In certain embodiments, an Fc domain comprises at least one of: a hinge (e.g., upper, middle, and/or lower hinge region) domain, a CH2 domain, a CH3 domain, a CH4 domain, or a variant, portion, or fragment thereof. In certain embodiments, an Fc domain comprises a complete Fc domain (i.e., a hinge domain, a CH2 domain, and a CH3 domain). In certain embodiments, an Fc domain comprises a hinge domain (or portion thereof) fused to a CH3 domain (or portion thereof). In certain embodiments, an Fc domain comprises a CH2 domain (or portion thereof) fused to a CH3 domain (or portion thereof). In certain embodiments, an Fc domain consists of a CH3 domain or portion thereof. In certain embodiments, an Fc domain consists of a hinge domain (or portion thereof) and a CH3 domain (or portion thereof). In certain embodiments, an Fc domain consists of a CH2 domain (or portion thereof) and a CH3 domain. In certain embodiments, an Fc domain consists of a hinge domain (or portion thereof) and a CH2 domain (or portion thereof). In certain embodiments, an Fc domain lacks at least a portion of a CH2 domain (e.g., all or part of a CH2 domain). An Fc domain herein generally refers to a polypeptide comprising all or part of the Fc domain of an immunoglobulin heavy-chain. This includes, but is not limited to, polypeptides comprising the entire CH1, hinge, CH2, and/or CH3 domains as well as fragments of such peptides comprising only, e.g., the hinge, CH2, and CH3 domain. The Fc domain may be derived from an immunoglobulin of any species and/or any subtype, including, but not limited to, a human IgG1, IgG2, IgG3, IgG4, IgD, IgA, IgE, or IgM antibody. The Fc domain encompasses native Fc and Fc variant molecules. As set forth herein, it will be understood by one of ordinary skill in the art that any Fc domain may be modified such that it varies in amino acid sequence from the native Fc domain of a naturally occurring immunoglobulin molecule. In certain embodiments, the Fc domain has reduced effector function (e.g., FcγR binding).

The Fc domains of a polypeptide described herein may be derived from different immunoglobulin molecules. For example, an Fc domain of a polypeptide may comprise a CH2 and/or CH3 domain derived from an IgG1 molecule and a hinge region derived from an IgG3 molecule. In another example, an Fc domain can comprise a chimeric hinge region derived, in part, from an IgG1 molecule and, in part, from an IgG3 molecule. In another example, an Fc domain can comprise a chimeric hinge derived, in part, from an IgG1 molecule and, in part, from an IgG4 molecule.

In certain embodiments, an extended-PK group includes an Fc domain or fragments thereof or variants of the Fc domain or fragments thereof (all of which for the purpose of the present disclosure are comprised by the term "Fc domain"). The Fc domain does not contain a variable region that binds to antigen. Fc domains suitable for use in the present disclosure may be obtained from a number of different sources. In certain embodiments, an Fc domain is derived from a human immunoglobulin. In certain embodiments, the Fc domain is from a human IgG1 constant region. It is understood, however, that the Fc domain may be derived from an immunoglobulin of another mammalian species, including for example, a rodent (e.g.

a mouse, rat, rabbit, guinea pig) or non-human primate (e.g. chimpanzee, macaque) species.

Moreover, the Fc domain (or a fragment or variant thereof) may be derived from any immunoglobulin class, including IgM, IgG, IgD, IgA, and IgE, and any immunoglobulin isotype, including IgG1, IgG2, IgG3, and IgG4.

A variety of Fc domain gene sequences (e.g., mouse and human constant region gene sequences) are available in the form of publicly accessible deposits. Constant region domains comprising an Fc domain sequence can be selected lacking a particular effector function and/or with a particular modification to reduce immunogenicity. Many sequences of antibodies and antibody-encoding genes have been published and suitable Fc domain sequences (e.g. hinge, CH2, and/or CH3 sequences, or fragments or variants thereof) can be derived from these sequences using art recognized techniques.

In certain embodiments, the extended-PK group is a serum albumin binding protein such as those described in US2005/0287153, US2007/0003549, US2007/0178082, US2007/0269422, US2010/0113339, WO2009/083804, and WO2009/133208, which are herein incorporated by reference in their entirety. In certain embodiments, the extended-PK group is transferrin, as disclosed in U.S. Pat. Nos. 7,176,278 and 8,158,579, which are herein incorporated by reference in their entirety. In certain embodiments, the extended-PK group is a serum immunoglobulin binding protein such as those disclosed in US2007/0178082, which is herein incorporated by reference in its entirety. In certain embodiments, the extended-PK group is a fibronectin (Fn)-based scaffold domain protein that binds to serum albumin, such as those disclosed in US2012/0094909, which is herein incorporated by reference in its entirety. Methods of making fibronectin-based scaffold domain proteins are also disclosed in US2012/0094909. A non-limiting example of a Fn3-based extended-PK group is Fn3(HSA), i.e., a Fn3 protein that binds to human serum albumin.

In certain aspects, the extended-PK cytokine such as extended-PK IL, suitable for use according to the disclosure, can employ one or more peptide linkers. As used herein, the term "peptide linker" refers to a peptide or polypeptide sequence which connects two or more domains (e.g., the extended-PK moiety and an IL moiety such as IL2 or IL7) in a linear amino acid sequence of a polypeptide chain. For example, peptide linkers may be used to connect an IL2 moiety to a HSA domain. In another embodiment, peptide linkers may be used to connect an IL7 moiety to a HSA domain.

Linkers suitable for fusing the extended-PK group to e.g. IL2 or IL7 are well known in the art. Exemplary linkers include glycine-serine-polypeptide linkers, glycine-proline-polypeptide linkers, and proline-alanine polypeptide linkers. In certain embodiments, the linker is a glycine-serine-polypeptide linker, i.e., a peptide that consists of glycine and serine residues.

The peptide and protein antigens suitable for use according to the disclosure typically include a peptide or protein comprising an epitope for inducing an immune response. The peptide or protein or epitope may be derived from a target antigen, i.e. the antigen against which an immune response is to be elicited. For example, the peptide or protein antigen or the epitope contained within the peptide or protein antigen may be a target antigen or a fragment or variant of a target antigen.

A peptide and protein antigen encoded by the RNA administered according to the disclosure, i.e., a vaccine antigen, preferably results in stimulation, priming and/or expansion of T cells in the subject being administered the RNA. Said stimulated, primed and/or expanded T cells are preferably directed against a target antigen, in particular a target antigen expressed by diseased cells, tissues and/or organs, i.e., a disease-associated antigen. Thus, a vaccine antigen may comprise the disease-associated antigen, or a fragment or variant thereof. In one embodiment, such fragment or variant is immunologically equivalent to the disease-associated antigen. In the context of the present disclosure, the term "fragment of an antigen" or "variant of an antigen" means an agent which results in stimulation, priming and/or expansion of T cells which stimulated, primed and/or expanded T cells target the antigen, i.e. a disease-associated antigen, in particular when presented by diseased cells, tissues and/or organs. Thus, the vaccine antigen encoded by the RNA administered according to the disclosure may correspond to or may comprise the disease-associated antigen, may correspond to or may comprise a fragment of the disease-associated antigen or may correspond to or may comprise an antigen which is homologous to the disease-associated antigen or a fragment thereof. If the vaccine antigen encoded by the RNA administered according to the disclosure comprises a fragment of the disease-associated antigen or an amino acid sequence which is homologous to a fragment of the disease-associated antigen said fragment or amino acid sequence may comprise an epitope such as a T cell epitope of the disease-associated antigen or a sequence which is homologous to an epitope such as a T cell epitope of the disease-associated antigen. Thus, according to the disclosure, an antigen encoded by the RNA administered may comprise an immunogenic fragment of a disease-associated antigen or an amino acid sequence being homologous to an immunogenic fragment of a disease-associated antigen. An "immunogenic fragment of an antigen" according to the disclosure preferably relates to a fragment of an antigen which is capable of stimulating, priming and/or expanding T cells when presented in the context of MHC molecules. It is preferred that the vaccine antigen (similar to the disease-associated antigen) can be presented by a cell such as an antigen-presenting cell so as to provide the relevant epitope for binding by T cells. The vaccine antigen encoded by the RNA administered according to the disclosure may be a recombinant antigen.

The term "immunologically equivalent" means that the immunologically equivalent molecule such as the immunologically equivalent amino acid sequence exhibits the same or essentially the same immunological properties and/or exerts the same or essentially the same immunological effects, e.g., with respect to the type of the immunological effect. In the context of the present disclosure, the term "immunologically equivalent" is preferably used with respect to the immunological effects or properties of antigens or antigen variants used for immunization. For example, an amino acid sequence is immunologically equivalent to a reference amino acid sequence if said amino acid sequence when exposed to the immune system of a subject such as T cells binding to the reference amino acid sequence or cells expressing the reference amino acid sequence induces an immune reaction having a specificity of reacting with the reference amino acid sequence. Thus, a molecule which is immunologically equivalent to an antigen exhibits the same or essentially the same properties and/or exerts the same or essentially the same effects regarding the stimulation, priming and/or expansion of T cells as the antigen to which the T cells are targeted.

The term "priming" refers to a process wherein a T cell has its first contact with its specific antigen and causes differentiation into effector T cells.

The term "clonal expansion" or "expansion" refers to a process wherein a specific entity is multiplied. In the context of the present disclosure, the term is preferably used in the context of an immunological response in which lymphocytes are stimulated by an antigen, proliferate, and the specific lymphocyte recognizing said antigen is amplified. Preferably, clonal expansion leads to differentiation of the lymphocytes.

The term "antigen" relates to an agent comprising an epitope against which an immune response can be generated. The term "antigen" includes, in particular, proteins and peptides. In one embodiment, an antigen is presented by cells of the immune system such as antigen presenting cells like dendritic cells or macrophages. An antigen or a processing product thereof such as a T cell epitope is in one embodiment bound by a T or B cell receptor, or by an immunoglobulin molecule such as an antibody. Accordingly, an antigen or a processing product thereof may react specifically with antibodies or T-lymphocytes (T-cells). In one embodiment, an antigen is a disease-associated antigen, such as a tumor antigen, a viral antigen, or a bacterial antigen and an epitope is derived from such antigen.

The term "disease-associated antigen" is used in its broadest sense to refer to any antigen associated with a disease. A disease-associated antigen is a molecule which contains epitopes that will stimulate a host's immune system to make a cellular antigen-specific immune response and/or a humoral antibody response against the disease. The disease-associated antigen or an epitope thereof may therefore be used for therapeutic purposes. Disease-associated antigens may be associated with infection by microbes, typically microbial antigens, or associated with cancer, typically tumors.

The term "tumor antigen" refers to a constituent of cancer cells which may be derived from the cytoplasm, the cell surface and the cell nucleus. In particular, it refers to those antigens which are produced intracellularly or as surface antigens on tumor cells. A tumor antigen is typically expressed preferentially by cancer cells (e.g., it is expressed at higher levels in cancer cells than on non-cancer cells) and in some instances it is expressed solely by cancer cells. Examples of tumor antigens include, without limitation, p53, ART-4, BAGE, beta-catenin/m, Bcr-abL CAMEL, CAP-1, CASP-8, CDC27/m, CDK4/m, CEA, the cell surface proteins of the claudin family, such as CLAUDIN-6, CLAUDIN-18.2 and CLAUDIN-12, c-MYC, CT, Cyp-B, DAM, ELF2M, ETV6-AML1, G250, GAGE, GnT-V, Gap 100, HAGE, HER-2/neu, HPV-E7, HPV-E6, HAST-2, hTERT (or hTRT), LAGE, LDLR/FUT, MAGE-A, preferably MAGE-A1, MAGE-A2, MAGE-A3, MAGE-A4, MAGE-A5, MAGE-A6, MAGE-A7, MAGE-A8, MAGE-A9, MAGE-A 10, MAGE-A 1 1, or MAGE-A12, MAGE-B, MAGE-C, MART-1/Melan-A, MC1R, Myosin/m, MUC1, MUM-1, MUM-2, MUM-3, NA88-A, NF1, NY-ESO-1, NY-BR-1, p190 minor BCR-abL, Pml/RARa, PRAME, proteinase 3, PSA, PSM, RAGE, RU1 or RU2, SAGE, SART-1 or SART-3, SCGB3A2, SCP1, SCP2, SCP3, SSX, SURVIVIN, TEL/AML1, TPI/m, TRP-1, TRP-2, TRP-2/INT2, TPTE, WT, and WT-1.

The term "viral antigen" refers to any viral component having antigenic properties, i.e. being able to provoke an immune response in an individual. The viral antigen may be a viral ribonucleoprotein or an envelope protein.

The term "bacterial antigen" refers to any bacterial component having antigenic properties, i.e. being able to provoke an immune response in an individual. The bacterial antigen may be derived from the cell wall or cytoplasm membrane of the bacterium.

The term "epitope" refers to a part or fragment a molecule such as an antigen that is recognized by the immune system. For example, the epitope may be recognized by T cells, B cells or antibodies. An epitope of an antigen may include a continuous or discontinuous portion of the antigen and may be between about 5 and about 100, such as between about 5 and about 50, more preferably between about 8 and about 30, most preferably between about 10 and about 25 amino acids in length, for example, the epitope may be preferably 9, 10, 11, 12, 13, 14, 15, 16, 17, 18, 19, 20, 21, 22, 23, 24, or 25 amino acids in length. In one embodiment, an epitope is between about 10 and about 25 amino acids in length. The term "epitope" includes T cell epitopes.

The term "T cell epitope" refers to a part or fragment of a protein that is recognized by a T cell when presented in the context of MHC molecules. The term "major histocompatibility complex" and the abbreviation "MHC" includes MHC class I and MHC class II molecules and relates to a complex of genes which is present in all vertebrates. MHC proteins or molecules are important for signaling between lymphocytes and antigen presenting cells or diseased cells in immune reactions, wherein the MHC proteins or molecules bind peptide epitopes and present them for recognition by T cell receptors on T cells. The proteins encoded by the MHC are expressed on the surface of cells, and display both self-antigens (peptide fragments from the cell itself) and non-self-antigens (e.g., fragments of invading microorganisms) to a T cell. In the case of class I MHC/peptide complexes, the binding peptides are typically about 8 to about 10 amino acids long although longer or shorter peptides may be effective. In the case of class II MHC/peptide complexes, the binding peptides are typically about 10 to about 25 amino acids long and are in particular about 13 to about 18 amino acids long, whereas longer and shorter peptides may be effective.

The terms "T cell" and "T lymphocyte" are used interchangeably herein and include T helper cells (CD4+ T cells) and cytotoxic T cells (CTLs, CD8+ T cells) which comprise cytolytic T cells. The term "antigen-specifc T cell" or similar terms relate to a T cell which recognizes the antigen to which the T cell is targeted, in particular when presented on the surface of antigen presenting cells or diseased cells such as cancer cells in the context of MHC molecules and preferably exerts effector functions of T cells. T cells are considered to be specific for antigen if the cells kill target cells expressing an antigen. T cell specificity may be evaluated using any of a variety of standard techniques, for example, within a chromium release assay or proliferation assay. Alternatively, synthesis of lymphokines (such as interferon-γ) can be measured.

In one embodiment, the target antigen is a tumor antigen and the peptide or protein comprising an epitope or a fragment thereof (e.g., an epitope) is derived from the tumor antigen. The tumor antigen may be a "standard" antigen, which is generally known to be expressed in various cancers. The tumor antigen may also be a "neo-antigen", which is specific to an individual's tumor and has not been previously recognized by the immune system. A neo-antigen or neo-epitope may result from one or more cancer-specific mutations in the genome of cancer cells resulting in amino acid changes. If the tumor antigen is a neo-antigen, the peptide or protein comprising an epitope preferably comprises an epitope or a fragment of said neo-antigen comprising one or more amino acid changes.

Cancer mutations vary with each individual. Thus, cancer mutations that encode novel epitopes (neo-epitopes) represent attractive targets in the development of vaccine compositions and immunotherapies. The efficacy of tumor immunotherapy relies on the selection of cancer-specific antigens and epitopes capable of inducing a potent immune response within a host. RNA can be used to deliver patient-specific tumor epitopes to a patient. Dendritic cells (DCs) residing in the spleen represent antigen-presenting cells of particular interest for RNA expression of immunogenic epitopes or antigens such as tumor epitopes. The use of multiple epitopes has been shown to promote therapeutic efficacy in tumor vaccine compositions. Rapid sequencing of the tumor mutanome may provide multiple epitopes for individualized vaccines which can be encoded by RNA described herein, e.g., as a single polypeptide wherein the epitopes are optionally separated by linkers. In certain embodiments of the present disclosure, the RNA encodes at least one epitope, at least two epitopes, at least three epitopes, at least four epitopes, at least five epitopes, at least six epitopes, at least seven epitopes, at least eight epitopes, at least nine epitopes, or at least ten epitopes. Exemplary embodiments include RNA that encodes at least five epitopes (termed a "pentatope") and RNA that encodes at least ten epitopes (termed a "decatope").

The peptide and protein antigen can be 2-100 amino acids, including for example, 5 amino acids, 10 amino acids, 15 amino acids, 20 amino acids, 25 amino acids, 30 amino acids, 35 amino acids, 40 amino acids, 45 amino acids, or 50 amino acids in length. In some embodiments, a peptide can be greater than 50 amino acids. In some embodiments, the peptide can be greater than 100 amino acids.

The peptide or protein antigen can be any peptide or protein that can induce or increase the ability of the immune system to develop antibodies and T-cell responses to the peptide or protein.

In certain embodiments, immune checkpoint inhibitors are used in combination with other therapeutic agents described herein (e.g., RNA encoding extended pharmacokinetic (PK) interleukin (IL)-2 and/or RNA encoding extended pharmacokinetic (PK) interleukin (IL)-7 and RNA encoding a peptide or protein comprising an epitope).

As used herein, "immune checkpoint" refers to co-stimulatory and inhibitory signals that regulate the amplitude and quality of T cell receptor recognition of an antigen. In certain embodiments, the immune checkpoint is an inhibitory signal. In certain embodiments, the inhibitory signal is the interaction between PD-1 and PD-L1. In certain embodiments, the inhibitory signal is the interaction between CTLA-4 and CD80 or CD86 to displace CD28 binding. In certain embodiments the inhibitory signal is the interaction between LAG3 and MHC class II molecules. In certain embodiments, the inhibitory signal is the interaction between TIM3 and galectin 9.

As used herein, "immune checkpoint inhibitor" refers to a molecule that totally or partially reduces, inhibits, interferes with or modulates one or more checkpoint proteins. In certain embodiments, the immune checkpoint inhibitor prevents inhibitory signals associated with the immune checkpoint. In certain embodiments, the immune checkpoint inhibitor is an antibody, or fragment thereof that disrupts inhibitory signaling associated with the immune checkpoint. In certain embodiments, the immune checkpoint inhibitor is a small molecule that disrupts inhibitory signaling. In certain embodiments, the immune checkpoint inhibitor is an antibody, fragment thereof, or antibody mimic, that prevents the interaction between checkpoint blocker proteins, e.g., an antibody, or fragment thereof, that prevents the interaction between PD-1 and PD-L1. In certain embodiments, the immune checkpoint inhibitor is an antibody, or fragment thereof, that prevents the interaction between CTLA-4 and CD80 or CD86. In certain embodiments, the immune checkpoint inhibitor is an antibody, or fragment thereof, that prevents the interaction between LAG3 and its ligands, or TIM-3 and its ligands. The checkpoint inhibitor may also be in the form of the soluble form of the molecules (or variants thereof) themselves, e.g., a soluble PD-L1 or PD-L1 fusion.

The "Programmed Death-1 (PD-1)" receptor refers to an immuno-inhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1.

"Programmed Death Ligand-1 (PD-L1)" is one of two cell surface glycoprotein ligands for PD-1 (the other being PD-L2) that downregulates T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1.

"Cytotoxic T Lymphocyte Associated Antigen-4 (CTLA-4)" is a T cell surface molecule and is a member of the immunoglobulin superfamily. This protein downregulates the immune system by binding to CD80 and CD86. The term "CTLA-4" as used herein includes human CTLA-4 (hCTLA-4), variants, isoforms, and species homologs of hCTLA-4, and analogs having at least one common epitope with hCTLA-4.

"Lymphocyte Activation Gene-3 (LAG3)" is an inhibitory receptor associated with inhibition of lymphocyte activity by binding to MHC class II molecules. This receptor enhances the function of Treg cells and inhibits CD8+ effector T cell function. The term "LAG3" as used herein includes human LAG3 (hLAG3), variants, isoforms, and species homologs of hLAG3, and analogs having at least one common epitope.

"T Cell Membrane Protein-3 (TIM3)" is an inhibitory receptor involved in the inhibition of lymphocyte activity by inhibition of TH1 cells responses. Its ligand is galectin 9, which is upregulated in various types of cancers. The term "TIM3" as used herein includes human TIM3 (hTIM3), variants, isoforms, and species homologs of hTIM3, and analogs having at least one common epitope.

The "B7 family" refers to inhibitory ligands with undefined receptors. The B7 family encompasses B7-H3 and B7-H4, both upregulated on tumor cells and tumor infiltrating cells.

In certain embodiments, the immune checkpoint inhibitor suitable for use in the methods disclosed herein, is an antagonist of inhibitory signals, e.g., an antibody which targets, for example, PD-1, PD-L1, CTLA-4, LAG3, B7-H3, B7-H4, or TIM3. These ligands and receptors are reviewed in Pardoll, D., Nature. 12: 252-264, 2012.

In certain embodiments, the immune checkpoint inhibitor is an antibody or an antigen-binding portion thereof, that disrupts or inhibits signaling from an inhibitory immunoregulator. In certain embodiments, the immune checkpoint inhibitor is a small molecule that disrupts or inhibits signaling from an inhibitory immunoregulator.

In certain embodiments, the inhibitory immunoregulator is a component of the PD-1/PD-L1 signaling pathway. Accordingly, certain embodiments of the disclosure provide for administering to a subject an antibody or an antigen-binding portion thereof that disrupts the interaction between the PD-1 receptor and its ligand, PD-L1. Antibodies which bind to PD-1 and disrupt the interaction between the PD-1 and its ligand, PD-L1, are known in the art. In certain embodiments, the antibody or antigen-binding portion thereof binds specifically to PD-1. In certain embodiments, the antibody or antigen-binding portion thereof binds specifically to PD-L1 and inhibits its interaction with PD-1, thereby increasing immune activity.

In certain embodiments, the inhibitory immunoregulator is a component of the CTLA4 signaling pathway. Accordingly, certain embodiments of the disclosure provide for administering to a subject an antibody or an antigen-binding portion thereof that targets CTLA4 and disrupts its interaction with CD80 and CD86.

In certain embodiments, the inhibitory immunoregulator is a component of the LAG3 (lymphocyte activation gene 3) signaling pathway. Accordingly, certain embodiments of the disclosure provide for administering to a subject an antibody or an antigen-binding portion thereof that targets LAG3 and disrupts its interaction with MHC class II molecules.

In certain embodiments, the inhibitory immunoregulator is a component of the B7 family signaling pathway. In certain embodiments, the B7 family members are B7-H3 and B7-H4. Accordingly, certain embodiments of the disclosure provide for administering to a subject an antibody or an antigen-binding portion thereof that targets B7-H3 or H4. The B7 family does not have any defined receptors but these ligands are upregulated on tumor cells or tumor-infiltrating cells. Preclinical mouse models have shown that blockade of these ligands can enhance anti-tumor immunity.

In certain embodiments, the inhibitory immunoregulator is a component of the TIM3 (T cell membrane protein 3) signaling pathway. Accordingly, certain embodiments of the disclosure provide for administering to a subject an antibody or an antigen-binding portion thereof that targets TIM3 and disrupts its interaction with galectin 9.

It will be understood by one of ordinary skill in the art that other immune checkpoint targets can also be targeted by antagonists or antibodies, provided that the targeting results in the stimulation of an immune response such as an anti-tumor immune response as reflected in, e.g., an increase in T cell proliferation, enhanced T cell activation, and/or increased cytokine production (e.g., IFN-γ, IL2).

According to the disclosure, the term "antibody" refers to a glycoprotein comprising at least two heavy (H) chains and two light (L) chains inter-connected by disulfide bonds. The term "antibody" includes monoclonal antibodies, recombinant antibodies, human antibodies, humanized antibodies and chimeric antibodies. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

Antibodies may be derived from different species, including but not limited to mouse, rat, rabbit, guinea pig and human.

Antibodies described herein include IgA such as IgA1 or IgA2, IgG1, IgG2, IgG3, IgG4, IgE, IgM, and IgD antibodies. In various embodiments, the antibody is an IgG1 antibody, more particularly an IgG1, kappa or IgG1, lambda isotype (i.e. IgG1, κ, λ), an IgG2a antibody (e.g. IgG2a, κ, λ), an IgG2b antibody (e.g. IgG2b, κ, λ), an IgG3 antibody (e.g. IgG3, κ, λ) or an IgG4 antibody (e.g. IgG4, κ, λ).

The terms "antigen-binding portion" of an antibody (or simply "binding portion") or "antigen-binding fragment" of an antibody (or simply "binding fragment") or similar terms refer to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) Fab fragments, monovalent fragments consisting of the VL, VH, CL and CH domains; (ii) $F(ab')_2$ fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) Nature 341: 544-546), which consist of a VH domain; (vi) isolated complementarity determining regions (CDR), and (vii) combinations of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883). Such single chain antibodies are also intended to be encompassed within the term "antigen-binding fragment" of an antibody. A further example is binding-domain immunoglobulin fusion proteins comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

According to the disclosure, after administration of the RNA described herein, at least a portion of the RNA is delivered to a target cell. In one embodiment, at least a portion of the RNA is delivered to the cytosol of the target cell. In one embodiment, the RNA is translated by the target cell to produce the encoded peptide or protein.

Some aspects of the disclosure involve the targeted delivery of the RNA disclosed herein (e.g., RNA encoding extended pharmacokinetic (PK) interleukin (IL)-2 and/or RNA encoding extended pharmacokinetic (PK) interleukin (IL)-7 and RNA encoding a peptide or protein comprising an epitope) to certain tissues.

In one embodiment, the disclosure involves targeting the lymphatic system, in particular secondary lymphoid organs, more specifically spleen. Targeting the lymphatic system, in particular secondary lymphoid organs, more specifically spleen is in particular preferred if the RNA administered is RNA encoding a peptide or protein comprising an epitope.

In one embodiment, the target cell is a spleen cell. In one embodiment, the target cell is an antigen presenting cell such as a professional antigen presenting cell in the spleen. In one embodiment, the target cell is a dendritic cell in the spleen.

The "lymphatic system" is part of the circulatory system and an important part of the immune system, comprising a network of lymphatic vessels that carry lymph. The lymphatic system consists of lymphatic organs, a conducting network of lymphatic vessels, and the circulating lymph. The primary or central lymphoid organs generate lymphocytes from immature progenitor cells. The thymus and the bone marrow constitute the primary lymphoid organs. Secondary or peripheral lymphoid organs, which include lymph nodes and the spleen, maintain mature naive lymphocytes and initiate an adaptive immune response.

RNA may be delivered to spleen by so-called lipoplex formulations, in which the RNA is bound to liposomes comprising a cationic lipid and optionally an additional or helper lipid to form injectable nanoparticle formulations. The liposomes may be obtained by injecting a solution of the lipids in ethanol into water or a suitable aqueous phase. RNA lipoplex particles may be prepared by mixing the liposomes with RNA. Spleen targeting RNA lipoplex particles are described in WO 2013/143683, herein incorporated by reference. It has been found that RNA lipoplex particles having a net negative charge may be used to preferentially target spleen tissue or spleen cells such as antigen-presenting cells, in particular dendritic cells. Accordingly, following administration of the RNA lipoplex particles, RNA accumulation and/or RNA expression in the spleen occurs. Thus, RNA lipoplex particles of the disclosure may be used for expressing RNA in the spleen. In an embodiment, after administration of the RNA lipoplex particles, no or essentially no RNA accumulation and/or RNA expression in the lung and/or liver occurs. In one embodiment, after administration of the RNA lipoplex particles, RNA accumulation and/or RNA expression in antigen presenting cells, such as professional antigen presenting cells in the spleen occurs. Thus, RNA lipoplex particles of the disclosure may be used for expressing RNA in such antigen presenting cells. In one embodiment, the antigen presenting cells are dendritic cells and/or macrophages.

In the context of the present disclosure, the term "RNA lipoplex particle" relates to a particle that contains lipid, in particular cationic lipid, and RNA. Electrostatic interactions between positively charged liposomes and negatively charged RNA results in complexation and spontaneous formation of RNA lipoplex particles. Positively charged liposomes may be generally synthesized using a cationic lipid, such as DOTMA, and additional lipids, such as DOPE. In one embodiment, a RNA lipoplex particle is a nanoparticle.

As used herein, a "cationic lipid" refers to a lipid having a net positive charge. Cationic lipids bind negatively charged RNA by electrostatic interaction to the lipid matrix. Generally, cationic lipids possess a lipophilic moiety, such as a sterol, an acyl or diacyl chain, and the head group of the lipid typically carries the positive charge. Examples of cationic lipids include, but are not limited to 1,2-di-O-octadecenyl-3-trimethylammonium propane (DOTMA), dimethyldioctadecylammonium (DDAB); 1,2-dioleoyl-3-trimethylammonium propane (DOTAP); 1,2-dioleoyl-3-dimethylammonium-propane (DODAP); 1,2-diacyloxy-3-dimethylammonium propanes; 1,2-dialkyloxy-3-dimethylammonium propanes; dioctadecyldimethyl ammonium chloride (DODAC), 2,3-di(tetradecoxy)propyl-(2-hydroxyethyl)-dimethylazanium (DMRIE), 1,2-dimyristoyl-sn-glycero-3-ethylphosphocholine (DMEPC), I,2-dimyristoyl-3-trimethylammonium propane (DMTAP), 1,2-dioleyloxypropyl-3-dimethyl-hydroxyethyl ammonium bromide (DORIE), and 2,3-dioleoyloxy-N-[2(spermine carboxamide)ethyl]-N,N-dimethyl-I-propanamium trifluoroacetate (DOSPA). Preferred are DOTMA, DOTAP, DODAC, and DOSPA. In specific embodiments, the cationic lipid is DOTMA and/or DOTAP.

An additional lipid may be incorporated to adjust the overall positive to negative charge ratio and physical stability of the RNA lipoplex particles. In certain embodiments, the additional lipid is a neutral lipid. As used herein, a "neutral lipid" refers to a lipid having a net charge of zero. Examples of neutral lipids include, but are not limited to, 1,2-di-(9Z-octadecenoyI)-sn-glycero-3-phosphoethanolamine (DOPE), 1,2-dioleoyl-sn-glycero-3-phosphocholine (DOPC), diacylphosphatidyl choline, diacylphosphatidyl ethanol amine, ceramide, sphingoemyelin, cephalin, cholesterol, and cerebroside. In specific embodiments, the additional lipid is DOPE, cholesterol and/or DOPC.

In certain embodiments, the RNA lipoplex particles include both a cationic lipid and an additional lipid. In an exemplary embodiment, the cationic lipid is DOTMA and the additional lipid is DOPE.

In some embodiments, the molar ratio of the at least one cationic lipid to the at least one additional lipid is from about 10:0 to about 1:9, about 4:1 to about 1:2, or about 3:1 to about 1:1. In specific embodiments, the molar ratio may be about 3:1, about 2.75:1, about 2.5:1, about 2.25:1, about 2:1, about 1.75:1, about 1.5:1, about 1.25:1, or about 1:1. In an exemplary embodiment, the molar ratio of the at least one cationic lipid to the at least one additional lipid is about 2:1.

RNA lipoplex particles described herein have an average diameter that in one embodiment ranges from about 200 nm to about 1000 nm, from about 200 nm to about 800 nm, from about 250 to about 700 nm, from about 400 to about 600 nm, from about 300 nm to about 500 nm, or from about 350 nm to about 400 nm. In specific embodiments, the RNA lipoplex particles have an average diameter of about 200 nm, about 225 nm, about 250 nm, about 275 nm, about 300 nm, about 325 nm, about 350 nm, about 375 nm, about 400 nm, about 425 nm, about 450 nm, about 475 nm, about 500 nm, about 525 nm, about 550 nm, about 575 nm, about 600 nm, about 625 nm, about 650 nm, about 700 nm, about 725 nm, about 750 nm, about 775 nm, about 800 nm, about 825 nm, about 850 nm, about 875 nm, about 900 nm, about 925 nm, about 950 nm, about 975 nm, or about 1000 nm. In an embodiment, the RNA lipoplex particles have an average diameter that ranges from about 250 nm to about 700 nm. In another embodiment, the RNA lipoplex particles have an average diameter that ranges from about 300 nm to about 500 nm. In an exemplary embodiment, the RNA lipoplex particles have an average diameter of about 400 nm.

The electric charge of the RNA lipoplex particles of the present disclosure is the sum of the electric charges present in the at least one cationic lipid and the electric charges present in the RNA. The charge ratio is the ratio of the positive charges present in the at least one cationic lipid to the negative charges present in the RNA. The charge ratio of the positive charges present in the at least one cationic lipid to the negative charges present in the RNA is calculated by the following equation: charge ratio=[(cationic lipid concentration (mol))*(the total number of positive charges in the cationic lipid)]/[(RNA concentration (mol))*(the total number of negative charges in RNA)].

The spleen targeting RNA lipoplex particles described herein at physiological pH preferably have a net negative charge such as a charge ratio of positive charges to negative charges from about 1.9:2 to about 1:2. In specific embodiments, the charge ratio of positive charges to negative charges in the RNA lipoplex particles at physiological pH is about 1.9:2.0, about 1.8:2.0, about 1.7:2.0, about 1.6:2.0, about 1.5:2.0, about 1.4:2.0, about 1.3:2.0, about 1.2:2.0, about 1.1:2.0, or about 1:2.0.

RNA delivery systems have an inherent preference to the liver. This pertains to lipid-based particles, cationic and neutral nanoparticles, in particular lipid nanoparticles such as liposomes, nanomicelles and lipophilic ligands in bioconjugates. Liver accumulation is caused by the discontinuous nature of the hepatic vasculature or the lipid metabolism (liposomes and lipid or cholesterol conjugates).

For in vivo delivery of RNA to the liver, a drug delivery system may be used to transport the RNA into the liver by preventing its degradation. For example, polyplex nanomicelles consisting of a poly(ethylene glycol) (PEG)-coated surface and an mRNA-containing core is a useful system because the nanomicelles provide excellent in vivo stability of the RNA, under physiological conditions. Furthermore, the stealth property provided by the polyplex nanomicelle surface, composed of dense PEG palisades, effectively evades host immune defenses.

The RNA, RNA particles and further agents, e.g., immune checkpoint inhibitors, described herein may be administered in pharmaceutical compositions or medicaments for therapeutic or prophylactic treatments and may be administered in the form of any suitable pharmaceutical composition.

The term "pharmaceutical composition" relates to a formulation comprising a therapeutically effective agent, preferably together with pharmaceutically acceptable carriers, diluents and/or excipients. Said pharmaceutical composition is useful for treating, preventing, or reducing the severity of a disease or disorder by administration of said pharmaceutical composition to a subject. A pharmaceutical composition is also known in the art as a pharmaceutical formulation. In the context of the present disclosure, the pharmaceutical composition comprises RNA, RNA particles and/or further agents as described herein.

The pharmaceutical compositions of the present disclosure preferably comprise one or more adjuvants or may be administered with one or more adjuvants. The term "adjuvant" relates to a compound which prolongs, enhances or accelerates an immune response. Adjuvants comprise a heterogeneous group of compounds such as oil emulsions (e.g., Freund's adjuvants), mineral compounds (such as alum), bacterial products (such as Bordetella pertussis toxin), or immune-stimulating complexes. Examples of adjuvants include, without limitation, LPS, GP96, CpG oligodeoxynucleotides, growth factors, and cyctokines, such as monokines, lymphokines, interleukins, chemokines. The chemokines may be IL1, IL2, IL3, IL4, IL5, IL6, IL7, IL8, IL9, IL10, IL12, IFNα, IFNγ, GM-CSF, LT-a. Further known adjuvants are aluminium hydroxide, Freund's adjuvant or oil such as Montanide® ISA51. Other suitable adjuvants for use in the present disclosure include lipopeptides, such as Pam3Cys.

The pharmaceutical compositions according to the present disclosure are generally applied in a "pharmaceutically effective amount" and in "a pharmaceutically acceptable preparation".

The term "pharmaceutically acceptable" refers to the non-toxicity of a material which does not interact with the action of the active component of the pharmaceutical composition.

The term "pharmaceutically effective amount" or "therapeutically effective amount" refers to the amount which achieves a desired reaction or a desired effect alone or together with further doses. In the case of the treatment of a particular disease, the desired reaction preferably relates to inhibition of the course of the disease. This comprises slowing down the progress of the disease and, in particular, interrupting or reversing the progress of the disease. The desired reaction in a treatment of a disease may also be delay of the onset or a prevention of the onset of said disease or said condition. An effective amount of the compositions described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the compositions described herein may depend on various of such parameters. In the case that a reaction in a patient is insufficient with an initial dose, higher doses (or effectively higher doses achieved by a different, more localized route of administration) may be used.

The pharmaceutical compositions of the present disclosure may contain salts, buffers, preservatives, and optionally other therapeutic agents. In one embodiment, the pharmaceutical compositions of the present disclosure comprise one or more pharmaceutically acceptable carriers, diluents and/or excipients.

Suitable preservatives for use in the pharmaceutical compositions of the present disclosure include, without limitation, benzalkonium chloride, chlorobutanol, paraben and thimerosal.

The term "excipient" as used herein refers to a substance which may be present in a pharmaceutical composition of the present disclosure but is not an active ingredient. Examples of excipients, include without limitation, carriers, binders, diluents, lubricants, thickeners, surface active agents, preservatives, stabilizers, emulsifiers, buffers, flavoring agents, or colorants.

The term "diluent" relates a diluting and/or thinning agent. Moreover, the term "diluent" includes any one or more of fluid, liquid or solid suspension and/or mixing media. Examples of suitable diluents include ethanol, glycerol and water.

The term "carrier" refers to a component which may be natural, synthetic, organic, inorganic in which the active component is combined in order to facilitate, enhance or enable administration of the pharmaceutical composition. A carrier as used herein may be one or more compatible solid or liquid fillers, diluents or encapsulating substances, which are suitable for administration to subject. Suitable carrier include, without limitation, sterile water, Ringer, Ringer lactate, sterile sodium chloride solution, isotonic saline, polyalkylene glycols, hydrogenated naphthalenes and, in particular, biocompatible lactide polymers, lactide/glycolide copolymers or polyoxyethylene/polyoxy-propylene copolymers. In one embodiment, the pharmaceutical composition of the present disclosure includes isotonic saline.

Pharmaceutically acceptable carriers, excipients or diluents for therapeutic use are well known in the pharmaceutical art, and are described, for example, in Remington's Pharmaceutical Sciences, Mack Publishing Co. (A. R Gennaro edit. 1985).

Pharmaceutical carriers, excipients or diluents can be selected with regard to the intended route of administration and standard pharmaceutical practice.

In one embodiment, pharmaceutical compositions described herein may be administered intravenously, intraarterially, subcutaneously, intradermally or intramuscularly. In certain embodiments, the pharmaceutical composition is formulated for local administration or systemic administration. Systemic administration may include enteral administration, which involves absorption through the gastrointestinal tract, or parenteral administration. As used herein, "parenteral administration" refers to the administration in any manner other than through the gastrointestinal tract, such as by intravenous injection. In a preferred embodiment, the pharmaceutical compositions is formulated for systemic administration. In another preferred embodiment, the systemic administration is by intravenous administration.

The term "co-administering" as used herein means a process whereby different compounds or compositions (e.g., RNA encoding extended-PK interleukin (e.g., RNA encoding extended-PK IL2 and/or RNA encoding extended-PK IL7), RNA encoding a peptide or protein comprising an epitope and optionally an immune checkpoint inhibitor) are administered to the same patient. The RNA encoding extended-PK interleukin and the RNA encoding a peptide or protein comprising an epitope may be administered simultaneously, at essentially the same time, or sequentially. If administration takes place sequentially, the RNA encoding extended-PK interleukin may be administered before or after administration of the RNA encoding a peptide or protein comprising an epitope. If administration takes place simultaneously the RNA encoding extended-PK interleukin and the RNA encoding a peptide or protein comprising an epitope need not be administered within the same composition. The RNA encoding extended-PK interleukin and the RNA encoding a peptide or protein comprising an epitope may be administered one or more times and the number of administrations of each component may be the same or different. In addition, the RNA encoding extended-PK interleukin and the RNA encoding a peptide or protein comprising an epitope need not be administered at the same site.

The RNA, RNA particles and further agents, e.g., immune checkpoint inhibitors, described herein may be used in the therapeutic or prophylactic treatment of various diseases, in particular diseases in which provision of a peptide or protein comprising an epitope for inducing an immune response against an antigen in a subject to said subject results in a therapeutic or prophylactic effect. For example, provision of an antigen or epitope which is derived from a virus may be useful in the treatment of a viral disease caused by said virus. Provision of a tumor antigen or epitope may be useful in the treatment of a cancer disease wherein cancer cells express said tumor antigen.

In one embodiment, the present disclosure relates to a method for inducing an immune response in a subject comprising administering to the subject RNA as described herein. In an exemplary embodiment, the immune response is against cancer.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality.

In the present context, the term "treatment", "treating" or "therapeutic intervention" relates to the management and care of a subject for the purpose of combating a condition such as a disease or disorder. The term is intended to include the full spectrum of treatments for a given condition from which the subject is suffering, such as administration of the therapeutically effective compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of an individual for the purpose of combating the disease, condition or disorder and includes the administration of the active compounds to prevent the onset of the symptoms or complications.

The term "therapeutic treatment" relates to any treatment which improves the health status and/or prolongs (increases) the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

The terms "prophylactic treatment" or "preventive treatment" relate to any treatment that is intended to prevent a disease from occurring in an individual. The terms "prophylactic treatment" or "preventive treatment" are used herein interchangeably.

The terms "individual" and "subject" are used herein interchangeably. They refer to a human or another mammal (e.g. mouse, rat, rabbit, dog, cat, cattle, swine, sheep, horse or primate) that can be afflicted with or is susceptible to a disease or disorder (e.g., cancer) but may or may not have the disease or disorder. In many embodiments, the individual is a human being. Unless otherwise stated, the terms "individual" and "subject" do not denote a particular age, and thus encompass adults, elderlies, children, and newborns. In embodiments of the present disclosure, the "individual" or "subject" is a "patient".

The term "patient" means an individual or subject for treatment, in particular a diseased individual or subject.

In one embodiment of the disclosure, the aim is to provide an immune response against diseased cells expressing an antigen such as cancer cells expressing a tumor antigen, and to treat a disease such as a cancer disease involving cells expressing an antigen such as a tumor antigen.

A pharmaceutical composition comprising RNA encoding a peptide or protein comprising an epitope may be administered to a subject to elicit an immune response against an antigen comprising said epitope in the subject which may be therapeutic or partially or fully protective. A person skilled in the art will know that one of the principles of immunotherapy and vaccination is based on the fact that an immunoprotective reaction to a disease is produced by immunizing a subject with an antigen or an epitope, which is immunologically relevant with respect to the disease to be treated. Accordingly, pharmaceutical compositions described herein are applicable for inducing or enhancing an immune response. Pharmaceutical compositions described herein are thus useful in a prophylactic and/or therapeutic treatment of a disease involving an antigen or epitope.

As used herein, "immune response" refers to an integrated bodily response to an antigen or a cell expressing an antigen and refers to a cellular immune response and/or a humoral immune response. A cellular immune response includes, without limitation, a cellular response directed to cells expressing an antigen and being characterized by presentation of an antigen with class I or class II MHC molecule. The cellular response relates to T lymphocytes, which may be classified as helper T cells (also termed CD4+ T cells) that play a central role by regulating the immune response or killer cells (also termed cytotoxic T cells, CD8+ T cells, or CTLs) that induce apoptosis in infected cells or cancer cells. In one embodiment, administering a pharmaceutical composition of the present disclosure involves stimulation of an anti-tumor CD8+ T cell response against cancer cells expressing one or more tumor antigens. In as specific embodiment, the tumor antigens are presented with class I MHC molecule.

The present disclosure contemplates an immune response that may be protective, preventive, prophylactic and/or therapeutic. As used herein, "induces [or inducing] an immune response" may indicate that no immune response against a particular antigen was present before induction or it may indicate that there was a basal level of immune response against a particular antigen before induction, which was enhanced after induction. Therefore, "induces [or inducing] an immune response" includes "enhances [or enhancing] an immune response".

The term "immunotherapy" relates to the treatment of a disease or condition by inducing, or enhancing an immune response. The term "immunotherapy" includes antigen immunization or antigen vaccination.

The terms "immunization" or "vaccination" describe the process of administering an antigen to an individual with the purpose of inducing an immune response, for example, for therapeutic or prophylactic reasons.

In one embodiment, the present disclosure envisions embodiments wherein RNA formulations such as RNA lipoplex particles as described herein targeting spleen tissue are administered. The RNA encodes, for example, a peptide or protein comprising an epitope as described, for example, herein. The RNA is taken up by antigen-presenting cells in the spleen such as dendritic cells to express the peptide or protein. Following optional processing and presentation by the antigen-presenting cells an immune response may be generated against the epitope resulting in a prophylactic and/or therapeutic treatment of a disease involving the epitope or an antigen comprising the epitope. In one embodiment, the immune response induced by the RNA described herein comprises presentation of an antigen or fragment thereof, such as an epitope, by antigen presenting cells, such as dendritic cells and/or macrophages, and activation of cytotoxic T cells due to this presentation. For example, peptides or proteins encoded by the RNAs or procession products thereof may be presented by major histocompatibility complex (MHC) proteins expressed on antigen presenting cells. The MHC peptide complex can then be recognized by immune cells such as T cells or B cells leading to their activation.

Accordingly, the present disclosure relates to RNA as described herein for use in a prophylactic and/or therapeutic treatment of a disease involving an antigen, preferably a cancer disease.

The term "macrophage" refers to a subgroup of phagocytic cells produced by the differentiation of monocytes. Macrophages which are activated by inflammation, immune cytokines or microbial products nonspecifically engulf and kill foreign pathogens within the macrophage by hydrolytic and oxidative attack resulting in degradation of the pathogen. Peptides from degraded proteins are displayed on the macrophage cell surface where they can be recognized by T cells, and they can directly interact with antibodies on the B cell surface, resulting in T and B cell activation and further stimulation of the immune response. Macrophages belong to the class of antigen presenting cells. In one embodiment, the macrophages are splenic macrophages.

The term "dendritic cell" (DC) refers to another subtype of phagocytic cells belonging to the class of antigen presenting cells. In one embodiment, dendritic cells are derived from hematopoietic bone marrow progenitor cells. These progenitor cells initially transform into immature dendritic cells. These immature cells are characterized by high phagocytic activity and low T cell activation potential. Immature dendritic cells constantly sample the surrounding environment for pathogens such as viruses and bacteria. Once they have come into contact with a presentable antigen, they become activated into mature dendritic cells and begin to migrate to the spleen or to the lymph node. Immature dendritic cells phagocytose pathogens and degrade their proteins into small pieces and upon maturation present those fragments at their cell surface using MHC molecules. Simultaneously, they upregulate cell-surface receptors that act as co-receptors in T cell activation such as CD80, CD86, and CD40 greatly enhancing their ability to activate T cells. They also upregulate CCR7, a chemotactic receptor that induces the dendritic cell to travel through the blood stream to the spleen or through the lymphatic system to a lymph node. Here they act as antigen-presenting cells and activate helper T cells and killer T cells as well as B cells by presenting them antigens, alongside non-antigen specific co-stimulatory signals. Thus, dendritic cells can actively induce a T cell- or B cell-related immune response. In one embodiment, the dendritic cells are splenic dendritic cells.

The term "antigen presenting cell" (APC) is a cell of a variety of cells capable of displaying, acquiring, and/or presenting at least one antigen or antigenic fragment on (or at) its cell surface. Antigen-presenting cells can be distinguished in professional antigen presenting cells and non-professional antigen presenting cells.

The term "professional antigen presenting cells" relates to antigen presenting cells which constitutively express the Major Histocompatibility Complex class II (MHC class II) molecules required for interaction with naive T cells. If a T cell interacts with the MHC class II molecule complex on the membrane of the antigen presenting cell, the antigen presenting cell produces a co-stimulatory molecule inducing activation of the T cell. Professional antigen presenting cells comprise dendritic cells and macrophages.

The term "non-professional antigen presenting cells" relates to antigen presenting cells which do not constitutively express MHC class II molecules, but upon stimulation by certain cytokines such as interferon-gamma. Exemplary, non-professional antigen presenting cells include fibroblasts, thymic epithelial cells, thyroid epithelial cells, glial cells, pancreatic beta cells or vascular endothelial cells.

"Antigen processing" refers to the degradation of an antigen into procession products, which are fragments of said antigen (e.g., the degradation of a protein into peptides) and the association of one or more of these fragments (e.g., via binding) with MHC molecules for presentation by cells, such as antigen presenting cells to specific T cells.

The term "disease involving an antigen" or "disease involving an epitope" refers to any disease which implicates an antigen or epitope, e.g. a disease which is characterized by the presence of an antigen or epitope. The disease involving an antigen or epitope can be an infectious disease, or a cancer disease or simply cancer. As mentioned above, the antigen may be a disease-associated antigen, such as a tumor-associated antigen, a viral antigen, or a bacterial antigen and the epitope may be derived from such antigen.

The term "infectious disease" refers to any disease which can be transmitted from individual to individual or from organism to organism, and is caused by a microbial agent (e.g. common cold). Infectious diseases are known in the art and include, for example, a viral disease, a bacterial disease, or a parasitic disease, which diseases are caused by a virus, a bacterium, and a parasite, respectively. In this regard, the infectious disease can be, for example, hepatitis, sexually transmitted diseases (e.g. chlamydia or gonorrhea), tuberculosis, HIV/acquired immune deficiency syndrome (AIDS), diphtheria, hepatitis B, hepatitis C, cholera, severe acute respiratory syndrome (SARS), the bird flu, and influenza.

The terms "cancer disease" or "cancer" refer to or describe the physiological condition in an individual that is typically characterized by unregulated cell growth. Examples of cancers include, but are not limited to, carcinoma, lymphoma, blastoma, sarcoma, and leukemia. More particularly, examples of such cancers include bone cancer, blood cancer lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma. The term "cancer" according to the disclosure also comprises cancer metastases.

Combination strategies in cancer treatment may be desirable due to a resulting synergistic effect, which may be considerably stronger than the impact of a monotherapeutic approach. In one embodiment, the pharmaceutical composition is administered with an immunotherapeutic agent. As used herein "immunotherapeutic agent" relates to any agent that may be involved in activating a specific immune response and/or immune effector function(s). The present disclosure contemplates the use of an antibody as an immunotherapeutic agent. Without wishing to be bound by theory, antibodies are capable of achieving a therapeutic effect against cancer cells through various mechanisms, including inducing apoptosis, block components of signal transduction pathways or inhibiting proliferation of tumor cells. In certain embodiments, the antibody is a monoclonal antibody. A monoclonal antibody may induce cell death via antibody-dependent cell mediated cytotoxicity (ADCC), or bind complement proteins, leading to direct cell toxicity, known as complement dependent cytotoxicity (CDC). Non-limiting examples of anti-cancer antibodies and potential antibody targets (in brackets) which may be used in combination with the present disclosure include: Abagovomab (CA-125), Abciximab (CD41), Adecatumumab (EpCAM), Afutuzumab (CD20), Alacizumab pegol (VEGFR2), Altumomab pentetate (CEA), Amatuximab (MORAb-009), Anatumomab mafenatox (TAG-72), Apolizumab (HLA-DR), Arcitumomab (CEA), Atezolizumab (PD-L1), Bavituximab (phosphatidylserine), Bectumomab (CD22), Belimumab (BAFF), Bevacizumab (VEGF-A), Bivatuzumab mertansine (CD44 v6), Blinatumomab (CD 19), Brentuximab vedotin (CD30 TNFRSF8), Cantuzumab mertansin (mucin CanAg), Cantuzumab ravtansine (MUC1), Capromab pendetide (prostatic carcinoma cells), Carlumab (CNT0888), Catumaxomab (EpCAM, CD3), Cetuximab (EGFR), Citatuzumab bogatox (EpCAM), Cixutumumab (IGF-1 receptor), Claudiximab (Claudin), Clivatuzumab tetraxetan (MUC1), Conatumumab (TRAIL-R2), Dacetuzumab (CD40), Dalotuzumab (insulin-like growth factor I receptor), Denosumab (RANKL), Detumomab (B-lymphoma cell), Drozitumab (DR5), Ecromeximab (GD3 ganglioside), Edrecolomab (EpCAM), Elotuzumab (SLAMF7), Enavatuzumab (PDL192), Ensituximab (NPC-1C), Epratuzumab (CD22), Ertumaxomab (HER2/neu, CD3), Etaracizumab (integrin $\alpha v\beta 3$), Farletuzumab (folate receptor 1), FBTA05 (CD20), Ficlatuzumab (SCH 900105), Figitumumab (IGF-1 receptor), Flanvotumab (glycoprotein 75), Fresolimumab (TGF-13), Galiximab (CD80), Ganitumab (IGF-I), Gemtuzumab ozogamicin (CD33), Gevokizumab (ILI$\beta$), Girentuximab (carbonic anhydrase 9 (CA-IX)), Glembatumumab vedotin (GPNMB), Ibritumomab tiuxetan (CD20), Icrucumab (VEGFR-1), Igovoma (CA-125), Indatuximab ravtansine (SDC1), Intetumumab (CD51), lnotuzumab ozogamicin (CD22), Ipilimumab (CD 152), Iratumumab (CD30), Labetuzumab (CEA), Lexatumumab (TRAIL-R2), Libivirumab (hepatitis B surface antigen), Lintuzumab (CD33), Lorvotuzumab mertansine (CD56), Lucatumumab (CD40), Lumiliximab (CD23), Mapatumumab (TRAIL-R1), Matuzumab (EGFR), Mepolizumab (IL5), Milatuzumab (CD74), Mitumomab (GD3 ganglioside), Mogamulizumab (CCR4), Moxetumomab pasudotox (CD22), Nacolomab tafenatox (C242 antigen), Naptumomab estafenatox (5T4), Namatumab (RON), Necitumumab (EGFR), Nimotuzumab (EGFR), Nivolumab (IgG4), Ofatumumab (CD20), Olaratumab (PDGF-R a), Onartuzumab (human scatter factor receptor kinase), Oportuzumab monatox (EpCAM), Oregovomab (CA-125), Oxelumab (OX-40), Panitumumab (EGFR), Patritumab (HER3), Pemtumoma (MUC1), Pertuzuma (HER2/neu), Pintumomab (adenocarcinoma antigen), Pritumumab (vimentin), Racotumomab (N-glycolylneuraminic acid), Radretumab (fibronectin extra domain-B), Rafivirumab (rabies virus glycoprotein), Ramucirumab (VEGFR2), Rilotumumab (HGF), Rituximab (CD20), Robatumumab (IGF-1 receptor), Samalizumab (CD200), Sibrotuzumab (FAP), Siltuximab (IL6), Tabalumab (BAFF), Tacatuzumab tetraxetan (alpha-fetoprotein), Taplitumomab paptox (CD 19), Tenatumomab (tenascin C), Teprotumumab (CD221), Ticilimumab (CTLA-4), Tigatuzumab (TRAIL-R2), TNX-650 (IL13), Tositumomab (CD20), Trastuzumab (HER2/neu), TRBS07 (GD2), Tremelimumab (CTLA-4), Tucotuzumab celmoleukin (EpCAM), Ublituximab (MS4A1), Urelumab (4-1 BB), Volociximab (integrin $\alpha 5\beta 1$), Votumumab (tumor antigen CTAA 16.88), Zalutumumab (EGFR), and Zanolimumab (CD4).

In another aspect, the invention provides a method of delivering a cytokine to a target organ or target tissue in a subject comprising administering to the subject RNA encoding a cytokine in a formulation for preferential delivery of RNA to said target organ or tissue. The cytokine may be any cytokine, in particular any therapeutically useful cytokine, including cytokine fragments and variants, and also including fusion proteins of cytokines, cytokine fragments and cytokine variants, such as extended-PK cytokines, in particular extended-PK interleukins, such as those described herein.

In one embodiment, the target organ is the lymphatic system, in particular secondary lymphoid organs, more specifically spleen, and the target tissue is tissue of the lymphatic system, in particular tissue of secondary lymphoid organs, more specifically spleen tissue. The delivery of a cytokine to such target tissue is preferred, in particular, if presence of the cytokine in this organ or tissue is desired (e.g., for inducing an immune response, in particular in case cytokines are required during T-cell priming or for activation of resident immune cells), while it is not desired that the cytokine is present systemically, in particular in significant amounts (e.g., because the cytokine has systemic toxicity).

Accordingly, in another aspect, the invention provides a method of inducing an immune response in a subject comprising administering to the subject:

a. RNA encoding a cytokine and b. RNA encoding a peptide or protein comprising an epitope for inducing an immune response against an antigen in said subject, wherein the RNA encoding a cytokine and the RNA encoding a peptide or protein comprising an epitope are delivered to the lymphatic system, in particular secondary lymphoid organs, more specifically spleen.

In one embodiment, the RNA encoding a cytokine and the RNA encoding a peptide or protein comprising an epitope are administered in a (common or separate) formulation for targeting the lymphatic system, in particular a formulation for targeting secondary lymphoid organs, more specifically for targeting spleen. Such formulations are described herein above. Examples of suitable cytokines include IL12, IL15, IFN-α, or IFN-β, fragments and variants thereof, and fusion proteins of these cytokines, fragments and variants, such as extended-PK cytokines, such as those described herein. Particularly preferred examples of suitable cytokines are cytokines involved in T cell priming.

In another embodiment of the method of delivering a cytokine to a target organ or target tissue in a subject, the target organ is liver and the target tissue is liver tissue. The delivery of a cytokine to such target tissue is preferred, in particular, if presence of the cytokine in this organ or tissue is desired and/or if it is desired to express large amounts of the cytokine and/or if systemic presence of the cytokine, in particular in significant amounts, is desired or required.

In one embodiment, the RNA encoding a cytokine is administered in a formulation for targeting liver. Such formulations are described herein above. Examples of suitable cytokines include IL2 or IL7, fragments and variants thereof, and fusion proteins of these cytokines, fragments and variants, such as extended-PK cytokines, such as those described herein. Particularly preferred examples of suitable cytokines are cytokines involved in T cell proliferation and/or maintenance.

The present disclosure also comprises methods of delivering one or more cytokines, wherein a cytokine is delivered to a first target organ or target tissue in a subject comprising administering to the subject RNA encoding a cytokine in a formulation for preferential delivery of RNA to said first target organ or tissue and the same or a different cytokine is delivered to a second target organ or target tissue in a subject comprising administering to the subject RNA encoding a cytokine in a formulation for preferential delivery of RNA to said second target organ or tissue. In one embodiment, the first target organ is the lymphatic system, in particular secondary lymphoid organs, more specifically spleen, and the first target tissue is tissue of the lymphatic system, in particular tissue of secondary lymphoid organs, more specifically spleen tissue and the second target organ is liver and the second target tissue is liver tissue. Administration for delivery of a cytokine to a first target organ or target tissue and administration for delivery of a cytokine to a second target organ or target tissue may be simultaneously, at essentially the same time, or sequentially. Cytokines for preferential targeting of the lymphatic system, in particular secondary lymphoid organs, more specifically spleen, and tissue of the lymphatic system, in particular tissue of secondary lymphoid organs, more specifically spleen tissue as well as cytokines for preferential targeting of liver and liver tissue are described above. The methods of delivering one or more cytokines to different target organs or tissues may provide a first cytokine involved in T cell priming in the lymphatic system and a second cytokine involved in T cell proliferation and/or maintenance systemically. The methods of delivering one or more cytokines to different target organs or tissues may also involve administration of RNA encoding a peptide or protein comprising an epitope for inducing an immune response against an antigen in a subject as described above.

Citation of documents and studies referenced herein is not intended as an admission that any of the foregoing is pertinent prior art. All statements as to the contents of these documents are based on the information available to the applicants and do not constitute any admission as to the correctness of the contents of these documents.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

EXAMPLES

Example 1: Construct Design and Validation

Construct Design and mRNA Production

In vitro transcription of cytokine encoding mRNAs were based on the pST4-T7-GG-TEV-MCS-FI-A30LA70 plasmid-backbones and derivative DNA-constructs. These plasmid constructs contain the 5' leader sequence of tobacco etch virus (TEV), a 3' FI element (where F is a 136 nucleotide long 3'-UTR fragment of amino-terminal enhancer of split, mRNA and I is a 142 nucleotide long fragment of mitochondrially encoded 12S RNA both identified in Homo sapiens; WO 2017/060314) and a poly(A) tail of 100 nucleotides, with a linker after 70 nucleotides. Cytokine and Alb coding sequences originate from Mus musculus and no changes in the resulting amino acid sequences were introduced (mIL2: NP_032392.1; mIFNβ: NP_034640.1; mIL7: NP_032397.1; mIL15Rα: NP_032384.1; mIL15: NP_032383.1). Encoded proteins are equipped with an N-terminal signal peptide (SP) that is the native SP of the respective protein. In case of fusion proteins, only the SP of the N-terminal moiety was maintained, for further moieties only the mature portion (protein without SP) was encoded. The stop-codon was maintained for the most C-terminal moiety only. Different protein moieties in the cytokine and Alb fusion constructs were separated by a 30-nucleotide long linker sequence encoding for glycine and serine residues. In case of mouse (m) IL15sushi a fusion protein between the coding sequence of the first 103 amino acids (including SP) of mIL15Rα and the mature domain of mIL15 was used. In this fusion protein the mIL15Rα portion defines the N-terminus and is separated by a 60-nucleotide linker that encodes for glycine and serine residues. The sequence of secreted nano-luciferase (sec-nLUC) was purchased (Promega) and sub-cloned in the above described plasmid-backbone. For the fusion of sec-nLUC and mAlb the stop-codon of sec-nLUC was deleted and the mature domain of mAlb was fused to the C-terminus of sec-nLUC separated by a 30-nucleotide long linker sequence encoding for glycine and serine residues. mRNA was generated by in vitro transcription as described by Kreiter et al. (Kreiter, S. et al. Cancer Immunol. Immunother. 56, 1577-87 (2007)) with substitution of the normal nucleoside uridine by 1-methyl-pseudouridine. Resulting mRNAs were equipped with a Cap1-structure and double-stranded (dsRNA) molecules were depleted by cellulose purification. Purified mRNA was eluted in $H_2O$ and stored at −80° C. until further use. In vitro transcription of all described mRNA constructs was carried out at BioNTech RNA Pharmaceuticals GmbH.

Construct Validation

Figure 1:
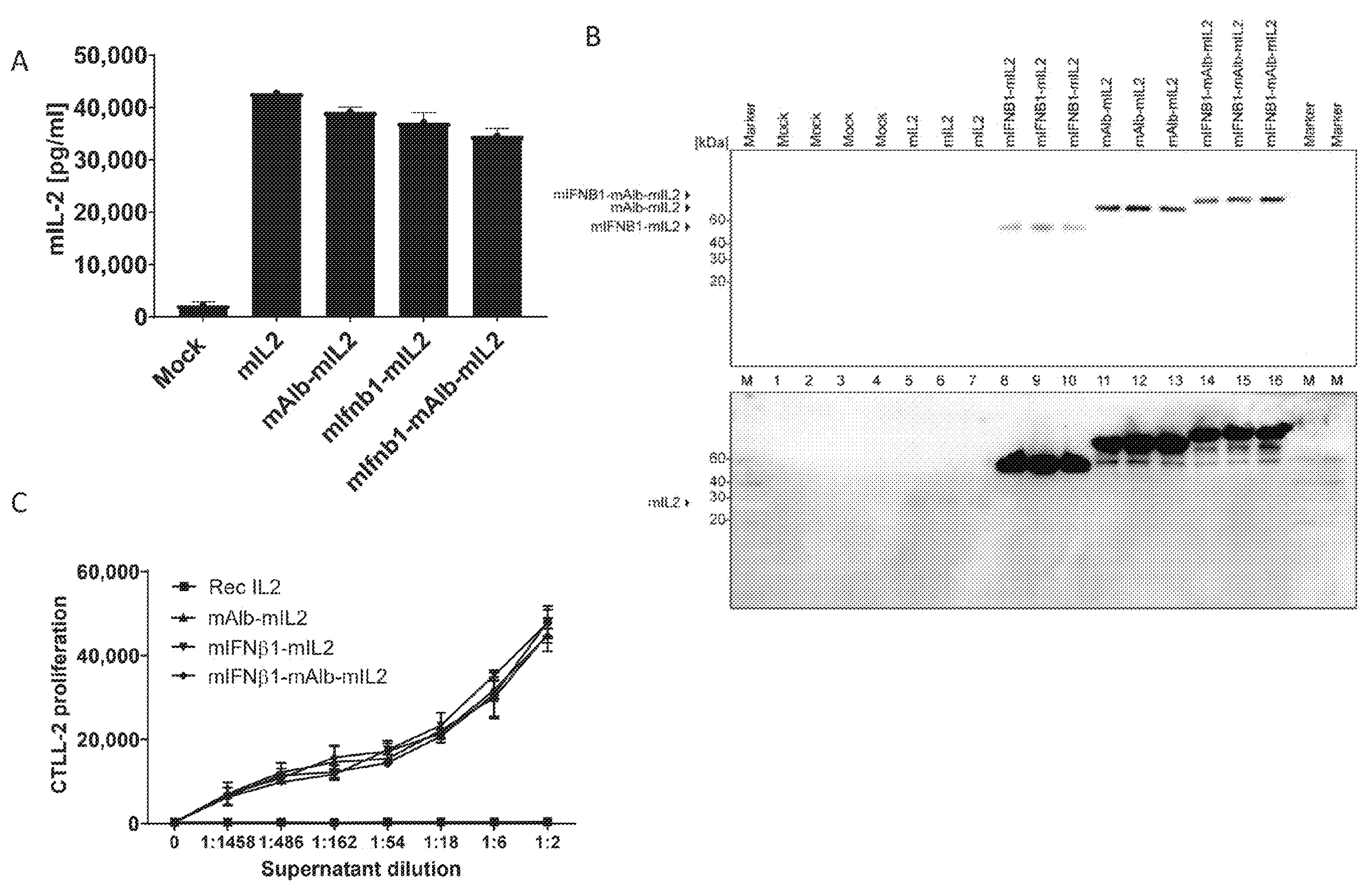
FIG. 1: Validation of mIL2 encoding constructs.

Cytokine expression from the generated mRNAs was controlled by lipofection of the mRNA into HEK-293T-17 cells and subsequent enzyme-linked immunosorbent assay (ELISA) analysis of the supernatant (FIG. 1A, FIG. 2A, FIG. 3A, FIG. 4A). mRNA was formulated under sterile and RNase-free conditions using Lipofectamine MessengerMax (Thermo Fisher Scientific). Here, 125 or 250 ng mRNA/μl Lipofectamine MessengerMax were complexed and used per square centimeter culture dish for lipofection of HEK-293T-17 cells of approximately 80% confluence. Supernatants were collected after 24 h of expression under sterile conditions and stored at −80° C. until further use. Cytokine presence in respective cell culture supernatants were determined using commercially available ELISA kits specific for the respective cytokine (Biolegend, R&D systems). ELISA analysis was performed according to manufacturers' protocols. The same supernatants were used for Western Blot analysis to semi-quantitatively determine protein concentrations under denaturing conditions, because epitopes for ELISA antibodies frequently appeared inaccessible in fusion proteins as long as proteins remained in a native folding state (FIG. 1B, FIG. 2B, FIG. 3B, FIG. 4B). Therefore, total protein was concentrated using appropriate VivaSpin columns (Sartorious AG) and concentrations were assessed by quantification of prominent bands after sample separation on SDS-PAGE and Coomassie staining using Image Quant TL software (GE Healthcare). For Western blotting homogenous protein amounts were separated by SDS-PAGE and transferred on nitrocellulose membrane by semi-dry or wet-blot protocols. After blotting nitrocellulose membranes were blocked (5% non-fat dry milk in 1×PBS-T) followed by incubation with appropriate dilutions of primary (anti-mIL2: BioLegend (BLD-503701), anti-mIL15: R&D Systems (MAB447-SP), anti-mIFNβ: Abcam (ab151605); anti-mIL7: Thermo Scientific (PA5-46944)) and secondary antibody. The membranes were washed (1×PBS-T) before and after secondary antibody incubation. Chemiluminescent signals developing after addition of the Lumi-Light Western Blotting Substrate (Roche), SuperSignal®West Dura Extended Duration Substrate (Thermo Fisher Scientific) or Trident femto Western HRP Substrate (Gene Tex) were recorded using the LAS 4000 system (GE Healthcare). Biological activity of expressed cytokines was tested by suitable activity assays. The activity of mIL2 and mIL15sushi was assayed by analyzing the cytokine dependent proliferation of murine CTLL-2 cells (Mouse C57b1/6 T cells, Sigma-Aldrich) (FIG. 1C, FIG. 2C). CTLL-2 proliferation was monitored in dependence of either of the two cytokines upon CTLL-2 cultivation in the presence of HEK-293T-17 supernatants harvested after expression of the respective cytokine mRNAs or after expression of mRNA encoding for Alb only. The CellTiter-Glo Luminescent Cell Viability Assay (Promega) was used to determine the amount of cells after 72 h of the respective treatment. Recombinant human (h) IL2 and IL15sushi proteins were used as controls. The biological activity of mRNAs encoding mIL7 was tested by analyzing the capacity to induce CD4+ T-cell proliferation in carboxyfluorescein succinimidyl ester (CFSE) labelled, anti-CD3 activated PBMC populations upon cultivation in the presence of HEK-293T-17 supernatants harvested after expression of mIL7 encoding mRNAs (FIG. 3C). T-cell proliferation was analyzed by CFSE monitoring using flow cytometry after anti-CD4-PE and anti-CD8-PE-Cy7 staining. Recombinant mIL7 protein was used as a control. The biological activity of mRNAs harbouring murine IFNß moieties was confirmed by investigating the capacity of the respectively expressed protein products to upregulate MHC class I expression on murine colon carcinoma cells (CT26) (FIG. 4C). CT26 cells were cultivated in the presence of HEK293T-17 supernatants harvested after expression of mIFNß encoding mRNAs. Recombinant mIFNß served as a control. Surface levels of MHC class I on CT26 cells before and after the treatment was assessed by MHC class I staining with FITC coupled H2-$K^b$ antibody and subsequent flow cytometry analysis. Expression of sec-nLUC and luciferase activity of the resulting gene-products was determined in supernatants of HEK-293T-17 after 24 h of expression of sec-nLUC encoding mRNAs using the Nano-Glo Luciferase Assay System (Promega) according to manufatures' protocols (FIG. 4D). Supernatants of HEK-293T-17 lipofected in the absence of mRNA (Mock) served as control.

Example 2: Systemic Availability of Cytokines Fused to Albumin and Encoded on Nucleoside-Modified mRNA Strength and duration of systemic bioavailability of unaltered compared to albumin-fused cytokines were investigated by measuring cytokine levels in the blood circulation. Female C57BL/6 (9 weeks old) (n=3 mice per group and time-point) were purchased from Envigo and injected with 3 μg unaltered or mAlb-fusion protein-encoding mRNA formulated with TransIT (Mirrus) intravenously (i.v.). Mice received either mIL2 or mIL2 fused to mAlb (mAlb-mIL2), murine interferon-β (mIFNβ) or mIFNβ fused to mAlb (mIFNβ-mAlb), mIL2 coupled to mIFNβ (mIFNβ-mIL2) or mIL2 coupled to mIFNβ and fused to mAlb (mIFNβ-mAlb-mIL2), or control mRNA encoding mAlb only. Blood was retrieved and serum prepared 6, 24 and 48 h and 5 days after injection. Optical density at 450 nm was determined by standard ELISA kits (Biolegend, PBL Assay Science) according to the manufacturer's instructions and measurement of substrate activity using the Infinite M200 plate reader (Tecan). As shown in FIG. 5, fusion of mAlb to mIL2 or mIFNβ increases and prolongs systemic availability. Double fusions of mAlb with IFNβ and mIL2 do not enhance mIL2 presence but do promote higher amounts of mIFNβ in the circulation.

Example 3: Expansion of Immune Cell Subsets in the Spleen by mAlb-mIL2

The implications of extended cytokine availability, especially of mIL2, on the composition of immune cell subsets was determined in the spleen as a major immunorelevant organ. Following the experimental setup described in Example 2, spleens were harvested five days after mRNA injection, weighed, and single-cell suspensions prepared by mashing organs through cell strainers and hypotonic lysis of erythrocytes. For single-cell analysis by flow cytometry, $5 \times 10^6$ splenocytes were stained for viability using fixable viability dye (Ebioscience) for 15 min at 2-8° C., followed by T, B and NK cells using antibodies specific for CD8, CD19, CD25 and NK1.1 (all BD Biosciences) and CD4

(Biolegend) for 30 min at 2-8° C. In order to determine absolute cell numbers, cells were transferred into Trucount® tubes (BD Biosciences). Flow cytometric data were acquired on a FACSCanto II flow cytometer (BD Biosciences) and analyzed with FlowJo 7.6.5 software (Tree Star). Immune cell subsets were determined by exclusion of doublets and dead cells and subsequent gating for NK1.1+ CD19− (NK cells), NK1.1− CD19+ (B cells), NK1.1− CD19− CD8+ (CD8+ T cells), NK1.1− CD19− CD4+ (CD4+ T cells), and NK1.1− CD19− CD4+ CD25+ (CD4+ CD25+ T cells). Cells in gates were quantified by relating their cell counts to the number of Trucount® beads measured in the same sample. Results were depicted and statistics (one-way ANOVA followed by Dunnett's multiple comparison test) analyzed using GraphPad Prism 7. In FIG. 6A, absolute cell numbers per spleen are visualized, and FIG. 6B shows spleen weights (mean±standard error of mean (s.e.m.)). Fusion of mAlb to mIL2 was able to significantly expand CD4+ T cells, CD4+ CD25+ T cells, CD8+ T cells, B cells and NK cells over mAlb, while unaltered mIL2 increased cell numbers but the differences were not significant. Neither mouse IFN-β (mIFNβ) nor mIFNβ-mAlb induced proliferation of these cell subsets, as expected. Not surprisingly, fusion of mIFNβ to mIL2 led to intermediate expansion of cell subsets, with mIFNβ limiting the proliferative capacity of both mIL2 and mAlb-mIL2. Correspondingly, spleens were highly enlarged in the group treated with mAlb-mIL2 and to a lesser extent with mIFNI3-mAlb-mIL2, albeit not significantly.

Example 4: Activation of Immune Cell Subsets in the Spleen

Providing an adequate stimulatory environment in addition to antigen is one critical prerequisite for mounting robust and long-lasting T-cell immunity. We previously showed that type I IFN (IFNα and IFNβ) is able to activate splenic immune cell subsets via auto- or paracrine signaling through the IFNα/β receptor (IFNAR) (Kranz, L. M. et al. Nature 534, 396-401 (2016)), causing antigen-presenting dendritic cells (DC) and effector cells to selectively upregulate a set of activation markers. In order to determine the change in marker expression mediated by increased presence of mIFNβ, splenocytes derived 24 h after injection of unaltered or albumin-fused cytokines from the experiment described in Example 2 were stained for viability using fixable viability dye (Ebioscience) for 15 min at 2-8° C., followed by DC, NK and T cells with antibodies specific for CD11c (Miltenyi), CD11b, CD3, CD40, CD69, NK1.1 (all BD Biosciences) and CD86 (Biolegend). Flow cytometric data were acquired on a FACSCanto II flow cytometer (BD Biosciences) and analyzed with FlowJo 7.6.5 software (Tree Star). Immune cell subsets were determined by exclusion of doublets and dead cells and subsequent gating for NK1.1+ CD3− (NK cells), NK1.1− CD3+ (T cells), and NK1.1− CD3− CD11c+ CD11b$^{int}$ (DC). Results were depicted and statistics (one-way ANOVA followed by Dunnett's multiple comparison test) analyzed using GraphPad Prism 6. As shown in FIG. 7, all mRNA-encoded proteins containing mIFNI3 were able to induce similar and significant upregulation of activation markers CD40, CD69 and CD86 on DC. mIFNβ and mIFNβ-mAlb were superior in mediating expression of CD69 on NK and T cells, compared to mIFNβ-m IL2 or mIFNβ-mAlb-m IL2.

Example 5: Prolongation of Protein Availability in the Blood, Tumor and Tumor-Draining Lymph Node by Fusion with mAlb In order to visualize how fusion of cytokines to mAlb changed their biodistribution and especially their availability in the tumor tissue and tumor-draining lymph node, a secreted variant of NanoLuc® luciferase (sec-nLUC) was fused to mAlb or not and encoded on nucleoside-modified mRNA. In the presence of oxygen, its substrate furimazine is converted into furimamide, carbon dioxide and light, of which the latter can be measured by conventional luminescence readers. Female BALB/c (6-9 weeks) mice (n=3 mice per group and time-point) were purchased from Janvier Labs and injected with 5×10$^5$ CT26 tumor cells (ATCC CRL-2638 lot no. 58494154) in 100 µl PBS subcutaneously (s.c.) into the right flank. On day 24, mice were treated with 3 µg sec-nLUC, sec-nLUC fused to mAlb (sec-nLUC-mAlb), all formulated with TransIT (Mirrus) i.v., or remained untreated (control). Blood was retrieved and serum prepared 2, 6, 24, 48 and 72 h after injection. Liver, tumor, tumor-draining inguinal and non-tumor draining inguinal lymph nodes were isolated, weighed, transferred to 2 ml plastic tubes with 1.4 mm and 2.8 mm ceramic balls (Bertin Instruments) and cryoconserved in isopentane submerged in liquid nitrogen 6, 24, 48 and 72 h after injection. The control group was sacrificed at 2 h and data received from this group were used for time-point 0. Tissue lysates were prepared from samples stored at −80° C. Briefly, tissue samples were thawed at 20-25° C. DPBS-Buffer (Gibco) supplemented with 1× Halt™ Protease and Phosphatase Inhibitor Cocktail (Thermo Scientific) was added and tissues were homogenized using Precellys®24 Dual homogenizer (Bertin Instruments). Lysates were cleared by centrifugation and supernatants were transferred into clean chilled Eppendorf tubes and stored on ice. Protein concentration in the lysates was measured using Pierce™ BCA Protein Assay Kit (Thermo Scientific) according to the manufacturer's instructions. Afterwards lysates were snap-frozen in liquid nitrogen and stored at −80° C. Nano-Glo® Luciferase Assay (Promega) was performed with 30 µg protein or 50 µl serum according to the manufacturer's instructions using the Infinite M200 plate reader (Tecan). Bioluminescence intensities are depicted in FIG. 8. Unaltered sec-nLUC was hardly or not at all detected at any of the selected time-points. mAlb fusion, however, raises and prolonged systemic (serum) and intratumoral availability, with high levels of reporter protein still present even 72 h after injection. Similarly, fusion with mAlb provided accumulation of protein in the tumor-draining lymph node. Expression in the liver was mainly prolonged rather than increased. The presence of mAlb in the target organ seems to be irrelevant initially; the extent of translation of the injected mRNA is dependent on the formulation and its rate of transfection alone, while mAlb stabilizes the translated protein and ensures high availability in the periphery.

Example 6: Therapeutic Efficacy of Albumin Fused Cytokines in Combination with mRNA Vaccination and PD-L1 Blockade Therapeutic efficacy of selected cytokine albumin fusion constructs was tested in the mouse colon cancer model CT26. 6-9 week old BALB/c mice were purchased from Janvier Labs and injected with 5×10$^5$ CT26 tumor cells (ATCC CRL-2638 lot no. 58494154) in 200 µl PBS s.c. into the right flank. Ten days later, mice were treated with gp70 mRNA lipoplexes (RNA-LPX) (Kreiter, S. et al. Nature 520, 692-696 (2015); Kranz, L. M. et al. Nature 534, 396-401 (2016)) vaccination (20 µg i.v.) and an anti-PD-L1 blocking antibody (clone 6E11, mIgG2A, L234A, L235A, P329G; Genentech; 200 µg intraperitoneally (i.p.) on first treatment, 100 µg i.p. on second to last treatment). Two days after each vaccination/antibody treatment, 1 μg Albumin fusion protein-encoding mRNA formulated in TransIT (Mirrus) was injected i.v. Mice received either albumin fused to murine Interleukin-2 (mAlb-IL2), murine Interferon-β (mIFNβ-mAlb), interleukin-2 coupled with interferon-β (mIFNβ-mAlb-mIL2), murine interleukin-7 (mIL7-mAlb), mouse interleukin-15 fused to the interleukin-15 receptor α (mIL15sushi-mAlb) or control mRNA encoding murine albumin (mAlb) only. The treatment schedule was repeated weekly as depicted in the upper panel of FIG. 9. Tumor volume was measured every two or three days with a caliper, calculated using the formula $(A \times B^2)/2$ (A as the largest and B the smallest diameter of the tumor) and depicted using Graph Pad Prism 6. As shown in FIG. 9, the constructs mAlb-IL2, mIFNβ-mAlb-m IL2 and mIL7-mAlb were able to boost the therapeutic efficacy of vaccination and PD-L1 blockade leading to tumor rejection in 63%, 50% and 75% of mice, respectively.

Example 7: Influence of Cytokine Albumin Fusions on the Abundance of Vaccine Induced T Cells Next, we analyzed whether injection of fusion protein-encoding mRNA would boost vaccine induced T-cell responses specific for CT26 tumors. CT26-WT tumor bearing mice depicted in FIG. 9 were analyzed by flow cytometry for gp70 AH1 tetramer+ CD8+ T cells in blood 7 days after the first treatment (day 17 after tumor inoculation). For this, peripheral blood of mice was collected from the orbital sinus. 50 μl of blood was stained for 30 min at 2-8° C. with an H-2Ld/AH1$_{423-431}$ (SPSYVYHQF) tetramer (MBL) and antibodies specific for CD45 and CD8 (BD). Blood was lysed using lysing solution (BD FACS™). In order to determine absolute cell numbers, cells were transferred into Trucount® tubes (BD). Flow cytometric data were acquired on a FACSCanto II or a FACSCelesta flow cytometer (both BD Biosciences) and analyzed with FlowJo X software (Tree Star). Gp70 AH1 specific T cells were quantified by gating on CD45+ CD8+ Tetramer+ lymphocytes. Cells in gates were quantified by relating their cell counts to the number of Trucount® beads measured in the same sample. Results were depicted and statistics (one-way ANOVA followed by Dunnett's multiple comparison test) analyzed using GraphPad Prism 6. In FIG. 10 absolute numbers per μl blood (left) and the fraction of tetramer+ cells among CD8+ T cells (right) are depicted (mean+/−standard error of mean (s.e.m.)). mAlb-IL2 administration was able to significantly boost gp70 specific T-cell numbers and frequencies by several fold very quickly 7 days after the first vaccination. Although with a slower kinetic, also mIFNβ-mAlb-mIL2, mIL7-mAlb and mIL15sushi-mAlb were able to increase gp70 specific T-cell numbers over time, as shown in FIG. 11. Measurements shown in FIG. 11 were performed similar as described for FIG. 10. Noteworthy, only mAlb-IL2 increased especially gp70 specific T-cell numbers over non-specific tetramer negative CD8+ T cells as shown in FIG. 12 (mean±s.e.m.). mIFNβ-mAlb-mIL2, mIL7-mAlb and mIL15sushi-mAlb boosted tetramer negative and tetramer positive cells to a similar extent. Statistical significance of FIG. 12 was determined using a one-way ANOVA followed by Sidaks's multiple comparison test. Plotting the number of tetramer positive cells per μl blood against the tumor size on each measurement day clearly shows a statistically significant (spearman's rank correlation coefficient) negative correlation (FIG. 13). This indicates that higher numbers of gp70 tumor antigen specific T cells result in lower tumor volumes, i.e. improved tumor control.

Example 8: Influence of Cytokine Albumin Fusions on the Abundance of Regulatory T Cells In addition to supporting effector T-cell function and proliferation, IL2 is a known inducer of regulatory T cells (Tregs). Tregs are a subset of CD4+ T cells which are known to suppress the function of anti-tumor CD8+ and CD4+ T cells (Nishikawa, H. & Sakaguchi, S., Curr. Opin. Immunol. 27, 1-7 (2014)). Subsequently, we tested whether mRNA encoding cytokine albumin fusions would alter the number of CD4+ T cells and among those the fraction of unwanted Tregs. Peripheral blood of mice from FIG. 9 was collected from the orbital sinus 31 days after tumor inoculation. 50 μl of blood was stained for 30 min at 2-8° C. with antibodies specific for CD45, CD8 (BD), CD25 and CD4 (eBioscience). Then, blood was lysed using lysing solution (BD FACS™). Fixation/permeabilization buffers from eBioscience (Foxp3/Transcription Factor Staining Buffer Set) were used for intracellular staining of FoxP3. After permeabilization, a FoxP3 (eBioscience) specific antibody was added for 30 min at 2-8° C. Absolute cell numbers were determined using Trucount® tubes (BD). Flow cytometric data was acquired on a FACSCelesta flow cytometer (BD Biosciences) and analyzed with FlowJo X software (Tree Star). Results were depicted and statistics (one-way ANOVA followed by Dunnett's multiple comparison test) analyzed using GraphPad Prism 6. The number of CD4+ T cells per μl blood was significantly increased by mIL7-mAlb (FIG. 14, left). Only a small, non-significant increase was observed in the mAlb-IL2 group. All other groups showed similar CD4 T cells levels than the mAlb control group. As expected, mAlb-IL2 significantly increased the fraction of CD25+ FoxP3+ CD4+ Tregs (FIG. 14, right). Importantly, mIL7-mAlb was able to decrease the fraction of Tregs. Likewise, as mIL7-mAlb strongly increases CD4+ T-cell numbers and decreases the fraction of Tregs it can be assumed that the fraction of effector T cells is increased. Noteworthy, coupling IFNβ to mAlb-IL2 (mIFNβ-mAlb-mIL2) was able to normalize Treg frequencies to baseline level.

Example 9: Influence of Cytokine Albumin Fusions on the Fraction of Long Lived CD127+ Memory Precursor Cells Antigen specific T cells can be subdivided into KLRG-1+, CD127− short lived effector T cells (SLECs) and long lived CD127+ T cells that are precursors of memory T cells (Kaech, S. M. et al. Nat. Immunol. 4, 1191-1198 (2003); Joshi, N. S. et al. Immunity 27, 281-295 (2007)). Both subsets demonstrate equivalent cytotoxicity but differ in their survival capacity (Yuzefpolskiy, Y., Baumann, F. M., Kalia, V. & Sarkar, S. Cell. Mol. Immunol. 12, 400-408 (2015)). CD127+ T cells can be subdivided into KLRG-, CD127+ so called memory precursor effector cells (MPECs) and so far uncharacterized KLRG+, CD127+ T cells. The latter might be MPECs that have proliferated several times or are in transition to becoming KLRG−, CD127+ MPECs.

We were interested whether albumin cytokine fusion proteins would alter the ratio of memory precursor T cells to SLECs. For example, it has been shown that IL2 and IL7 play important roles in T-cell survival an memory formation (Blattman, J. N. et al. Nat. Med. 9, 540-7 (2003); Kaech, S. M. et al. Nat. Immunol. 4, 1191-1198 (2003); Fry, T. J. &

Mackall, C. L. Blood 99, 3892-3904 (2002); Palmer, M. J. et al. Cell. Mol. Immunol. 5, 79-89 (2008)), respectively. 31 days after tumor inoculation blood of mice shown in FIG. 9 was analyzed for expression of KLRG1 and CD127 on gp70 AH1 tetramer+ CD8+ T cells. Staining of blood for flow cytometry analysis was performed as described in Example 7. Two-way ANOVA analysis followed by Dunnett's multiple comparisons test was used to determine significant differences in the fraction of T-cell subtypes. SLEC fractions were significantly reduced for all constructs except mIFNβ-mAlb (FIG. 15). Strongest reduction of SLECs was achieved after mAlb-IL2 and IL7-mAlb treatment. Only IL7-mAlb was able to significantly increase KLRG−, CD127+ MPECs. KLRG+, CD127+ cells were significantly increased in the groups that received mAlb-mIL2, mIFNβ-mAlb-mIL2 and IL7-mAlb. Importantly, the fraction of gp70 specific SLEC cells positively correlated with tumor size (FIG. 16A). In contrast, a higher fraction of CD127 (IL7 receptor) positive gp70 specific T cells strongly correlated with a lower tumor size (FIG. 16B).

Example 10: Combination of mAlb-mIL2 and mIL7-mAlb with mRNA Vaccination and PD-L1 Blockade Results in Complete Tumor Eradication mAlb-mIL2 and IL7-mAlb constructs both had their individual strengths. mAlb-mIL2 boosted high antigen-specific T-cell numbers very early (FIG. 10) and selectively (FIG. 12) but additionally increased the frequency of Tregs (FIG. 14, right). IL7-mAlb, however, strongly increased CD4+ effector T cells, decreased the fraction of Tregs (FIG. 14) and was particular effective in supporting CD127+ memory precursor T cells. We therefore concluded that combination treatment with both constructs might synergistically boost anti-tumor efficacy.

As described in Example 6, BALB/c mice were injected s.c. with $5\times10^5$ CT26 tumor cells in 200 μl PBS into the right flank. In comparison to FIG. 9, treatment was started on day 13 in order to obtain larger tumors. Again, mice received weekly gp70 RNA-LPX and anti-PD-L1 blocking antibody injections. After two days, nucleoside-modified mRNA encoding Alb-mIL2, mIL7-mAlb or both (1 μg each) was administered (FIG. 17, upper panel). Both, Alb-mIL2 and mIL7-mAlb treatment groups showed reduced tumor growth in comparison to the control group (mAlb). Alb-mIL2 induced in 55% and mIL7-mAlb in 36% of mice a complete tumor rejection in contrast to 18% in the control group. Strikingly, combination of Alb-mIL2 and mIL7-mAlb resulted in complete tumor rejection in 100% of mice (FIG. 17).

Example 11: mAlb-mIL2 and mIL7-mAlb Synergize in Boosting Long Lasting Vaccine Induced T-Cell Responses As described in Example 7 and Example 9 blood of mice depicted in FIG. 17 was analyzed by flow cytometry for gp70 AH1 tetramer+ CD8+ T cells (FIG. 18*a*) and their expression of KLRG1 and CD127 (FIG. 18*b*) on day 19, 27 and 34 after tumor inoculation. As in FIG. 10 and FIG. 11, Alb-mIL2 treatment boosted antigen specific T-cell numbers very early. Both Alb-mIL2 and mIL7-mAlb increased the number of antigen specific T cells over the mAlb control. Combination of Alb-mIL2 and mIL7-mAlb induced the highest antigen specific T cells numbers, especially during later time points (FIG. 18A). Similarly, strongest reduction of SLECs and increase in CD127+ gp70 specific T cells was observed in the combination group at day 34 after tumor inoculation (FIG. 18*b*).

Example 12: mIL7-mAlb Normalizes Regulatory T-Cell Numbers Increased by mALb-mIL2

We hypothesized based on the results in FIG. 14 that mIL7-mAlb would be able to reduce the fraction of regulatory T cells increased by Alb-mIL2. As described in Example 8, gp70 specific T cells in blood of mice shown in FIG. 17 were analyzed for the fraction of CD4+ CD25+ FoxP3+ T cells on day 57. Again, the Treg frequency was significantly increased by Alb-mIL2 and decreased by mIL7-mAlb. As hypothesized, combination of both resulted in a Treg frequency similar to the mAlb control (FIG. 19).

Example 13: Construct Design and Validation

Construct Design and mRNA Production

The constructs used in the following examples were designed and mRNA generated as described in Example 1. The coding sequence of murine Interleukin-12 was cloned as a fusion protein between the two subunits p40 and p35 separated by a 39-nucleotide long elastin linker.

Construct Validation

Cytokine expression from the generated mRNAs and biological activity of mIL12 was controlled by lipofection of the respective mRNAs into HEK-293T-17 cells and subsequent analysis of the mIL12 activity in the supernatants using HEK-Blue IL12 cells (Invivogen). Here, 250 ng mRNA/μl Lipofectamine MessengerMax were complexed and used per square centimeter culture dish for lipofection of HEK-293T-17 cells of approximately 80% confluence. Supernatants were collected under sterile conditions after 24 hours of expression and stored at 80° C. until further use. Biological activity of mIL12 encoding mRNAs was tested using HEK-Blue IL12 cells (Invivogen) according to manufacturers' protocols. These cells express IL12R (IL12 receptor) and binding of IL12 to IL12R induces the expression of a STAT4-inducible secreted embryonic alkaline phosphatase (SEAP) reporter gene. HEK-Blue IL12 cells were cultivated for 24 h in the presence of the above described HEK-293T-17 supernatants. Recombinant human IL12 served as a control and the presence of alkaline phosphatase was determined using the Infinite 200 device (Tecan). Increased expression of the reporter gene SEAP with supernatants containing mIL12 alone as well as mIL12 fused to mAlb confirmed biological activity of these constructs similar to the recombinant protein (FIG. 20).

Example 14: Selective Translation of mRNA Encoded Proteins in Lymphoid Tissue Resident DCs For the induction of antigen-specific immunity, antigen presentation needs to take place in lymphoid tissues and specifically in antigen-presenting DCs. However, antigen delivery alone is not sufficient to mount adequate immune responses, but cytokines need to be present to modulate T-cell responses in accordance with the nature of the pathogenic threat. Cytokines such as IL12 strongly promote Th1 immunity characterized by highly proliferating T cells and production of IFNγ. The expression of such potent cytokines during T cell priming is tightly regulated, and exogenous supply needs to be limited to the microenvironment of interest in order to avoid systemic adverse effects. In order to deliver such cytokines according to their physiological function, we aimed to develop a formulation that directs the translation of antigen-encoding mRNA exclusively to lymphoid tissues and specifically DCs.

We found that slightly negatively charged liposomal mRNA formulations were most suited to transfect specifically DCs in the spleen, lymph nodes and the bone marrow. In order to visualize biodistribution of antigen expression delivered by this formulation in vivo, 6-9 week old BALB/c mice (n=5 per group, purchased from Janvier Labs) were injected intravenously (i.v.) with 20 μg LUC-encoding RNA-LPX or LUC mRNA alone and bioluminescence was determined 6 h after injection by in vivo imaging using the Xenogen IVIS Spectrum imaging system (Caliper Life Sciences) (ex vivo lymph nodes and bone marrow imaging: 24 h after i.v. injection of 100 μg LUC RNA-LPX). Briefly, an aqueous solution of D-luciferin (250 μl, 1.6 mg, BD Biosciences) was injected intraperitoenally (i.p.) and emitted photons of live animals or extracted tissues were quantified 10 min later with an exposure time of 1 min. Regions of interest (ROI) were quantified as average radiance (photons/sec/cm$^2$/sr, represented by color bars) (IVIS Living Image 4.0). As depicted in FIG. 21A, LUC mRNA when formulated as RNA-LPX and injected i.v. was translated exclusively in lymphoid tissues, predominantly in the spleen, but also in inguinal lymph nodes and in thigh and shin bones (FIG. 21B). Translation of naked mRNA was not detected in any of these tissues nor in any other tissues due to rapid degradation upon entry into the blood vasculature.

In order to ascertain CD11c+ DCs as cellular target of formulated mRNA, CD11c$^+$ APCs were depleted in CD11c-DTR mice. For depletion of CD11c$^+$ cells, CD11c-DTR mice (n=3 per group) were treated i.p. with 4 ng/g body weight diphtheria toxin (DT) diluted in 200 μl PBS 12 h prior to administration of 100 μg LUC RNA-LPX (depletion efficiency of CD11c$^+$ DTR$^+$ cells: >97.2%). Depletion of CD11c$^+$ cells was specific, other cells were not affected. Bioluminescence was quantified in the spleen and inguinal lymph nodes in vivo 6 h after injection as described above. Bioluminescence of bone marrow single-cell suspensions was quantified by ex vivo LUC assay. Single-cell suspensions were prepared from the bone marrow of femur and tibia bones from mice 6 h after injection and 5×10$^6$ cells were plated in 96-well Nunc white plates (Thermo Scientific). Cell suspensions were treated with the equal volume of Bright-Glo luciferin reagent (Promega), incubated for 3 min on a microplate shaker and bioluminescence was measured with an Infinite M200 plate reader (Tecan) with an integration time of 1 s. Background luminescence measured in cells obtained from untreated mice were within the range of 15±5 counts per second (cps). As shown in FIG. 21C, ablation of CD11c+ cells resulted in a significant reduction of the LUC signal in the spleen, in explanted inguinal lymph nodes and in bone marrow, which strongly pointed at CD11c+ DCs as target cells of mRNA formulated as RNA-LPX.

Example 15: Translation of Formulated mRNA Specifically in the Liver

For cytokines such as IL2 or IL7 to exert their physiological function, i.e. induction of T-cell proliferation and maintenance, systemic availability is key. Targeting of cytokine-encoding mRNA to the liver for transfection of hepatocytes as a pool of protein producers was achieved by i.v. injection of mRNA formulated with a polymer/lipid formulation. In order to confirm selective and high expression of the mRNA encoded protein in the liver, BALB/c mice were injected i.v. with 5 μg polymer/lipid formulated LUC mRNA (n=3) or with the polymer/lipid (TransIT) alone (n=2), and bioluminescence was determined 6, 24, 48, 96 and 120 h after injection by in vivo imaging as described in Example 14. As shown in FIG. 22, bioluminescence was detected exclusively in the liver at all time points. Remarkably, translated and active protein was detectable up to 120 h after injection. Enhanced and prolonged protein availability in the blood, tumor and tumor-draining lymph nodes as a result of strong liver transfection is described in Example 2 and Example 5.

Example 16: High Efficacy and Reduced Toxicity of mIL15 Encoding RNA Targeted to Secondary Lymphoid Organs Compared to Liver Targeted Cytokine Production Certain cytokines like IL15 and IL12 are very toxic when administered systemically. This toxicity is known to be largely dependent on secondary IFNγ release which mediates for example gastrointestinal and liver dysfunction (Guo, Y. et al. J. Immunol. 195, 2353-64 (2015); Car, B. D., Eng, V. M., Lipman, J. M. & Anderson, T. D. Toxicol. Pathol. 27, 58-63). Their therapeutic efficacy, however, depend on activation of immune cell subtypes such as NK cells, T cells and DCs which are most prevalent in secondary lymphoid tissue.

We hypothesized that targeting mIL15 into the secondary lymphoid organs should diminish systemic toxicity while retaining therapeutic efficacy. In order to test this, we inoculated 6-9 week old BALB/c (n=5 per group, purchased from Janvier Labs) i.v. with 4×10$^5$ CT26-B2MKO colon carcinoma cells in 200 μl PBS (phosphate buffered saline). CT26-B2MKO cells lack surface expression of MHC class I resulting in improved recognition by NK cells which can be activated by mIL15. Four and seven days after tumor inoculation, mice were treated with mIL15 RNA (mouse Interleukin-15 fused to the murine Interleukin-15 receptor α chain) either delivered via RNA-LPX into secondary lymphoid organs (40 μg RNA-LPX i.v.) (as described in Example 14) or into the liver (3 μg RNA formulated in TransIT (Mirrus) i.v.) (as described in Example 15). 12 days after tumor inoculation lungs were stained with blue ink, fixated via Fekete's solution and tumor nodules were counted as described elsewhere (Kreiter, S. et al. Nature (2015). 520, 692-696). As hypothesized, liver targeted delivery which resulted in systemic availability of mIL15 lead to severe toxicity. All mice in this group died after the second mRNA administration despite a very low dose. In contrast, mice that received mRNA delivered solely to secondary lymphoid organs stayed alive, even though 13 times more mRNA was administered. All mice treated with mIL15 mRNA delivered to secondary lymphoid organs were tumor free whereas up to several hundred tumor nodules were detected in control animals (FIG. 23).

Example 17: Boost of Tumor-Specific T Cell Therapy and Therapeutic Efficacy with Combination of mIL12 and mIL2 Targeted According to Physiological Function Similarly, we hypothesized that targeting IL12 into to secondary lymphoid organs would result in tolerable toxicity while showing robust therapeutic efficacy. IL12 is an important cytokine released by DCs during priming of T cells and mediating the differentiation of naïve T cells into an antitumoral or antiviral Th1 type of CD4+ or CD8+ T cells. For this reason, IL12 should, when delivered into the secondary lymphoid organs, potentiate the effect of particularly T-cell vaccines. Another cytokine of interest, IL2, exerts its physiological function not only in lymphoid tissues during T-cell priming but preferentially in the periphery where it fosters proliferation of newly primed T cells leaving secondary lymphoid organs, and promotes their functional maintenance in the tumor microenvironment. Keeping in mind the resulting spatio-temporal requirements for these two cytokines, we intended to combine delivery of mIL12 to lymphoid tissues with slightly delayed, systemic delivery of mIL2 in the context of mRNA vaccination and checkpoint blockade. C57BL/6 mice (n=11 per group) purchased from Envigo were inoculated s.c. with $3\times10^5$ B16F10 melanoma cells (ATCC) in 100 µl PBS. Eight days after tumor inoculation mice were stratified according to tumor size and received either an RNA-LPX based T-cell vaccine i.v. containing 10 µg of the differentiation antigen tyrosinase related protein-2 ($TRP2_{180-188}$) as well as 10 µg of the MHC class II-restricted neoantigen B16_M30[9], or irrelevant mRNA (20 µg vaccine backbone without insert). All mice received 200 µg (consecutive treatments with 100 µg) of an anti-PD-L1 antibody (clone 6E11, mIgG2A, L234A, L235A, P329G; Genentech) in 200 µl PBS i.p. Mice were co-injected i.v. with 3 µg (1 µg from fourth treatment on) mIL12 mRNA or irrelevant mRNA delivered as RNA-LPX (delivery to secondary lymphoid organs). Roughly 48 h later, 1 µg mRNA encoding mIL2-mAlb or 1 µg mAlb control formulated with TransIT (delivery to liver for systemic availability) was injected i.v. The treatment schedule was repeated weekly for seven weeks. IL12 treatment strongly improved the immunotherapy resulting in survival of 80% of mice for more than 60 days (FIG. 24A). When either mIL12 or mIL2 were omitted, only 45% or 64% of mice survived until day 60, respectively. Only 9% of the control mice receiving control mRNA combined with PD-L1 antibody were alive at this time point. In addition, the majority of mice receiving mRNA vaccination with PD-L1 antibody and mIL12 combined with mAlb-mIL2, mIL12 alone or mAlb-mIL2 alone showed signs of vitiligo, i.e. loss of fur pigmentation around the eyes as a result of strong autoimmunity against TRP-2 containing cells due to the treatment (FIG. 24B). Due to ethical reasons, a control group testing administration of IL12 delivered into the liver to show intolerable toxicity was not added in this experiment.

Tables

TABLE 1

Significance values for FIG. 6

| One-way ANOVA + Dunnett's multiple comparisons test | Summary |
|---|---|
| CD4+ T cells | |
| mAIb vs. mIL2 | ns |
| mAIb vs. mAIb-mIL2 | * |
| mAIb vs. mIFNb | ns |
| mAIb vs. mIFNb-mAIb | ns |
| mAIb vs. mIFNb-mIL2 | ns |
| mAIb vs. mIFNb-mAIb-mIL2 | |
| CD4+ CD25+ T cells | |
| mAIb vs. mIL2 | ns |
| mAIb vs. mAIb-mIL2 | **** |
| mAIb vs. mIFNb | ns |
| mAIb vs. mIFNb-mAIb | ns |
| mAIb vs. mIFNb-mIL2 | ns |
| mAIb vs. mIFNb-mAIb-mIL2 | ns |

TABLE 1-continued

Significance values for FIG. 6

| One-way ANOVA + Dunnett's multiple comparisons test | Summary |
|---|---|
| CD8+ T cells | |
| mAIb vs. mIL2 | ns |
| mAIb vs. mAIb-mIL2 | * |
| mAIb vs. mIFNb | ns |
| mAIb vs. mIFNb-mAIb | ns |
| mAIb vs. mIFNb-mIL2 | ns |
| mAIb vs. mIFNb-mAIb-mIL2 | ns |
| B cells | |
| mAIb vs. mIL2 | ns |
| mAIb vs. mAIb-mIL2 | * |
| mAIb vs. mIFNb | ns |
| mAIb vs. mIFNb-mAIb | ns |
| mAIb vs. mIFNb-mIL2 | ns |
| mAIb vs. mIFNb-mAIb-mIL2 | ns |
| NK cells | |
| mAIb vs. mIL2 | ns |
| mAIb vs. mAIb-mIL2 | ** |
| mAIb vs. mIFNb | ns |
| mAIb vs. mIFNb-mAIb | ns |
| mAIb vs. mIFNb-mIL2 | ns |
| mAIb vs. mIFNb-mAIb-mIL2 | ns |

TABLE 2

Significance values for FIG. 7

| One-way ANOVA + Dunnett's multiple comparisons test | Summary |
|---|---|
| DC (CD40) | |
| mAIb vs. mIL2 | ns |
| mAIb vs. mAIb-mIL2 | ns |
| mAIb vs. mIFNb | **** |
| mAIb vs. mIFNb-mAIb | *** |
| mAIb vs. mIFNb-mIL2 | **** |
| mAIb vs. mIFNb-mAIb-mIL2 | **** |
| DC (CD69) | |
| mAIb vs. mIL2 | ** |
| mAIb vs. mAIb-mIL2 | ns |
| mAIb vs. mIFNb | **** |
| mAIb vs. mIFNb-mAIb | **** |
| mAIb vs. mIFNb-mIL2 | **** |
| mAIb vs. mIFNb-mAIb-mIL2 | **** |
| DC (CD86) | |
| mAIb vs. mIL2 | ns |
| mAIb vs. mAIb-mIL2 | ns |
| mAIb vs. mIFNb | **** |
| mAIb vs. mIFNb-mAIb | *** |
| mAIb vs. mIFNb-mIL2 | **** |
| mAIb vs. mIFNb-mAIb-mIL2 | **** |
| NK cells | |
| mAIb vs. mIL2 | ns |
| mAIb vs. mAIb-mIL2 | ** |
| mAIb vs. mIFNb | **** |
| mAIb vs. mIFNb-mAIb | **** |
| mAIb vs. mIFNb-mIL2 | **** |
| mAIb vs. mIFNb-mAIb-mIL2 | **** |
| T cells (CD69) | |
| mAIb vs. mIL2 | ns |
| mAIb vs. mAIb-mIL2 | ns |
| mAIb vs. mIFNb | **** |

TABLE 2-continued

Significance values for FIG. 7

| One-way ANOVA + Dunnett's multiple comparisons test | Summary |
| --- | --- |
| mAlb vs. mIFNb-mAlb | **** |
| mAlb vs. mIFNb-mIL2 | ** |
| mAlb vs. mIFNb-mAlb-mIL2 | ** |

TABLE 3

Significance values for FIG. 15

| Two-way ANOVA + Dunnett's multiple comparisons test | Summary |
| --- | --- |
| KLRG1+/CD127− (SLEC) | |
| mAlb vs. mAlb-mIL2 | **** |
| mAlb vs. mIFNb-mAlb | ns |
| mAlb vs. mIFNb-mALb-mIL2 | *** |
| mAlb vs. mIL7-mAlb | **** |
| mAlb vs. mIL15sushi-mAlb | ** |
| KLRG1−/CD127+ (MPEC) | |
| mAlb vs. mAlb-mIL2 | ns |
| mAlb vs. mIFNb-mAlb | ns |
| mAlb vs. mIFNb-mALb-mIL2 | ns |
| mAlb vs. mIL7-mAlb | * |
| mAlb vs. mIL15sushi-mAlb | ns |
| KLRG1+/CD127+ (Transition) | |
| mAlb vs. mAlb-mIL2 | ** |
| mAlb vs. mIFNb-mAlb | ns |
| mAlb vs. mIFNb-mALb-mIL2 | *** |
| mAlb vs. mIL7-mAlb | *** |
| mAlb vs. mIL15sushi-mAlb | ns |
| KLRG1−/CD127− | |
| mAlb vs. mAlb-mIL2 | ns |
| mAlb vs. mIFNb-mAlb | ns |
| mAlb vs. mIFNb-mALb-mIL2 | ns |
| mAlb vs. mIL7-mAlb | ns |
| mAlb vs. mIL15sushi-mAlb | ns |

ns: not significant.

Example 18: Liver but Not Secondary Lymphoid Organ Targeted mAlb-mIL2 Readily Increases Vaccine Induced T-Cell Responses As observed in Examples 16 and 17, targeting of cytokine RNA to secondary lymphoid organs can have strong therapeutic efficacy and can diminish toxicity of certain cytokines such as IL12. However, we hypothesized that for other cytokines, e.g. IL2 and IL7, systemic availability of high amounts of cytokine is required for a strong and prolonged effect on tumor antigen specific T cells. Hence, we compared the effect of mAlb-mIL2 RNA delivered with TransIT or formulated as RNA-LPX on gp70 specific T-cell numbers. BALB/c mice (n=5) were treated with gp70 RNA-LPX vaccination (20 μg i.v.) and an anti-PD-L1 blocking antibody (100 μg i.p.) on day 0 and 7, followed two days later by administration of 1 μg mRNA encoding mAlb-mIL2 either in TransIT or as RNA-LPX. Gp70 specific T-cell responses were measured in blood as described for Example 6. As shown in FIG. 25, only liver targeted mAlb-mIL2 (mAlb-mIL2 (TransIT)) but not secondary lymphoid organ targeted mAlb-mIL2 (mAlb-mIL2 (RNA-LPX) was able to significantly increase gp70 specific $CD8^+$ T-cell responses 7 days after the first (left) or second vaccination (right).

Example 19: Construct Design and Validation

Construct Design and mRNA Production

DNA plasmid constructs for in vitro transcription of human cytokine encoding mRNAs were designed according to Example 1. Cytokine and Alb coding sequences originate from Homo sapiens and no changes in the resulting amino acid sequences were introduced (hIL2: NP_000577.2; hIL7: NP_000871.1; NCBI protein resource; https://www.ncbi.nlm.nih.gov/protein/). hAlb was added either at the N- or C-terminus of the cytokine. mRNA was generated by in vitro transcription, capped and purified as described in Example 1.

Construct Validation

Cytokine expression from the generated mRNAs was analyzed by lipofection of the mRNA into HEK-293T-17 cells and subsequent analysis of resulting supernatants using enzyme-linked immunosorbent assay (ELISA). One day prior to lipofection, $1.2\times10^6$ HEK-293T-17 cells were seeded in 3 mL DMEM (Life Technologies GmbH, cat. no. 31966-021)+10% fetal bovine serum (FBS, Biochrom GmbH, cat. no. S0115) in 6-well plates. For lipofection, 3 μg mRNA was formulated under sterile and RNase-free conditions using 400 ng mRNA per μL Lipofectamine MessengerMax (Thermo Fisher Scientific, cat. No. LMRNA015) and applied per 10 $cm^2$ culture dish to the HEK-293T-17 cells at approximately 80% confluence. After 20 h of expression, cell-free supernatants were collected under sterile conditions and stored at −20° C. until further use. The presence of hIL2 cytokine in cell culture supernatants was determined by analyzing the binding of hAlb-hIL2 and hIL2-hAlb to recombinant human CD25 in ELISA. Here, 1 μg/mL recombinant human CD25 (C-Fc, Novoprotein cat no. CJ78) was coated in 100 μL DPBS to high protein-binding 96-well plates (Nunc MaxiSorp™, Thermo Fisher Scientific, cat. no. 439454). Supernatants containing hIL2 were applied to coated CD25 in 1:4-dilution and bound protein was detected via an HRP-conjugated anti-human Serum Albumin antibody (Abcam, cat. no. ab8941). General ELISA reagents and procedures were used according to the protocol of DuoSet ELISA Ancillary Reagent Kit 2 (R&D Systems, cat. No. DY008). In case of hIL7, cytokine levels in cell culture supernatants were determined using commercially available Human IL-7 DuoSet ELISA (R&D Systems, cat. no. DY207) according to the manufacturer's protocol.

Cell culture supernatants containing hIL2 or hIL7 were also used for Western Blot analysis to semi-quantitatively confirm cytokine expression of selected constructs under denaturing conditions. Therefore, total protein was concentrated using appropriate VivaSpin columns (Sartorious AG) and concentrations were assessed by quantification of prominent bands after sample separation on SDS-PAGE and Coomassie staining using Image Quant TL software (GE Healthcare). For Western blotting homogenous protein amounts were separated by SDS-PAGE and transferred on nitrocellulose membrane by semi-dry or wet-blot protocols. After blotting nitrocellulose membranes were blocked (5% non-fat dry milk in 1×PBS-T) followed by incubation with appropriate dilutions of primary (anti-hIL2: Abcam (ab92381), anti-hIL7: Abcam (ab193358)) and secondary antibody. The membranes were washed (1×PBS-T) before and after secondary antibody incubation. Chemiluminescent signals developing after addition of the Lumi-Light Western Blotting Substrate (Roche), SuperSignal®West Dura Extended Duration Substrate (Thermo Fisher Scientific) or Trident femto Western HRP Substrate (Gene Tex) were recorded using the LAS 4000 system (GE Healthcare).

The biological activity of hIL2 and hIL7 was assessed by analyzing the cytokine-mediated enhancement of antigen-unspecific proliferation of human CD4+ T cell and CD8+ T cell populations in human peripheral blood mononuclear cells (PBMC). Additionally, the biological activity of hIL2 was assessed via the hIL2-dependent proliferation of murine CTLL-2 cells (Mouse C57BL/6 T cell line, ATCC TIB-214) highly expressing CD25. For CTLL-2 proliferation analysis, cells were harvested, washed twice with DPBS to remove any residual IL2 and resuspended in RPMI 1640 (Life Technologies GmbH, cat. no. 61870010) supplemented with 10% FBS and 1 mM sodium pyruvate (Life Technologies GmbH, cat. no. 11360070). A total of 5,000 cells/well were seeded in white 96-well flat-bottom plates (Fisher Scientific GmbH, cat. no. 10072151) and incubated with four-fold serially diluted hIL2-containing supernatants. After three days of culture proliferation was measured by quantitating viable cells via ATP amount using the CellTiter-Glo® 2.0 Assay (Promega, cat. no. G9242). Luminescence was recorded on a Tecan Infinite® F200 PRO reader (Tecan Deutschland GmbH) and dose-response curves were plotted in Graph Pad Prism version 6.04 (GraphPad Software, Inc.). In order to measure human T cell proliferation, PBMCs were obtained from buffy coats of healthy donors by Ficoll-Paque (VWR international, cat. no. 17-1440-03) density gradient separation. PBMCs were labeled using 1.6 μM carboxyfluorescein succinimidyl ester (CFSE; Thermo Fisher, cat. no. C34564). 75,000 CFSE-labeled PBMCs were seeded per well in a 96-well round-bottom plate (Costar, cat. no. 734-1797) in Iscove's Modified Dulbecco's Medium (IMDM; Life Technologies GmbH, cat. no. 12440-053) supplemented with 5% plasma-derived human serum (PHS; One Lambda Inc., cat. no. A25761) and incubated with a sub-optimal concentration of anti-CD3 antibody (clone UCHT1; R&D Systems, cat. no. MAB100; 0.03 μg/mL final concentration). In parallel, four-fold serial dilutions of hIL2- and hIL7-containing supernatants were generated in IMDM supplemented with 5% PHS. Seeded cells were mixed 1:1 (referring to the volume of the culture medium of the seeded cells) with supernatants and stimulated for four days at 37° C., 5% $CO_2$. In case of hIL-7, PBMCs were harvested and stained with the following reagents all diluted 1:100 in FACS-buffer (D-PBS containing 5% FBS and 5 mM EDTA): anti-human CD4-PE (TONBO Bioscience, cat. 50-0049), anti-human CD8-PE-Cy7 (TONBO Bioscience, cat. 60-0088) and 7-MD (Beckman Coulter, cat. no. A07704). Flow cytometric analysis was performed on a BD FACSCanto™ II flow cytometer (Becton Dickinson) with CFSE dilution as proliferation read-out. Acquired proliferation data were analyzed using FlowJo 10.4 software and exported values for % divided cells were used to plot dose-response curves in GraphPad Prism version 6.04 (GraphPad Software, Inc.).

In hCD25-binding ELISA as well as hIL7 ELISA, both orientations hAlb-hIL2 and hIL2-hAlb or hAlb-hIL7 and hIL7-hAlb, respectively, resulted in comparable signals indicating that all tested cytokines were sufficiently expressed into the cell culture supernatant and that orientation does not affect cytokine expression (FIG. 26A, FIG. 27A). In addition, cytokine expression for hAlb-hIL2 and hIL7-hAlb was confirmed by Western blot analysis (FIG. 26B, FIG. 27B). hAlb-hIL2 and hIL2-hAlb induced proliferation of CTLL-2 cells as well as enhanced antigen-unspecific proliferation of human CD4+ and CD8+ T cells in a dose-dependent manner. Both orientations performed on par indicating that the position of hAlb within the molecule does not affect biological activity of hIL2 (FIG. 26C, D). Likewise, hAlb-hIL7 and hIL7-hAlb enhanced antigen-unspecific proliferation of human CD4+ and CD8+ T cells in a dose-dependent manner. The two different orientations performed similar, however, hIL7-hAlb appeared to be slightly, but not significantly more bioactive than hAlb-hIL7 (FIG. 27C). Based on these results, hAlb-hIL2 and hIL7-hAlb were selected for further experiments.

Example 20: The Respective Order of Cytokine and Albumin Moiety Within the Active Protein Neither Influences Stability, Pharmacokinetic Profile Nor Functionality In Vivo The location of the pharmacokinetic modifying group may be located N- or C-terminally with regard to the cytokine. In order to determine whether one or the other location influences stability, systemic bioavailability or functionality, human IL2 (hIL2) was fused to the N-(hIL2-hAlb) or C-terminus (hAlb-hIL2) of human Albumin (hAlb) and cytokine levels were determined in the blood circulation. Female BALB/c mice (12-15 weeks old) (n=3 mice per group and time-point) were purchased from Janvier Labs and injected with 1 μg hIL2-hAlb- or hALb-hIL2-encoding mRNA formulated with TransIT (Mirrus) intravenously (i.v.), or formulated control mRNA encoding hAlb only. Blood was retrieved and serum prepared 6, 24 and 48 h and 72 h after injection. Cytokine concentrations were determined using the V-Plex Human IL-2 kit (Meso Scale Diagnostics, LLC) on a MESO QuickPlex SQ120 instrument (Meso Scale Diagnostics, LLC) according to the manufacturer's instructions. In order to investigate potential functional differences, T lymphocyte numbers were determined in the spleen 96 h after injection by flow cytometric analysis of splenocyte single-cell suspensions prepared and stained as described in Example 3. Flow cytometric data were acquired on a FACSCelesta flow cytometer (both BD Biosciences) and analyzed with FlowJo X software (Tree Star). As shown in FIG. 28A, the pharmacokinetic profile of the two different hIL2 fusion proteins is identical, with very similar initial levels of translated protein, as well as systemic availability over time. T lymphocyte subsets CD4+, Treg and CD8+ T cell numbers were similarly expanded with both hIL2 fusion proteins, compared to control animals (FIG. 28B). These sets of data show that the location of the pharmacokinetic modifying group, in this case hAlb, N- or C-terminally with respect to the cytokine, is irrelevant for proper cytokine functionality.

Example 21: Combination of hAlb-hIL2 and hIL7-hAlb with mRNA Vaccination Results in Almost Complete Tumor Eradication In Example 10, mAlb-mIL2 and mIL7-mAlb were shown to boost vaccine-induced antitumoral immunity, especially when applied in combination. In order to confirm these findings with the human cytokine fusions, BALB/c mice (n=11 per group) were injected s.c. with $5\times10^5$ CT26 tumor cells in 200 μl PBS into the right flank, and mice were vaccinated starting from day 10 after tumor inoculation with four weekly doses of 20 μg gp70 RNA-LPX i.v. and either 3 μg hAlb-hIL2, hIL7-hAlb, or the combination of the two, formulated as lipid nanoparticles (LNP) and injected i.v. (liver targeting). Control animals received the mRNA vaccination and hAlb formulated as LNP i.v. Both groups that received either hAlb-hIL2 or hIL7-hAlb reduced and decelerated tumor growth and even rejected established tumors in comparison the control group (hAlb) (FIG. 29A). For hAlbhIL2, none of the tumors grew out while under treatment, which led to high tumor rejection in 64% of the mice, while tumors were rejected in 18% of mice when treated with hIL7-hAlb. Closely resembling their murine counterparts, the combination of hAlb-hIL2 and hIL7-hAlb resulted in tumor rejection and tumor-free survival in 91% of mice compared to no surviving mice in the control group (FIGS. 29A and B).

Example 22: hAlb-hIL2 and hIL7-hAlb Boost and Maintain High Levels of Vaccine Induced Tumor-Specific CD8+ T Cell Responses In line with Example 7 and 11, the effect of fusion protein-encoding mRNA on the expansion of vaccine induced T-cell responses was investigated in response to hAlb-hIL2 and hIL7-hAlb. CT26 tumor bearing mice described in Example 21 were analyzed by flow cytometry for gp70 AH1 tetramer+ CD8+ T cells in blood 7 days after each of three consecutive treatments (day 17, 24 and 31 after tumor inoculation). For this, peripheral blood of mice was collected and stained for gp70 AH1 tetramer+ CD8+ T cells as described in Example 7. Flow cytometric data were acquired on a FACSCelesta flow cytometer (BD Biosciences) and analyzed with FlowJo X software (Tree Star). Gp70 AH1 specific T cells were gated and quantified as described in Example 7. Statistics (one-way ANOVA followed by Dunnett's multiple comparisons test) were analyzed using GraphPad Prism 7.

As revealed by absolute numbers of tumor antigen specific CD8+ T cells as well as the fraction thereof among CD8+ T cells, hAlb-hIL2 treatment boosted tumor antigen specific CD8+ T cells readily after the first vaccination (FIG. 30A), and maintained significantly higher levels over time (FIG. 30B). While hIL7-hAlb did not expand antigen specific CD8+ T cells beyond the control group, the combination of hAlb-h112 and hIL7-hAlb synergized in expanding antigen specific CD8+ T cells over time and was superior to hAlb-hIL2 alone (FIG. 30A, B). Both hAlb-hIL2 and hIL7-hAlb increased the number of CD8+ T cells not specific for the vaccinated tumor antigen, and again the combination of the two cytokines was superior to single treatment (FIG. 30C). As described before for the murine counterparts (Example 8), hAlb-hIL2 and the combination of hAlb-hIL2 and hIL7-Alb were able to expand preferentially antigen specific CD8+ T cells over antigen unspecific CD8+ T cells (FIG. 30D).

Example 23: hAlb-hIL2 Only Initially Expands Treg Cells While hIL7-hAlb Maintains Low Number of Treg Cells Throughout In line with Example 8, the effect of fusion protein-encoding mRNA on the expansion of unwanted Tregs was investigated in response to hAlb-hIL2 and hIL7-hAlb. CT26 tumor bearing mice described in Example 21 were analyzed by flow cytometry for Treg cells in blood 7 days after each of three consecutive treatments (day 17, 24 and 31 after tumor inoculation). For this, peripheral blood of mice was collected and stained for Treg cells as described in Example 8. Flow cytometric data were acquired on a FACSCelesta flow cytometer (BD Biosciences) and analyzed with FlowJo X software (Tree Star). T reg cells were gated and quantified as described in Example 8.

Although hAlb-hIL2 significantly expands Treg cells initially (FIG. 31A), the number of T reg cells normalizes with continuous treatment and drops below the control level (FIG. 31B). Similarly to the murine counterpart, treatment with hIL7-hAlb does not expand Treg cells upon first treatment, and T reg cell numbers remain controlled throughout further treatments (FIG. 31A, B). The combination of the two cytokines equally reduces T reg cell numbers similarly to the control from the second vaccination on (not statistically significant). Consequently, hAlb-hIL2 and the combination of hAlb-hIL2 and hIL7-hAlb preferentially expand CD8+ T cells over Treg cells (FIG. 32). In particular, hAlb-hIL2 and the combination of hAlb-hIL2 and hIL7-hAlb greatly increase the number of antigen specific as well as unspecific CD8+ T cells over Treg cells (FIG. 32A), while hIL7-hAlb preferentially expands unspecific CD8+ T cells not addressed by the vaccine (FIG. 32B).

The invention claimed is:

1. A method for inducing an immune response against an antigen in a subject comprising administering to the subject:

a. RNA encoding IL-2 attached to a moiety selected from the group consisting of serum albumin, an immunoglobulin Fc domain, transferrin, and Fn3 (extended pharmacokinetic (PK) IL-2) and RNA encoding extended IL-7 attached to a moiety selected from the group consisting of serum albumin, an immunoglobulin Fc domain, transferrin, and Fn3 (extended pharmacokinetic (PK) IL-7); and b. RNA encoding a peptide or protein comprising an epitope for inducing said immune response against said antigen in said subject.

2. A medical preparation comprising:

a. RNA encoding IL-2 attached to a moiety selected from the group consisting of serum albumin, an immunoglobulin Fc domain, transferrin, and Fn3 (extended-pharmacokinetic (PK) IL-2) and RNA encoding IL-7 attached to a moiety selected from the group consisting of serum albumin, an immunoglobulin Fc domain, transferrin, and Fn3 (extended-pharmacokinetic (PK) IL-7); and b. RNA encoding a peptide or protein comprising an epitope for inducing an immune response against an antigen in a subject.

3. The medical preparation of claim 2, wherein the moiety of the extended-PK IL-2 is mouse serum albumin or human serum albumin.

4. The medical preparation of claim 2, further comprising:

c. an immune checkpoint inhibitor targeting the interaction between PD-1 and PD-L1.

5. The medical preparation of claim 4, wherein the immune checkpoint inhibitor is an antibody or antibody fragment that targets PD-1, PD-L1, or CTLA-4.

6. The medical preparation of claim 2, which is a pharmaceutical composition comprising the RNAs.

7. The medical preparation of claim 6, wherein the pharmaceutical composition further comprises one or more pharmaceutically acceptable carriers, diluents and/or excipients.

8. The medical preparation of claim 2, wherein the RNA encoding extended-PK IL-2, or the RNA encoding extended-PK IL-7, or both the RNA encoding extended-PK IL-2 and the RNA encoding extended-PK IL-7 is present in a form selected from a liquid form, a solid form, or a combination thereof.

9. The medical preparation of claim 8, wherein the solid form is a frozen form or a dehydrated form.

10. The medical preparation of claim 9, wherein the dehydrated form is a freeze-dried or spray-dried form.

11. The medical preparation of claim 2, wherein each respective moiety is mouse serum albumin or human serum albumin.

12. The medical preparation of claim 2, wherein the IL-2 of the extended-PK IL-2 is human IL-2.

13. The medical preparation of claim 2, wherein the IL-7 of the extended-PK IL-7 is human IL-7.

14. The medical preparation of claim 2, wherein the IL-2 of the extended-PK IL-2 is human IL-2 and the IL-7 of the extended-PK IL-7 is human IL-7.

15. The medical preparation of claim 14, wherein the moiety of the extended-PK IL-2 is serum albumin and the moiety of the extended-PK IL-7 is serum albumin.

16. The medical preparation of claim 2, wherein the IL-2 of the extended-PK IL-2 comprises the amino acid sequence of SEQ ID NO: 1.

17. The medical preparation of claim 16, wherein the moiety of the extended-PK IL-2 comprises the amino acid sequence set forth in SEQ ID NO: 5.

18. The medical preparation of claim 2, wherein the IL-7 of the extended-PK IL-7 comprises the amino acid sequence of SEQ ID NO: 2.

19. The medical preparation of claim 18, wherein the moiety of the extended-PK IL-7 comprises the amino acid sequence set forth in SEQ ID NO: 5.

20. The medical preparation of claim 2, wherein the IL-2 of the extended-PK IL-2 comprises the amino acid sequence of SEQ ID NO: 1 and the IL-7 of the extended-PK IL-7 comprises the amino acid sequence of SEQ ID NO: 2.

21. The medical preparation of claim 20, wherein the moiety of the extended-PK IL-2 comprises the amino acid sequence set forth in SEQ ID NO: 5 and the moiety of the extended-PK IL-7 comprises the amino acid sequence set forth in SEQ ID NO: 5.

22. The method of claim 1, wherein the moiety of the extended-PK IL-2 is mouse serum albumin or human serum albumin.

23. The method of claim 1, further comprising administering to the subject:

c. an immune checkpoint inhibitor targeting the interaction between PD-1 and PD-L1.

24. The method of claim 23, wherein the immune checkpoint inhibitor is an antibody or antibody fragment that targets PD-1, PD-L1, or CTLA-4.

25. The method of claim 1, wherein each respective moiety is mouse serum albumin or human serum albumin.

26. The method of claim 1, wherein the IL-2 of the extended-PK IL-2 is human IL-2.

27. The method of claim 1, wherein the IL-7 of the extended-PK IL-7 is human IL-7.

28. The method of claim 1, wherein the IL-2 of the extended-PK IL-2 is human IL-2 and the IL-7 of the extended-PK IL-7 is human IL-7.

29. The method of claim 28, wherein the moiety of the extended-PK IL-2 is serum albumin and the moiety of the extended-PK IL-7 is serum albumin.

30. The method of claim 1, wherein the IL-2 of the extended-PK IL-2 comprises the amino acid sequence of SEQ ID NO: 1.

31. The method of claim 30, wherein the moiety of the extended-PK IL-2 comprises the amino acid sequence set forth in SEQ ID NO: 5.

32. The method of claim 1, wherein the IL-7 of the extended-PK IL-7 comprises the amino acid sequence of SEQ ID NO: 2.

33. The method of claim 32, wherein the moiety of the extended-PK IL-7 comprises the amino acid sequence set forth in SEQ ID NO: 5.

34. The method of claim 1, wherein the IL-2 of the extended-PK IL-2 comprises the amino acid sequence of SEQ ID NO: 1 and the IL-7 of the extended-PK IL-7 comprises the amino acid sequence of SEQ ID NO: 2.

35. The method of claim 34, wherein the moiety of the extended-PK IL-2 comprises the amino acid sequence set forth in SEQ ID NO: 5 and the moiety of the extended-PK IL-7 comprises the amino acid sequence set forth in SEQ ID NO: 5.

* * * * *